US010925857B2

(12) United States Patent
Mancia et al.

(10) Patent No.: US 10,925,857 B2
(45) Date of Patent: Feb. 23, 2021

(54) RATIONAL DRUG DESIGN TARGETING RESISTANT GRAM-NEGATIVE BACTERIAL INFECTIONS TO POLYMYXIN-CLASS ANTIBIOTICS

(71) Applicant: The Trustees of Columbia University in the City of New York, New York, NY (US)

(72) Inventors: Filippo Mancia, New York, NY (US); Vasileios Petrou, Astoria, NY (US); Oliver B. Clarke, New York, NY (US); Jeremie P. Vendome, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 15/775,674

(22) PCT Filed: Nov. 14, 2016

(86) PCT No.: PCT/US2016/061906
§ 371 (c)(1),
(2) Date: May 11, 2018

(87) PCT Pub. No.: WO2017/083859
PCT Pub. Date: May 18, 2017

(65) Prior Publication Data
US 2019/0231747 A1    Aug. 1, 2019

Related U.S. Application Data

(60) Provisional application No. 62/254,481, filed on Nov. 12, 2015.

(51) Int. Cl.
| | |
|---|---|
| A61K 31/4155 | (2006.01) |
| A61K 31/21 | (2006.01) |
| A61K 31/426 | (2006.01) |
| A61K 31/4709 | (2006.01) |
| A61K 31/427 | (2006.01) |
| A61K 38/12 | (2006.01) |
| A61P 31/04 | (2006.01) |
| C07D 209/20 | (2006.01) |
| C07D 417/06 | (2006.01) |
| C07K 7/62 | (2006.01) |
| C07D 231/20 | (2006.01) |
| C12Q 1/18 | (2006.01) |
| C07C 311/49 | (2006.01) |
| C07D 277/36 | (2006.01) |
| A61K 45/06 | (2006.01) |
| A61K 31/18 | (2006.01) |
| A61K 31/405 | (2006.01) |

(52) U.S. Cl.
CPC .......... *A61K 31/4155* (2013.01); *A61K 31/18* (2013.01); *A61K 31/21* (2013.01); *A61K 31/405* (2013.01); *A61K 31/426* (2013.01); *A61K 31/427* (2013.01); *A61K 31/4709* (2013.01); *A61K 38/12* (2013.01); *A61K 45/06* (2013.01); *A61P 31/04* (2018.01); *C07C 311/49* (2013.01); *C07D 209/20* (2013.01); *C07D 231/20* (2013.01); *C07D 277/36* (2013.01); *C07D 417/06* (2013.01); *C07K 7/62* (2013.01); *C12Q 1/18* (2013.01); *G01N 2500/10* (2013.01); *Y02A 50/30* (2018.01)

(58) Field of Classification Search
CPC .... A61K 31/4155; A61K 31/18; A61K 31/21; A61K 31/405; A61K 31/426; A61K 31/427; A61K 31/4709; A61K 38/12; A61K 45/06; A61P 31/04; C07C 311/49; C07D 209/20; C07D 231/20; C07D 277/36; C07D 417/06; C07K 47/62; C12Q 1/18; Y02A 50/473; Y02A 50/481; Y02A 50/475; G01N 2500/10
USPC .................................................... 548/373.1
See application file for complete search history.

(56) References Cited

U.S. PATENT DOCUMENTS

| | | |
|---|---|---|
| 2003/0105010 A1 | 6/2003 | Newman et al. |
| 2010/0028862 A1 | 2/2010 | Jarvis et al. |
| 2012/0178805 A1 | 7/2012 | Al-Abed |

(Continued)

FOREIGN PATENT DOCUMENTS

| | | |
|---|---|---|
| JP | S62-501292 A | 5/1987 |
| JP | 2009-530401 A | 8/2009 |
| WO | 86/03489 A1 | 6/1986 |

(Continued)

OTHER PUBLICATIONS

Brvar et al., In silico discovery and biophysical evaluation of novel 5-(2-hydroxybenzylidene) rhodanine inhibitors of DNA gyrase B, 2012, Bioorganic & Medicinal Chemistry, 20, 2572-2580 (Year: 2012).*

(Continued)

*Primary Examiner* — Kristin A Vajda
(74) *Attorney, Agent, or Firm* — Leason Ellis LLP

(57) ABSTRACT

The present invention relates to identification of inhibitors or antagonists of aminoarabinase glycosyltransferase (ArnT) and their use in compositions, methods of treatment or prevention of drug resistant gram negative infections, or inhibiting the growth of gram negative bacterial infections resistant to polymyxin-class antibiotics. In certain aspects, the inhibitors or antagonists can be administered in combination with one or more antibacterial agents.

16 Claims, 32 Drawing Sheets

(56) References Cited

U.S. PATENT DOCUMENTS

2014/0004590 A1  1/2014  Geiss et al.

FOREIGN PATENT DOCUMENTS

WO  2008017734  2/2008
WO  2010/151799 A2  12/2010

OTHER PUBLICATIONS

International Search Report and Written Opinion dated Feb. 15, 2017 corresponding to International Patent Application No. PCT/US16/061906; 15 pages.
Pubchem Bas 00511260, pp. 1-14, Create Date: Jul. 10, 2005; pp. 3 and 5.
Javad Safaei-Ghomi et al: "Pseudo five-component process for the synthesis of 4.4'-(arylmethylene)bis(3-methyl-1H-pyrazo 1-5-ol) derivatives using ZnAl 2 0 4 nanoparticles in aqueous media", RSC ADV., vol. 4. No. 86. Sep. 8, 2014 (Sep. 8, 2014 ). pp. 46106-46113.
Zhongqiang Zhou et al: "An Eco-Friendly One-Pot Synthesis of 4.4'-(Arylmethylene)Bis(1H-Pyrazol-5-0LS) Using [Et 3 NH] [HSO 4 ] as a Recyclable Catalyst", J. Chil. Chem. Soc. No, Sep. 1, 2015 (Sep. 1, 2015). p. 2992.
Moni Reh Zarghani et al: "Sulfonated nanohydroxyapatite functionalized with 2-aminoethyl dihydrogen phosphate (HAP@AEPH 2-SO 3 H) as a new recyclable and eco-friendly catalyst for rapid one-pot synthesis of 4.4'—(aryl methylene)bis(3-methyl-1H-pyrazol-5-ol)s" RSC Advances, vol. 5. No. 107, Sep. 30, 2015 (Sep. 30, 2015), pp. 87769-87780.
S. Bhavanarushi et al: "Synthesis and 1-15 antibacterial activity of 4.4'-(aryl or alkyl methylene)-bis(1H-pyrazol-5-ol) derivatives", Medicinal Chemistry Research., vol. 23, No. 1, May 21, 2013 (May 21, 2013), pp. 158-167.
Hardej D et al: "The synthesis of phenylalanine-derived C5-substituted rhodanines and their activity against selected methicillin-resistant *Staphylococcus aureus* (MRSA) strains", European Journal of Medicinal Chemistry, Editions Scientifique Elsevier, Paris, FR, vol. 45. No. 12, Dec. 1, 2010 (Dec. 1, 2010), pp. 5827-5832.
Burdick Daniel J et al: "N-Benzoyl amino acids as ICAM/LFA-1 inhibitors. Part 2: Structure-activity relationship of the benzoyl moiety", Bioorganic & Medicinal Chemistry Letters, vol. 14, No. 9, 2004, pp. 2055-2059.
Abiola 0. Olaitan et al: "Mechanisms of polymyxin resistance: acquired and intrinsic resistance in bacteria", Frontiers in Microbiology, vol. 5, Nov. 26, 2014 (Nov. 26, 2014).
Nowicki, EM et al., Characterization of Pseudomonas aeruginosa LpxT reveals dual positional 13 lipid A kinase activity and coordinated control of outer membrane modification, Molecular Microbiology 94(3), pp. 728-741, 2014.
Fernandez, L et al., Characterization of the Polymyxin B Resistome of Pseudomonas—aeruginosa, Antimicrobial Agents and Chemotherapy 57(1), pp. 110-119, 2013.
Kline, T et al., Synthesis of and Evaluation of Lipid A Modification by 4-Substituted 4-Deoxy—Arabinose Analogs as Potential Inhibitors of Bacterial Polymyxin Resistance, Bioorganic Medicinal Chemistry Letters, 18(4), pp. 1507-1510, 2007.
Impellitteri et al., "Identification of a functionally important loop in *Salmonella typhimurium* AmT", Biochemistry, 49(1), pp. 29-35, 2009.
Bretscher et al., "Purification and characterization of the L-Ara4N transferase protein AmT from *Salmonella typhimurium*", Protein Expression and Purification, vol. 46, issue 1 pp. 33-39, 2005. Abstract.
Landman et al., Polymyxins revisited. Clin. Microbiol. Rev 21, 449-465 (2008).
Raetz et al., Lipid A modification systems in gram-negative bacteria. Annu. Rev. Biochem. 76, 295-329 (2007).
Trent et al., An inner membrane enzyme in *Salmonella* and *Escherichia coli* that transfers 4-amino-4-deoxy-L-arabinose to lipid A: Induction in polymyxin-resistant mutants and role of a novel lipid-linked donor. J. Biol. Chem. 276, 43122-43131 (2001).

* cited by examiner

FIG. 1A

| Strain | Plasmid | Polymyxin B MIC ($\mu g/ ml^{-1}$) |
| --- | --- | --- |
| WD101 | – | 14.0 ± 2.5 |
| WD101 arnT eptA | – | 1.25 ± 0.25 |
| WD101 arnT eptA | pWSK29/ArnT$_{Cm}$ | 1.0 ± 0.20 |

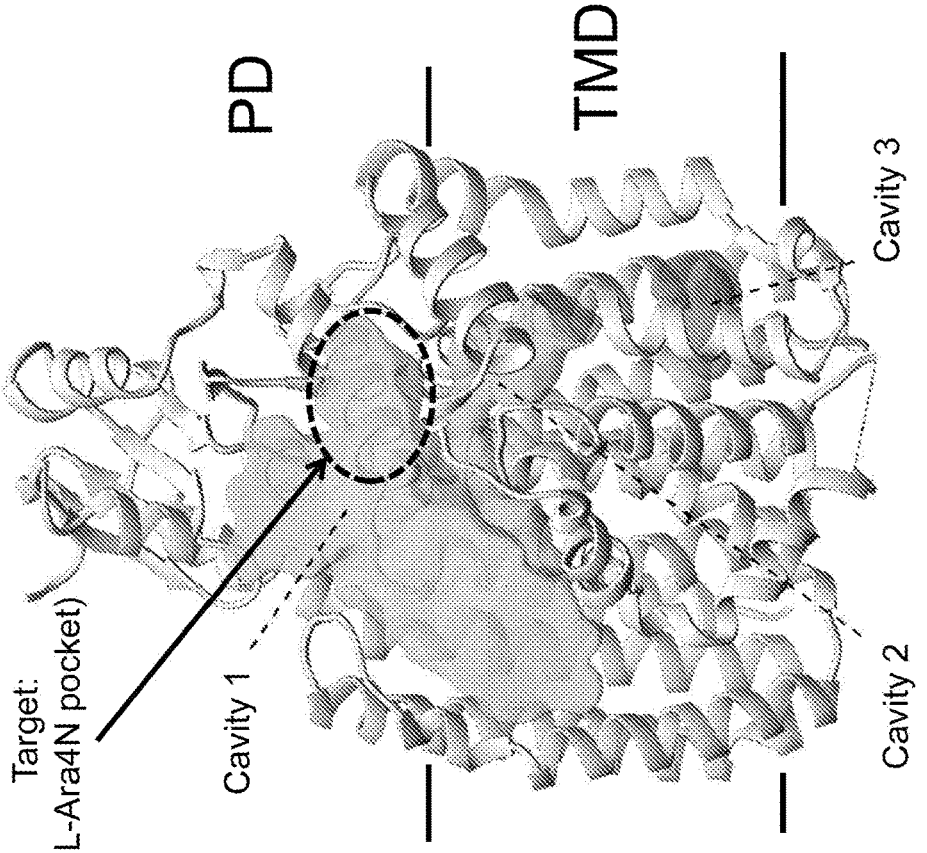
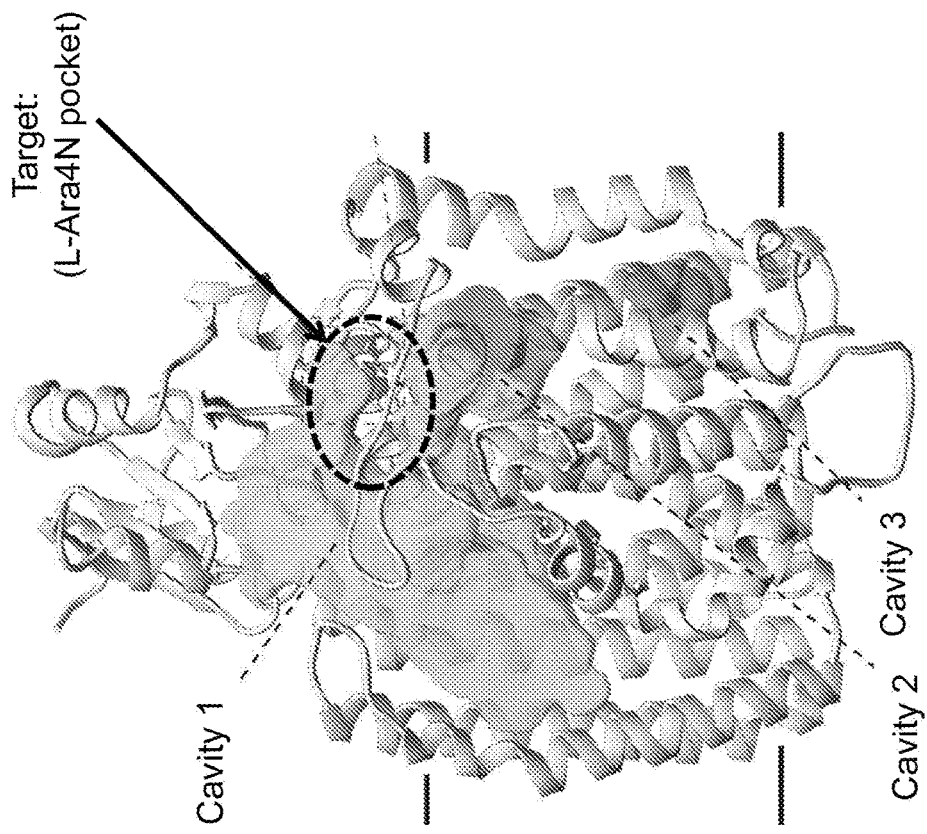
FIG. 3A
FIG. 3B

Class I Compounds

| Compound identifier | Pubchem ID | ZINC ID | Chemical name | Specific effect | Off target effect | Chemical structure |
|---|---|---|---|---|---|---|
| 20 | CID 2910934 | ZINC 04663820 | 4-[(4-chlorophenyl)-(3-methyl-5-oxo-1,2-dihydropyrazol-4-yl)methyl]-5-methyl-1,2-dihydropyrazol-3-one | + | +/− | 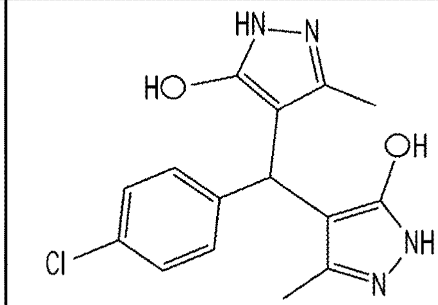 |
| 14 | CID 2920641 | ZINC 04115333 | 5-methyl-4-[[3-methyl-5-oxo-1,2-dihydropyrazol-4-yl]-(4-propan-2-ylphenyl)methyl]-1,2-dihydropyrazol-3-one | + | +/− | 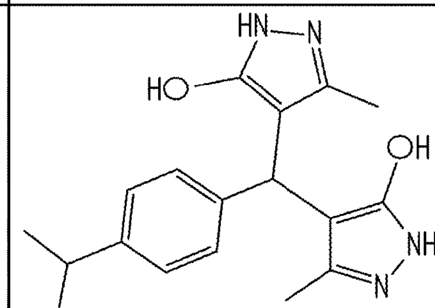 |
| 15 | CID 2913541 | ZINC 04116311 | 4-[[4-(dimethylamino)phenyl]-(3-methyl-5-oxo-1,2-dihydropyrazol-4-yl)methyl]-5-methyl-1,2-dihydropyrazol-3-one | + | +/− | 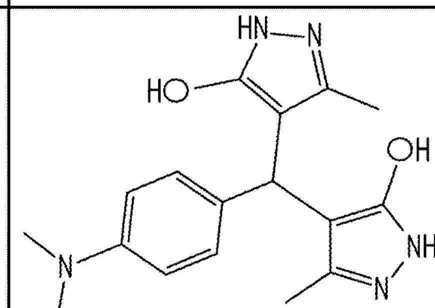 |

FIG. 7A

| | | | | |
|---|---|---|---|---|
| 19 | CID 40489893 | ZINC 04613436 | 4-[(S)-(3,4-dihydroxyphenyl)-(3-methyl-5-oxo-1,2-dihydropyrazol 4 yl)methyl] 5-methyl-1H-pyrazol-3-olate | +/- | − |
| U2 | CID 3149258 | ZINC 19972670 | 4-[(4-hydroxy-3-nitrophenyl)-(3-methyl-5-oxo-1,2-dihydropyrazol-4-yl)methyl]-5-methyl-1,2-dihydropyrazol-3-one | ++ | + |

Class II: Based on Compound 36

| Compound identifier | Pubchem ID | ZINC ID | Chemical name | Specific effect | Off target effect | Chemical structure |
|---|---|---|---|---|---|---|
| 36 | CID 27518080 | ZINC 32575676 | N'-[(3-hydroxy-4-oxocyclohexa-2,5-dien-1-ylidene)methyl]-4-propylbenzenesulfonohydrazide | +++ | +++ | 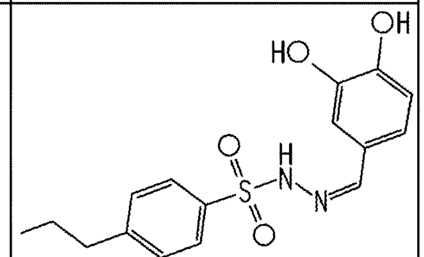 |
| 37 | CID 27518817 | ZINC 32575701 | N'-[(3-hydroxy-4-oxocyclohexa-2,5-dien-1-ylidene)methyl]-4-(2-methylpropyl)benzenesulfonohydrazide | +++ | +++ | 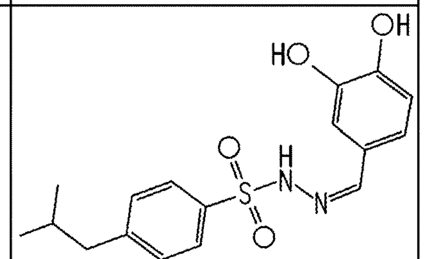 |
| U5 | CID 27518504 | ZINC 17071509 | N'-[(5-hydroxy-6-oxocyclohexa-2,4-dien-1-ylidene)methyl]naphthalene-2-sulfonohydrazide | +++ | + | 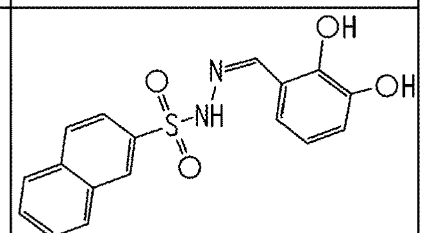 |
| U6 | CID 27518811 | ZINC 17072378 | N'-[(5-hydroxy-6-oxocyclohexa-2,4-dien-1-ylidene)methyl]-4-(2-methylpropyl)benzenesulfonohydrazide | +++ | +++ | 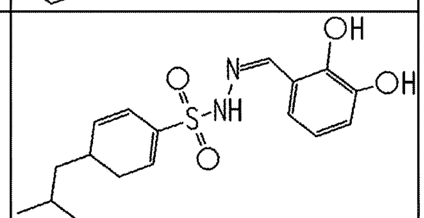 |

Class III: Based on Compound 3

| Compound identifier | Pubchem ID | ZINC ID | Chemical name | Specific effect | Off target effect | Chemical structure |
|---|---|---|---|---|---|---|
| 3 | CID 1731290 | ZINC 00974724 | 2-[(5E)-5-[(2-hydroxy-3-methoxyphenyl)methylidene]-4-oxo-2-sulfanylidene-1,3-thiazolidin-3-yl]acetate | +++ | +/− | 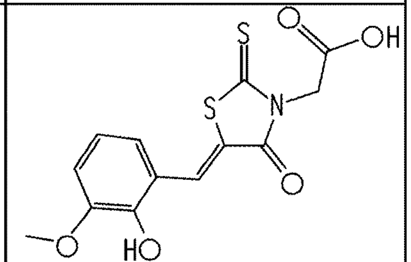 |
| 6 | CID 6993031 | ZINC 01601175 | 2-[(5Z)-4-oxo-5-(quinolin-4-ylmethylidene)-2-sulfanylidene-1,3-thiazolidin-3-yl]acetate | +/− | Irregular growth-poor solubility | 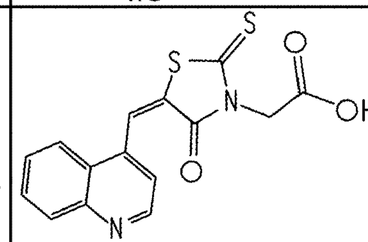 |
| U4 | CID 1369637 | ZINC 1216049 | 2-[(5Z)-5-[(3,4-dichlorophenyl)methylidene]-4-oxo-2-sulfanylidene-1,3-thiazolidin-3-yl]acetic acid | ++ | + | 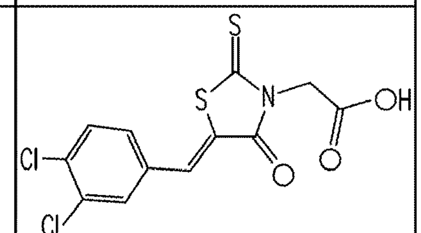 |
| U7 | CID 25846381 | ZINC 13689456 | 3-[(5E)-5-[[(2S)-2-methyl-2H-chromen-3-yl]methylidene]-2,4-dioxo-1,3-thiazolidin-3-yl]propanoic acid | ++ | +/− | 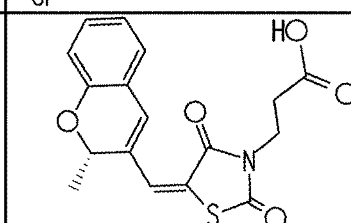 |

FIG. 11

Class IV Compounds Based on Compound 9
| Compound identifier | Pubchem ID | ZINC ID | Chemical name | Specific effect | Off target effect | Chemical structure |
|---|---|---|---|---|---|---|
| 2 | CID 40431819 | ZINC 00124050 | (2S)-3-(1H-indol-3-yl)-2-[(4-methylbenzoyl)amino]propanoate | +/− | +/− | 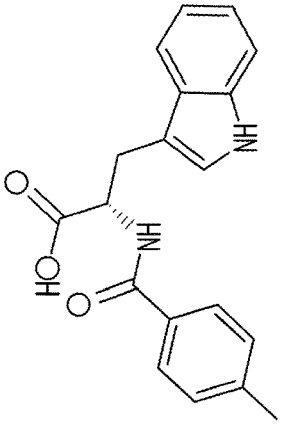 |
| 9 | CID 40446100 | ZINC 02807999 | (2S)-2-[(2,4-difluorobenzoyl)amino]-3-(1H-indol-3-yl)propanoate | + | +/− | 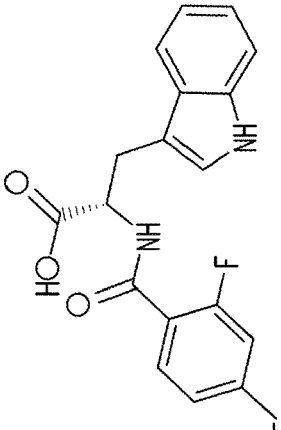 |
FIG. 13

RATIONAL DRUG DESIGN TARGETING RESISTANT GRAM-NEGATIVE BACTERIAL INFECTIONS TO POLYMYXIN-CLASS ANTIBIOTICS

CROSS-REFERENCE TO RELATED PATENT APPLICATIONS

This is a U.S. National Phase Application under 35 U.S.C. § 371 of International Patent Application No. PCT/US2016/061906, filed Nov. 14, 2016, and claims priority to U.S. Provisional Application Ser. No. 62/254,481, filed Nov. 12, 2015, which is incorporated by reference in its entirety. The International Application was published on May 18, 2017 as International Publication No. WO 2017/083859 A1.

STATEMENT OF GOVERNMENT SUPPORT

This invention was made with government support under grant numbers: NIH-GM095315 and GM111980 awarded by the National Institutes of Health. The government has certain rights in this invention.

FIELD OF THE INVENTION

The present invention relates to identification of inhibitors or antagonists of aminoarabinase glycosyltransferase (ArnT) and their use in methods of treatment or prevention of drug resistant gram negative infections, or inhibiting the growth of gram negative bacterial infections resistant to polymyxin-class antibiotics. In certain aspects, the inhibitors or antagonists can be administered in combination with one or more antibacterial agents.

BACKGROUND OF THE INVENTION

The World Health Organization has identified antibiotic resistance as one the three greatest threats to human health and emphasized that it is no longer a concern just for the future, but a present and rapidly growing global health challenge that puts our ability to treat even common infections at risk [A1, A2]. The Centers for Disease Control and Prevention estimates that antibiotic-resistant bacteria already cause serious infections in 2 million Americans each year, killing 23,000 as a result [A3]. Meanwhile, since the 1980's, there has been a marked decline in the discovery of novel antibiotics, and lean pipelines announce very few new ones for the years to come [A4]. The situation is particularly critical with the emergence of many multi-drug resistant (MDR) Gram-negative (GN) strains of pathogens, including Klebsiella, Acinetobacter, Pseudomonas aeruginosa, Enterobacter (notably Salmonella), and E. coli, which are responsible for increasingly resistant nosocomial and non-nosoconmial infections [A5-A8]. Critically, MDR GN pathogens are now evolving to pan-drug resistance (diminished susceptibility to all classes of antimicrobials) [A9]. This situation, as emphasized by the Infectious Diseases Society of America, points to the dire need for new therapeutic options specifically against MDR GN bacteria [A10].

Polymyxins are last resort antibiotics that have seen a recent revival to combat multidrug-resistant infections by Grain-negative bacteria (A1. A2). They are thought to act by permeabilizing the membranes of Gram-negative bacteria, after binding to lipopolysaccharide (LPS) in the outer membrane. This association is achieved primarily through electrostatic interactions between amino groups of polymyxins and negatively-charged moieties of the backbone glucosamine and Kdo sugars of lipid A, an amphipathic saccharolipid that anchors LPS within the outer leaflet of the outer membrane (A3). Resistance to this class of antibiotics develops through active modification of lipid A, resulting in capping of the glucosamine sugar phosphates leading to the reduction of negative membrane charge (A4). This process is also relevant for the evasion tactics used by Gram-negative bacteria to counter naturally occurring cationic antimicrobial peptides (A5, A6). There are currently no drugs available for treatment polymyxin resistant bacterial infections. Thus, there is a need for new therapeutic options specifically against MDR GN bacteria and for screening methods for identifying and designing such compounds.

SUMMARY OF THE INVENTION

In certain embodiments, the results described herein will enable the generation of compound(s) able to prevent or reverse resistance to polymyxins, and in certain embodiments could be administered as a co-drug together with one or additional antibiotic agents or compounds.

In certain embodiments, the present invention relates to a method of treating, preventing, reverting, or inhibiting a drug resistant gram negative infection in a patient, comprising administering to the patient an effective amount of a compound having the formula according to:

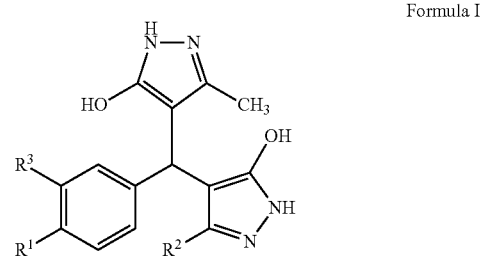

Formula I wherein:

$R^1$ is selected from chloro, fluoro, OH, straight and branched alkyl of 1 to 6 carbon atoms with 1 to 3 carbon atoms preferred and dialkylamino of the formula —$NR^3R^4$ where $R^3$ and $R^4$ are independently selected from hydrogen, straight and branched alkyl of 1 to 6 carbon atoms with 1 to 3 carbon atoms preferred;

$R^2$ is straight and branched alkyl of 1 to 3 carbon atoms;

$R^3$ is H, straight and branched alkyl of 1 to 3 carbon atoms, OH and nitro.

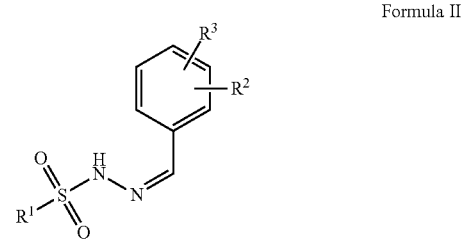

Formula II wherein:
R¹ is a moiety selected from the group:

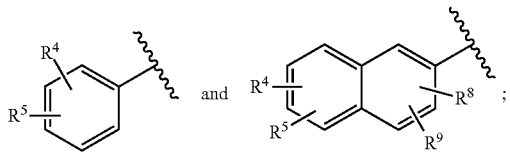

R², R³, R⁴, R⁵, R⁸ and R⁹ are independently selected from hydrogen, hydroxyl, amino, fluoro, chloro, straight chain alkyl of 1 to 6 carbon atoms, branched chain alkyl of 3 to 7 carbon atoms, nitro and —NR⁶R⁷ where R⁶ and R⁷ are independently selected from hydrogen, straight and branched alkyl of 1 to 6 carbon atoms with 1 to 3 carbon atoms preferred;

Formula III

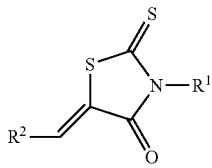

wherein:
R¹ is a moiety —(CH₂)n-COOH;
n is 1 to 3;
R² is selected from moieties of the group

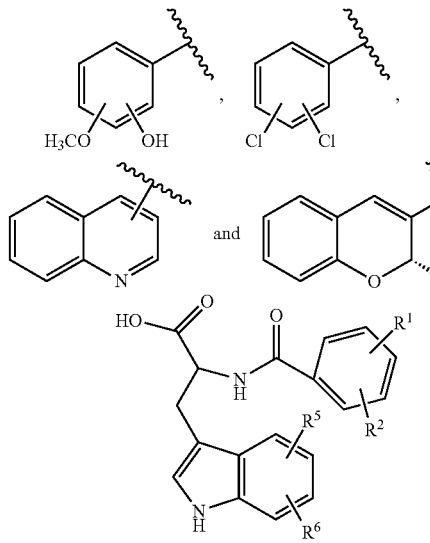

wherein:
R¹ and R² and R⁵ and R⁶ are independently selected from hydrogen, fluoro, chloro, straight chain alkyl of 1 to 6 carbon atoms, branched chain alkyl of 3 to 7 carbon atoms and —NR³R⁴ where R³ and R⁴ are independently selected from hydrogen, and straight and branched alkyl of 1 to 6 carbon atoms;
or any combination thereof, or a pharmaceutically acceptable salt, solvate, poly-morph, tautomer or prodrug thereof.

In certain embodiments, the present invention relates to a method for increasing susceptibility of at least one drug resistant gram negative organism to polymyxin class antibiotics, comprising contacting the at least one gram negative bacteria with an effective amount of a compound having the formula according to:

Formula I

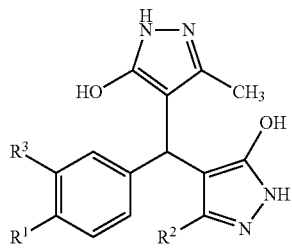

wherein:
R¹ is selected from chloro, fluoro. OH, straight and branched alkyl of 1 to 6 carbon atoms with 1 to 3 carbon atoms preferred and dialkylamino of the formula —NR³R⁴ where R³ and R⁴ are independently selected from hydrogen, straight and branched alkyl of 1 to 6 carbon atoms with 1 to 3 carbon atoms preferred;
R² is straight and branched alkyl of 1 to 3 carbon atoms;
R³ is H, straight and branched alkyl of 1 to 3 carbon atoms. OH and nitro;

Formula II

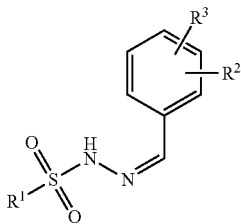

wherein:
R¹ is a moiety selected from the group:

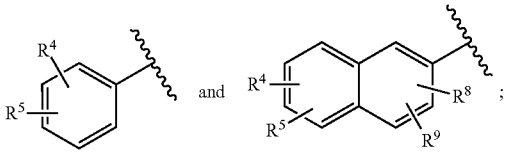

R², R³, R⁴, R⁵, R⁸ and R⁹ are independently selected from hydrogen, hydroxyl, amino, fluoro, chloro, straight chain alkyl of 1 to 6 carbon atoms, branched chain alkyl of 3 to 7 carbon atoms, nitro and —NR⁶R⁷ where R⁶ and R⁷ are independently selected from hydrogen, straight and branched alkyl of 1 to 6 carbon atoms with 1 to 3 carbon atoms preferred;

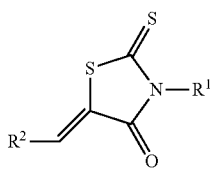

Formula III wherein:
R$^1$ is a moiety —(CH$_2$)n-COOH;
 n is 1 to 3:
R$^2$ is selected from moieties of the group

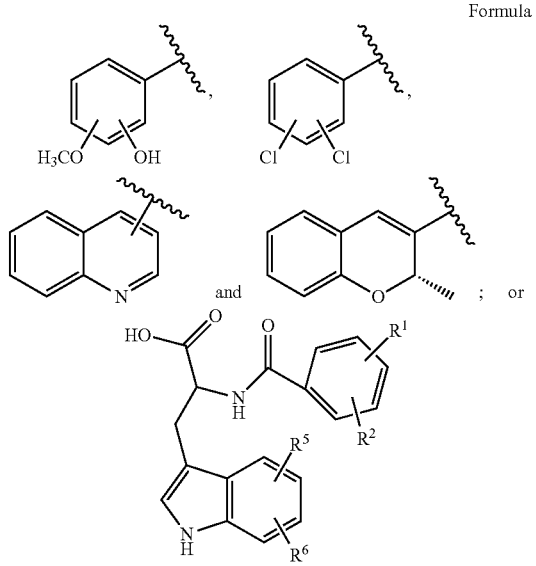

Formula IV wherein:
R$^1$ and R$^2$ and R$^5$ and R$^6$ are independently selected from hydrogen, fluoro, chloro, straight chain alkyl of 1 to 6 carbon atoms, branched chain alkyl of 3 to 7 carbon atoms and —NR$^3$R$^4$ where R$^3$ and R$^4$ are independently selected from hydrogen, and straight and branched alkyl of 1 to 6 carbon atoms;
or any combination thereof, or a pharmaceutically acceptable salt, solvate, poly-morph, tautomer or prodrug thereof.

In certain embodiments, the present invention relates to a method for inhibiting aminoarabinase glycosyltransferase (ArnT) of a gram negative bacterial species, comprising: contacting the bacteria with compound having the formula according to:

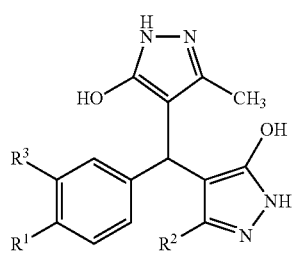

Formula I

Wherein:
R$^1$ is selected from chloro, fluoro, OH, straight and branched alkyl of 1 to 6 carbon atoms with 1 to 3 carbon atoms preferred and dialkylamino of the formula —NR$^3$R$^4$ where R$^3$ and R$^4$ are independently selected from hydrogen, straight and branched alkyl of 1 to 6 carbon atoms with 1 to 3 carbon atoms preferred;
R$^2$ is straight and branched alkyl of 1 to 3 carbon atoms;
R$^3$ is H, straight and branched alkyl of 1 to 3 carbon atoms, OH and nitro:

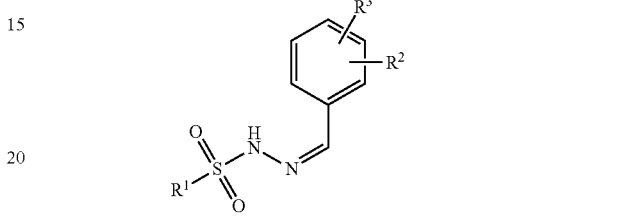

Formula II wherein:
R$^1$ is a moiety selected from the group:

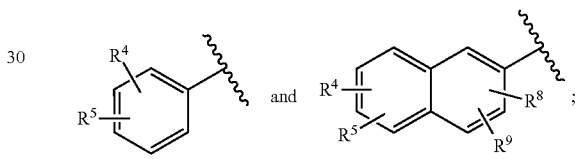

R$^2$, R$^3$, R$^4$, R$^5$, R$^8$ and R$^9$ are independently selected from hydrogen, hydroxyl, amino, fluoro, chloro, straight chain alkyl of 1 to 6 carbon atoms, branched chain alkyl of 3 to 7 carbon atoms, nitro and —NR$^6$R$^7$ where R and R$^7$ are independently selected from hydrogen, straight and branched alkyl of 1 to 6 carbon atoms with 1 to 3 carbon atoms preferred;

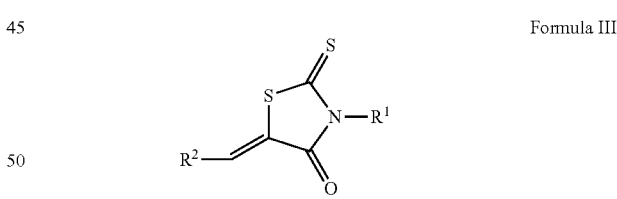

Formula III wherein:
R$^1$ is a moiety —(CH$_2$)n-COOH;
 n is 1 to 3;
R$^2$ is selected from moieties of the group

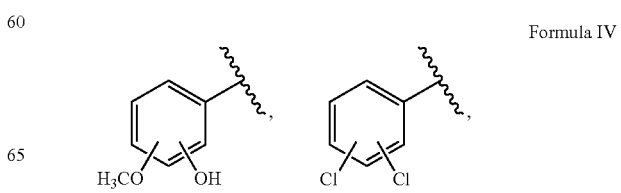

Formula IV

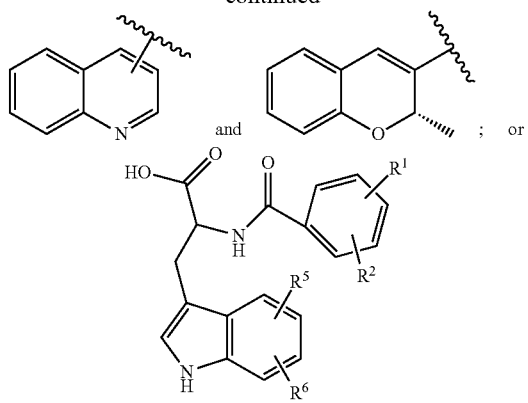

and ; or wherein:
R[1] and R[2] and R[5] and R[6] are independently selected from hydrogen, fluoro, chloro, straight chain alkyl of 1 to 6 carbon atoms, branched chain alkyl of 3 to 7 carbon atoms and —NR[3]R[4] where R[3] and R[4] are independently selected from hydrogen, and straight and branched alkyl of 1 to 6 carbon atoms;

or any combination thereof, or a pharmaceutically acceptable salt, solvate, poly-morph, tautomer or prodrug thereof, in an amount effective to block L-Ara4N binding to the ArnT active site.

In certain embodiments, the present invention relates to a compound 4,4'-[(4-chlorophenyl)methylene]bis(3-methyl-1H-pyrazol-5-ol), or a pharmaceutically acceptable salt, solvate, poly-morph, tautomer or prodrug thereof, for use as a co-drug or medicament. In certain embodiments, the medicament increases susceptibility of at least one drug resistant gram negative organism to polymyxin class antibiotics. In certain embodiments, the at least one drug resistant gram negative organism is multidrug resistant.

In certain embodiments, the present invention relates to use of a compound having the formula according to:

Formula 1

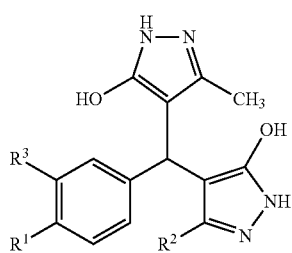

wherein:
R[1] is selected from chloro, fluoro, OH, straight and branched alkyl of 1 to 6 carbon atoms with 1 to 3 carbon atoms preferred and dialkylamino of the formula —NR[3]R[4] where R[3] and R[4] are independently selected from hydrogen, straight and branched alkyl of 1 to 6 carbon atoms with 1 to 3 carbon atoms preferred;
R[2] is straight and branched alkyl of 1 to 3 carbon atoms;
R[3] is H, straight and branched alkyl of 1 to 3 carbon atoms, OH and nitro;

Formula II

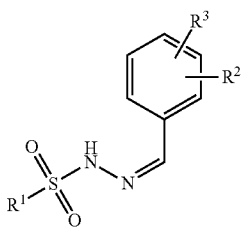

wherein:
R[1] is a moiety selected from the group:

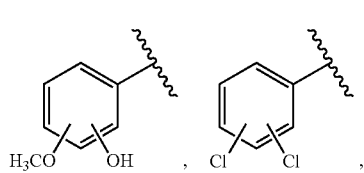

and ;

R[2], R[3], R[4], R[5], R[8] and R[9] are independently selected from hydrogen, hydroxyl, amino, fluoro, chloro, straight chain alkyl of 1 to 6 carbon atoms, branched chain alkyl of 3 to 7 carbon atoms, nitro and —NR[6]R[7] where R[6] and R[7] are independently selected from hydrogen, straight and branched alkyl of 1 to 6 carbon atoms with 1 to 3 carbon atoms preferred;

Formula III wherein:
R[1] is a moiety —(CH$_2$)n-COOH;
n is 1 to 3;
R[2] is selected from moieties of the group Formula IV

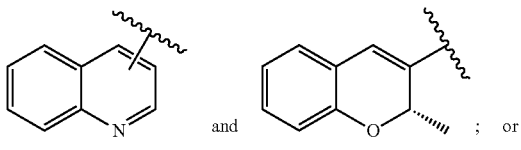

and ; or

-continued

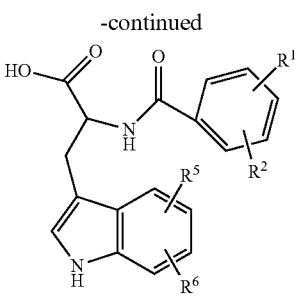

wherein:

$R^1$ and $R^2$ and $R^5$ and $R^6$ are independently selected from hydrogen, fluoro, chloro, straight chain alkyl of 1 to 6 carbon atoms, branched chain alkyl of 3 to 7 carbon atoms and —$NR^3R^4$ where $R^3$ and $R^4$ are independently selected from hydrogen, and straight and branched alkyl of 1 to 6 carbon atoms;

or any combination thereof, or a pharmaceutically acceptable salt, solvate, poly-morph, tautomer or prodrug thereof in the preparation of a pharmaceutical composition for inhibiting the growth of one or more multidrug resistant gram negative organism.

In certain embodiments, the present invention relates to use of a compound having the formula according to:

Formula I

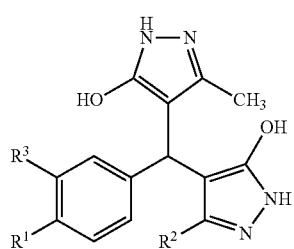

Wherein:

$R^1$ is selected from chloro, fluoro. OH, straight and branched alkyl of 1 to 6 carbon atoms with 1 to 3 carbon atoms preferred and dialkylamino of the formula —$NR^3R^4$ where $R^3$ and $R^4$ are independently selected from hydrogen, straight and branched alkyl of 1 to 6 carbon atoms with 1 to 3 carbon atoms preferred;

$R^2$ is straight and branched alkyl of 1 to 3 carbon atoms;

$R^3$ is H, straight and branched alkyl of 1 to 3 carbon atoms. OH and nitro;

Formula II

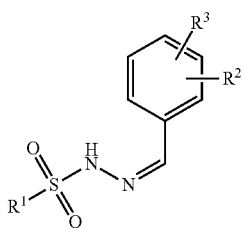

wherein:

$R^1$ is a moiety selected from the group:

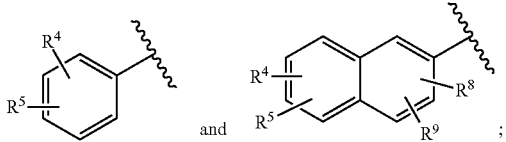

$R^2$, $R^3$, $R^4$, $R^5$, $R^8$ and $R^9$ are independently selected from hydrogen, hydroxyl, amino, fluoro, chloro, straight chain alkyl of 1 to 6 carbon atoms, branched chain alkyl of 3 to 7 carbon atoms, nitro and —$NR^6R^7$ where R and $R^7$ are independently selected from hydrogen, straight and branched alkyl of 1 to 6 carbon atoms with 1 to 3 carbon atoms preferred;

Formula III

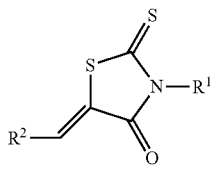

wherein:

$R^1$ is a moiety —$(CH_2)n$-COOH;
n is 1 to 3;
$R^2$ is selected from moieties of the group Formula IV

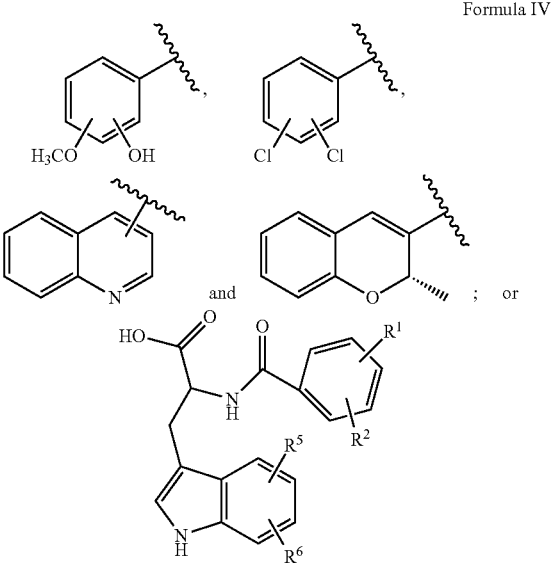

wherein:

$R^1$ and $R^2$ and $R^5$ and $R^6$ are independently selected from hydrogen, fluoro, chloro, straight chain alkyl of 1 to 6 carbon atoms, branched chain alkyl of 3 to 7 carbon atoms and —$NR^3R^4$ where $R^3$ and $R^4$ are independently selected from hydrogen, and straight and branched alkyl of 1 to 6 carbon atoms;

or any combination thereof, or a pharmaceutically acceptable salt, solvate, poly-morph, tautomer or prodrug thereof in the preparation of a pharmaceutical composition for the treatment or prophylaxis of a disorder or disease mediated by infection with at least one gram negative organism.

In certain embodiments, the present invention relates to a method of the treatment or prophylaxis of a disorder or disease mediated by infection with at least one gram negative organism, comprising administering to a patient in need thereof a therapeutically effective amount of a compound having the formula according to:

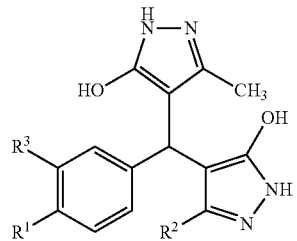

Formula I wherein:
$R^1$ is selected from chloro, fluoro, OH, straight and branched alkyl of 1 to 6 carbon atoms with 1 to 3 carbon atoms preferred and dialkylamino of the formula —$NR^3R^4$ where $R^3$ and $R^4$ are independently selected from hydrogen, straight and branched alkyl of 1 to 6 carbon atoms with 1 to 3 carbon atoms preferred;
$R^2$ is straight and branched alkyl of 1 to 3 carbon atoms;
$R^3$ is H, straight and branched alkyl of 1 to 3 carbon atoms, OH and nitro.

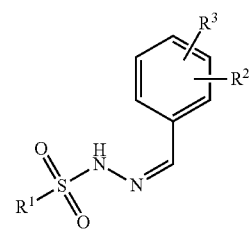

Formula II wherein:
$R^1$ is a moiety selected from the group:

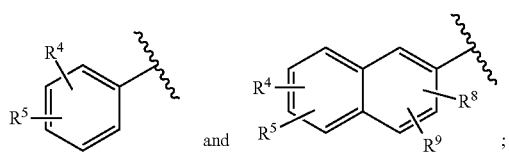

$R^2$, $R^3$, $R^4$, $R^5$, $R^8$ and $R^9$ are independently selected from hydrogen, hydroxyl, amino, fluoro, chloro, straight chain alkyl of 1 to 6 carbon atoms, branched chain alkyl of 3 to 7 carbon atoms, nitro and —$NR^6R^7$ where $R^6$ and $R^7$ are independently selected from hydrogen, straight and branched alkyl of 1 to 6 carbon atoms with 1 to 3 carbon atoms preferred;

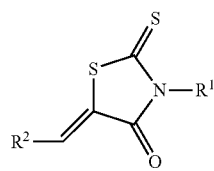

Formula III wherein:
$R^1$ is a moiety —$(CH_2)n$-COOH;
n is 1 to 3;
$R^2$ is selected from moieties of the group

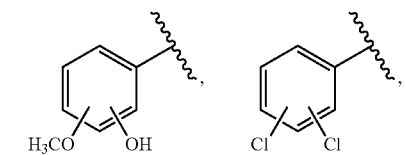

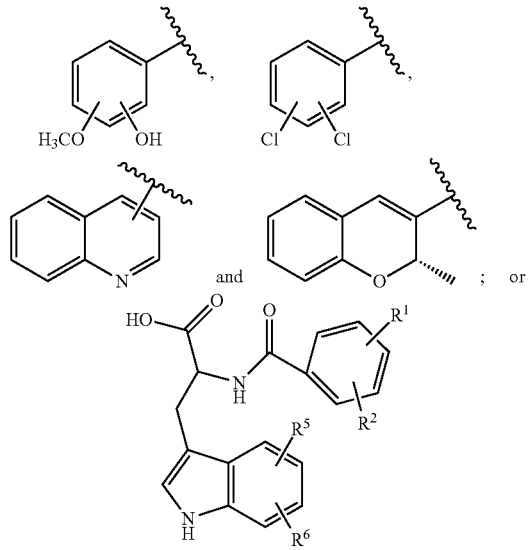

Formula IV wherein:
$R^1$ and $R^2$ and $R^5$ and $R^6$ are independently selected from hydrogen, fluoro, chloro, straight chain alkyl of 1 to 6 carbon atoms, branched chain alkyl of 3 to 7 carbon atoms and —$NR^3R^4$ where $R^3$ and $R^4$ are independently selected from hydrogen, and straight and branched alkyl of 1 to 6 carbon atoms;
or any combination thereof, or a pharmaceutically acceptable salt, solvate, poly-morph, tautomer or prodrug thereof, in combination with at least one additional antibacterial agent or compound.

In certain embodiments, the compound comprises:
4-[(4-chlorophenyl)-(3-methyl-5-oxo-1,2-dihydropyrazol-4-yl)methyl]-5-methyl-1,2-dihydropyrazol-3-one;
5-methyl-4-[(3-methyl-5-oxo-1,2-dihydropyrazol-4-yl)-(4-propan-2-ylphenyl)methyl]-1,2-dihydropyrazol-3-one;
4-[[4-(dimethylamino)phenyl]-(3-methyl-5-oxo-1,2-dihydropyrazol-4-yl)methyl]-5-methyl-1,2-dihydropyrazol-3-one; 4-[(S)-(3,4-dihydroxyphenyl)-(3-methyl-5-oxo-1,2-dihydropyrazol-4-yl)methyl]-5-methyl-1H-pyrazol-3-olate; 4-[(4-hydroxy-3-nitrophenyl)-(3-methyl-5-oxo-1,2-dihydropyrazol-4-yl)methyl]-5-methyl-1,2-dihydropyrazol-3-one;
N'-[(3-hydroxy-4-oxocyclohexa-2,5-dien-1-ylidene)methyl]-4-propylbenzenesulfonohydrazide; N'-[(3-hydroxy-4-oxocyclohexa-2,5-dien-1-ylidene)methyl]-4-(2-methylpropyl)benzenesulfonohydrazide; N'-[(5-hydroxy-6-oxocyclohexa-2,4-dien-1-ylidene)methyl]naphthalene- 2-sulfonohydrazide N'-[(5-hydroxy-6-oxocyclohexa-2,4-dien-1-ylidene)methyl]-4-(2-methylpropyl)benzenesulfonohydrazide: 2-[(5E)-5-[(2-hydroxy-3-methoxyphenyl)methylidene]-4-oxo-2-sulfanylidene-1,3-thiazolidin-3-yl]acetate; 2-[(5Z)-4-oxo-5-(quinolin-4-ylmethylidene)-2-sulfanylidene-1,3-thiazolidin-3-yl]acetate; 2-[(5Z)-5-[(3,4-dichlorophenyl)methylidene]-4-oxo-2-sulfanylidene-1,3-thiazolidin-3-yl]acetic acid; 3-[(5E)-5-[[(2S)-2-methyl-2H-chromen-3-yl]methylidene]-2,4-dioxo-1,3-thiazolidin-3-yl]propanoic acid; (2S)-3-(1H-indol-3-yl)-2-[(4-methylbenzoyl)amino]propanoate; (2S)-2-[(2,4-difluorobenzoyl)amino]-3-(1H-indol-3-yl)propanoate; or combinations thereof.

In certain embodiments, the compound further comprises at least one additional antibacterial agent or compound.

In certain embodiments, the method further comprises administering at least one additional antibacterial agent. In additional embodiments, the at least one additional antibacterial agent comprises a polymyxin class antibiotic. In additional embodiments, the polymyxin is Polymyxin B or Polymyxin E. In additional embodiments, the gram negative infection is caused by one or more bacteria from the class Enterobacteriaceae or Gammaproteobacteria. In additional embodiments the Enterobacteriaceae comprises one or more organisms from the genus *Salmonella, Escherichia, Yersinia, Klebsiella, Shigella, Proteus, Enterobacter, Serratia*, or *Citrobacter*. In yet additional embodiments, the genus is at least one species comprising: *Escherichia coli, Klebsiella pneumoniae, Proteus vulgaris, Salmnonella typhimurium*, and *Serratia marcescens*. In additional embodiments, the gammaproteobacteria comprises one or more organisms from the genus *Acinetobacter* or *Pseudomonas*. In additional embodiments, the genus comprises at least one species comprising: *A. baumannii* or *P. aeruginosa*.

In additional embodiments, the patient is a mammal. In additional embodiments, the method further comprises administering a pharmaceutically effective amount of the compound.

In certain embodiments, the invention relates to a method for screening/identifying a compound capable of increasing susceptibility of at least one multidrug resistant gram negative organism to polymyxin class antibiotics comprising: identifying a compound as a structural homolog or analog of L-Ara4N and testing the compound for the ability to restore sensitivity of the at least one gram negative organism to polymyxin, and selecting as a positive compound one that increases susceptibility of the organism to polymyxin.

BRIEF DESCRIPTION OF THE DRAWINGS

FIGS. 1A-B is a schematic illustrating that ArnT is a key target for resistance to polymyxins showing the reaction catalyzed by ArnT. The sugar 4-Amino-4-deoxy-L-arabinose (L-Ara4N) is transferred from the carrier undecaprenyl phosphate (UndP) to lipid A. 1 and 4' phosphate positions on lipid A are marked.

FIG. 2A shows negative ion MALDI-TOF spectrometry of lipid A purified from *E. coli* WD101 ΔarnTΔeptA strain expressing ArnTCm. The major peak at 1928.0 corresponds to lipid A modified with L-Ara4N added at either the 4' (shown on the left, in red) or 1 (shown on the right, in red) acceptor position. The secondary peak at 1797.0 corresponds to bisphosphorylated hexa-acylated lipid A. FIG. 2B is a bar graph showing the effect of introduction of ArnTSt and ArnTCm into the BL21 (DE3)ΔarnT knockout *E. coli* strain. Only ArnTSt is able to rescue polymyxin resistance. ArnTCm was expressed here using the pMCSG7 vector, and not pNYCOMPS-Nterm used for crystallography-related protein production, because of matching antibiotic resistance of the former vector with pET21 used for ArnTSt expression. FIG. 2C is a table showing minimal inhibitory concentration of polymyxin B (PMXB) in WD101 strain (PMXB-resistant) and ΔarnTΔeptA double-mutant (PMXB sensitive). Expression of ArnTCm in ΔarnTΔeptA does not rescue resistance to PMXB. FIG. 2D is a blot showing expanded analysis of $^{32}$P-labeled lipid A by thin-layer chromatography (TLC). Lipid A in W3110 strain carries only a pyrophosphate modification (1-PP) and is sensitive to polymyxin B (PMXB). WD101 produces doublemodified lipid A with Ara4N and phosphoethanolamine (pEtN). In the absence of both arnT and eptA (a gene required for the addition of phosphoethanolamine to the 1 phosphate group of lipid A), ArnTSt adds L-Ara4N to both the 1 and 4' phosphates, leading to both single- and double-modified lipid A spots (double-modified L-Ara4N lipid A indicated by red arrow). In contrast, ArnTCm only yields a single modified lipid A species. Moreover, in a ΔarnT single knockout strain, ArnTCm is unable to modify lipid A. The conclusion is that ArnTCm is stereospecific for the 1 phosphate group of lipid A. Pre-induction with PMXB (0.1 μg/mL) did not significantly change the amount and/or character of lipid A modification.

FIGS. 3A-B show the first atomic-level structureses of ArnT from *Cupravidius metallidurans*. FIG. 3A shows an overview of the ArnTCm structure with no ligand bound (apo, FIG. 3A) and bound to UndP, FIG. 3B. PD and TMD denote the periplasmic and the transmembrane domains respectively. Cavities for the binding of lipid A and the UndP carrier are indicated with dashed lines and differential shading. The L-Ara4N pocket located at the junction of the two cavities is circled by a dashed line.

FIG. 4C shows the result of in silico docking of L-Ara4N sugar in the putative L-Ara4N binding pocket.

FIG. 5A is a schematic representation of substrate-binding induced conformational changes and catalytic cycle of ArnTCm. FIG. 5B shows the structural perspective of the active site of ArnTCm. A putative position for the aminoarabinose sugar determined by docking is shown. The conserved D55 and D158 are located between the binding site for UndP/L-Ara4N and cavity 1, and their distance is shown. P1 (magenta) is the phosphate of experimentally determined UndP, whilst P2 (heteroatom) is the phosphate from the modeled L-Ara4N-phosphate. Residues 274-278 were removed from the model to obtain a clear view of the active site. FIG. 5C shows functional significance of D32 and K180 for ArnTSt. The function was tested utilizing the polymyxin B (PMXB) growth assay. FIG. 5D illustrates putative catalytic mechanisms in which the acceptor phosphate from lipid A is coordinated by D55 and D158, and performs the direct nucleophilic attack on the Cl atom of the arabinose ring.

FIG. 6A shows growth of *E. coli* BL21 strain in the presence and absence of polymyxin B (PMXB). *E. coli* BL21 is inherently resistant to polymyxin B as it carries the endogenous *E. coli* ArnT gene. *E. coli*

BL21 strain is used to test efficacy of tested compounds towards the E. coli ArnT protein. FIG. 6B shows growth of E. coli BL21 ΔArnT strain in the presence and absence of polymyxin B (PMXB). In E. coli BL21 ΔArnT the endogenous E. coli ArnT gene has been deleted, thus rendering the E. coli BL21 ΔArnT strain sensitive to polymyxin B (leading to absence of growth in the presence of PMXB). FIG. 6C shows growth of Gi24 strain in the presence and absence of PMXB. Gi24 is E. coli BL21 ΔArnT that has been transformed with the plasmid pGi24 that expresses the wt Salmonella typhimurium ArnT. Expression of wt Salmonella typhimurium ArnT restores resistance to polymyxin B demonstrated by growth of Gi24 strain in the presence of PMXB. The Gi24 strain is used to test efficacy of tested compounds towards the Salmonella typhimurium ArnT protein.

FIGS. 7A-B are Tables describing the five Class I compounds and their chemical names, reference/source information, summaries of effects, and chemical structures. A qualitative assessment of observed effects is provided using the following system: +,++,+++ describes positive effects (with an estimation of the severity of observed effects given with the number of plus signs), +/− describes small effects or lack of an effect, yet presence of an effect cannot be completely ruled out, and − describes complete absence of an effect.

FIG. 9 is a Table describing the four Class II compounds and their chemical names, reference/source information, summaries of effects, and structures. The scoring system follows the definitions described in FIG. 7A-B.

FIG. 11 is a Table describing the four Class III compounds and their chemical names, reference/source information, summaries of effects, and structures. The scoring system follows the definitions described in FIG. 7A-B.

FIG. 13 is a Table describing the two Class IV compounds and their chemical names, reference/source information, summaries of effects, and structures. The scoring system follows the definitions described in FIG. 7A-B.

DETAILED DESCRIPTION OF THE INVENTION

In certain aspects, crystal structures of ArnT from C. metallidurans will be used in combination with genetic and functional analysis to perform rational drug-design for development of co-drugs to prevent or reverse resistance to polymyxin-class antibiotics. The present results describe developing ArnT as a drug target for a new class of antibiotics to counter resistance to polymyxins. Towards this end, the mechanism of Lipid A glycosylation by ArnT in Salmonella enterica and Escherichia coli at the molecular level will be elucidated as described herein, which then will be utilized for structure-guided drug discovery and design to identify small molecules that can remedy resistance to polymyxins. The first structure of ArnT from Cupriavidus metallidurans CH34, has been determined both in its apo and substrate-bound state, which provides a unique tool for developing ArnT as a drug target for a new class of antibiotics to counter resistance to polymyxins.

While not being bound by theory, the present invention is based in part on the determination of the first high-resolution structures of aminoarabinose glycosyltransferase (ArnT), and in particular to structures corresponding to two different states of the aminoarabinose glycosyltransferase (ArnT) from *Cupriavidus metallidurans* CH34, a Gram-negative bacterium. ArnT is the enzyme in gram negative bacteria that attaches aminoarabinose to Lipid A on the bacterial outer membrane, thus reducing the negative charge of the membrane and disrupting binding of the cationic polymyxin antibiotics. As the last enzyme in the aminoarabinose biosynthetic pathway of Gram-negative bacteria, ArnT is a useful target for designing small molecules to disrupt its function and ultimately prevent or reverse polymyxin resistance. As described herein, the apo and lipid-carrier bound structures of ArnT can serve as templates for rational drug design to target ArnT. In certain embodiments, the present invention relates to a process for high throughput screening of a large number of compounds for drugs that may act as antagonists or competitive antagonists for ArnT in Gram-negative bacteria.

Figure 1A:
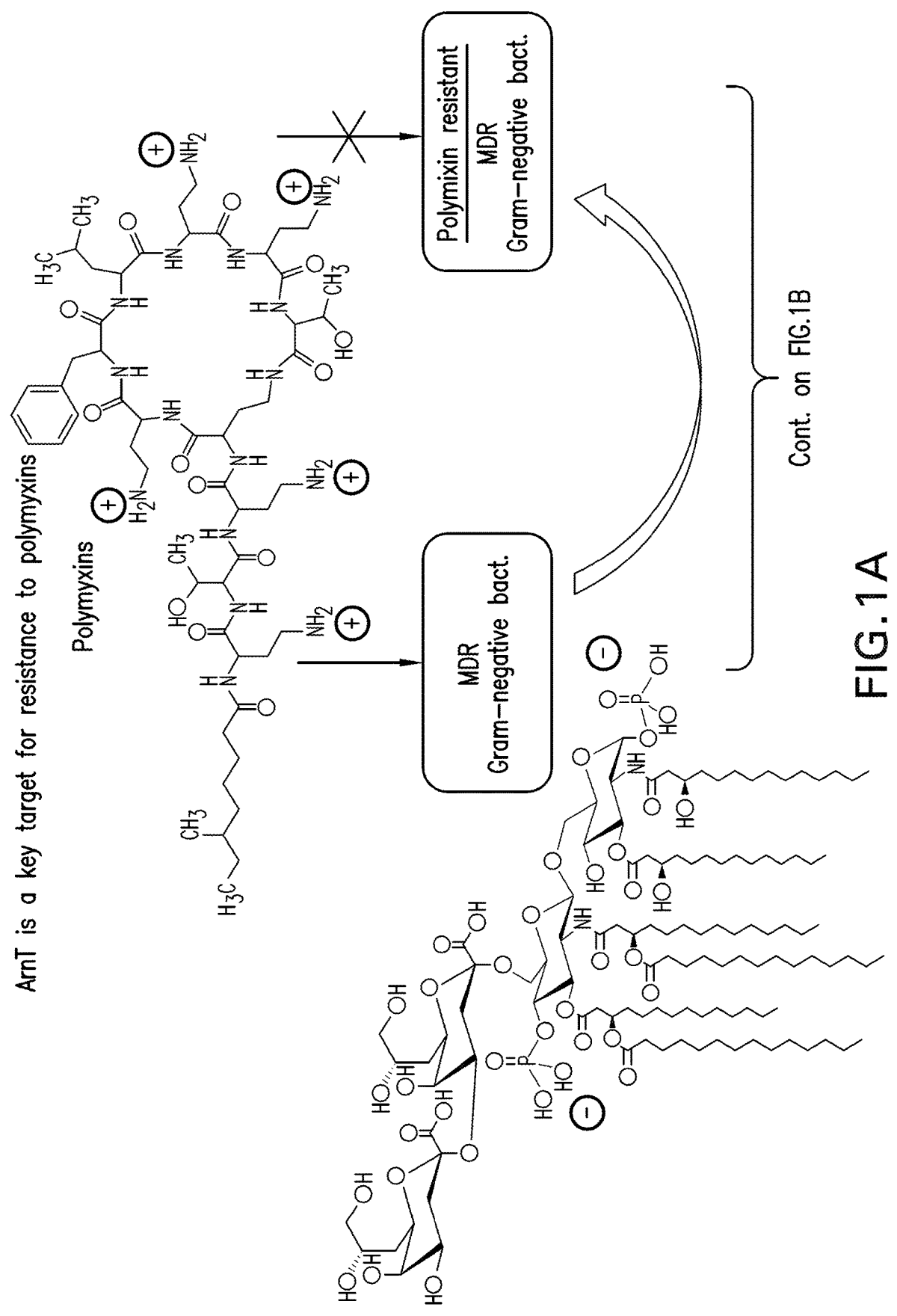
Figure 1B:
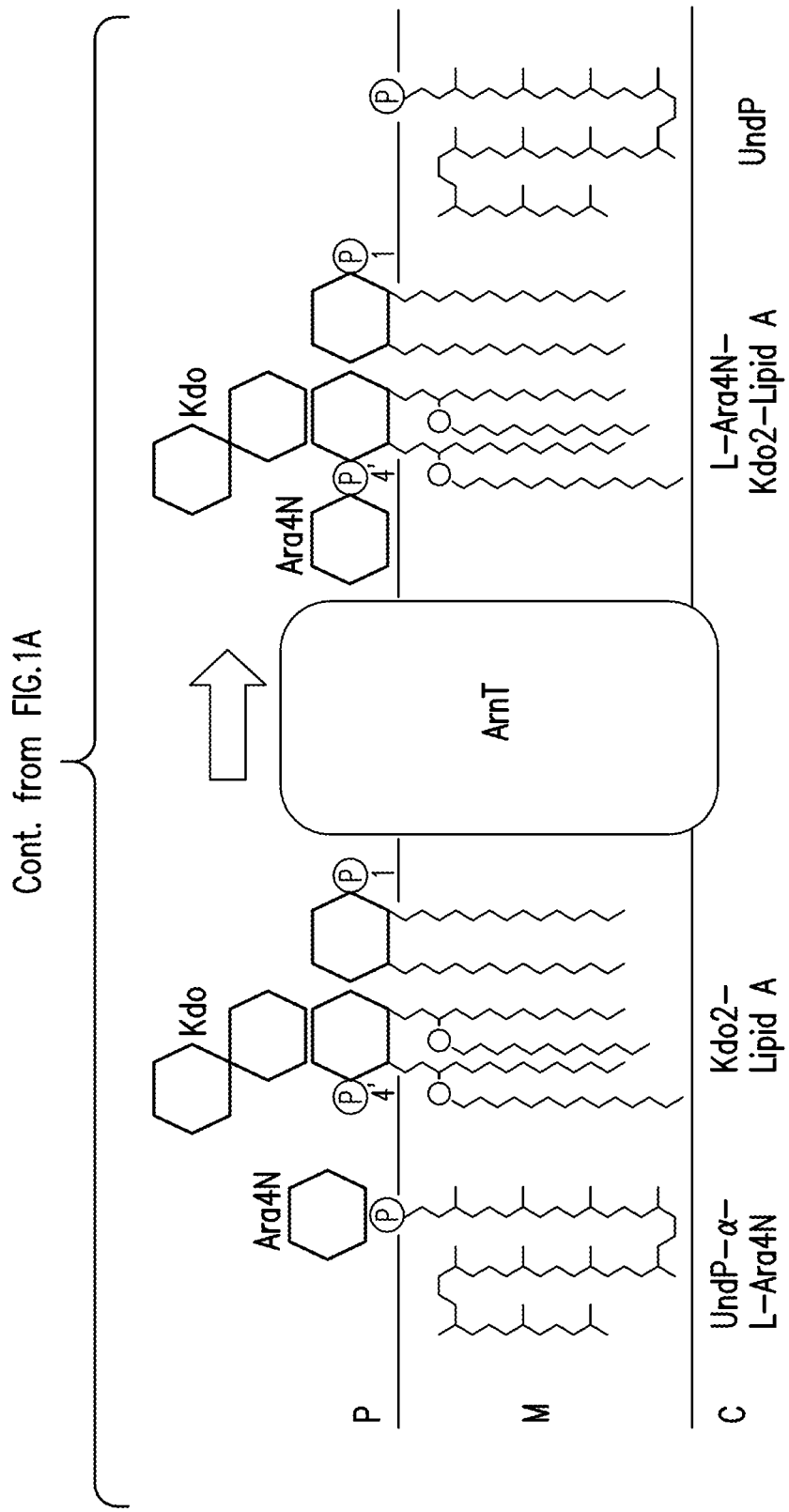
Figure 4A:
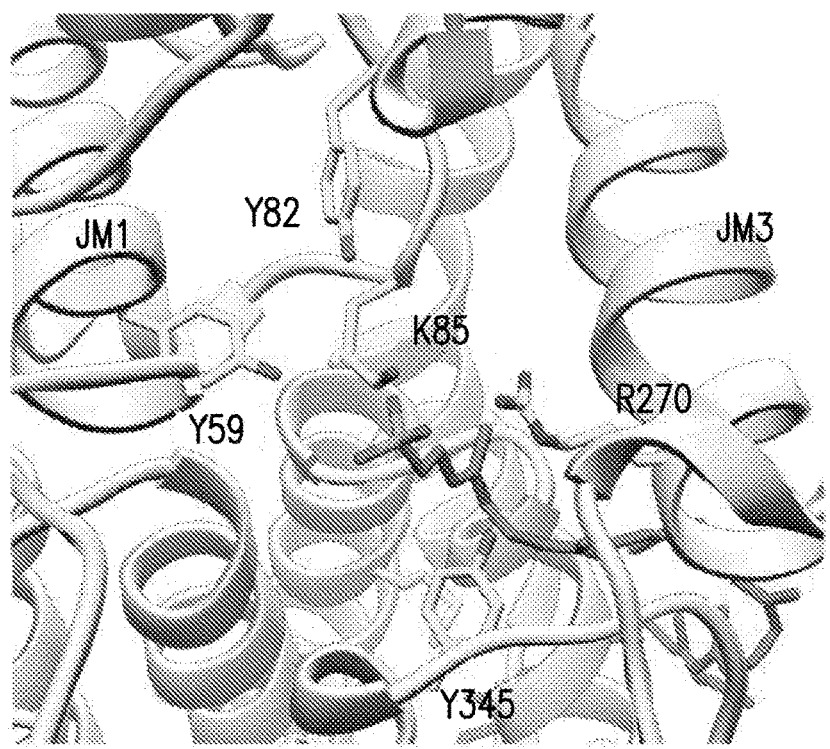
FIGS. 4A-C are ribbon diagrams (FIG. 4A and FIG. 4C, and a graph (FIG. 4B) showing functional significance of residues around the headgroup of UndP, tested utilizing a polymyxin B (PMXB) growth assay.

Polymyxins are a last-line of treatment for MDR Gram-negative infections. Increasingly, clinicians worldwide are confronted by the reality of infections with GN pathogens that are resistant to all available antibiotics except polymyxins [A11, A12]. Two polymyxins have become available for clinical use in the 1960s: polymyxin B and polymyxin E (i.e., colistin). They have a narrow antibacterial spectrum, mainly against GN bacteria, and are efficient against most current MDR GN pathogens [A13, A14]. However, the clinical use of polymyxins waned in the 1970s due to reports of nephrotoxicity and neurotoxicity after intravenous administration [A13, A14]. The rapid increase of resistance against all other classes of antibiotics has necessitated their resurgence, and they are currently widely used as a last resort treatment for MDR GN infections. Polymyxins are nonribosomal lipopeptides that are polycationic at physiological pH (FIG. 1A). Mechanisms of action of polymyxin B on Gram negative bacteria are shown in FIG. 1C and FIG. 4A. Positively charged amino groups are shown with + symbols. FIG. 1B shows Lipid A from *E. coli*. Negatively charged phosphate groups are shown by dashes (-). FIG. 1C is a schematic representation of mechanisms of action of polymyxins, acting on the membrane of Gram-negative bacteria. Two mechanisms are illustrated: membrane lysis (1) and vesicle-vesicle contact (II). Positive and negative charges from polymyxin and lipid A respectively, are indicated. OM, IM and P denote the outer, the inner membrane and the periplasm. (A18).

Polymyxins primarily act by permeabilizing GN bacterial membranes [A15], although a different mechanism proceeding through lipid exchange between the outer and inner membrane has also been proposed [A16-A18]. In between the cationic amino groups of polymyxins and anionic phosphate groups on lipid A, the amphipathic saccharolipid that anchors LPS within the outer leaflet of the outer membrane (FIGS. 1A-B) [A19]. Critically, resistance to polyxymins can emerge spontaneously in vitro [A20-A22] and has been observed in patients in case of suboptimal use [A10, A23]. This resistance is mainly acquired through enzymatic modifications of lipid A that cap the glucosamine sugar phosphates and results in a reduction of the negative charges on the bacteria membrane [A24]. This mechanism is also an evasion tactic of GN bacteria effective against naturally produced antimicrobial cationic peptides [A25, A26]. While the incidence of resistance to polymyxin is still limited, a worrying trend toward greater resistance is observed worldwide and threatens our ability to combat MDR GN infections [A27]. As described herein, this mechanism of acquisition of polymyxin resistance is an attractive target for the development of drugs able to restore susceptibility to polymyxins.

It is expected that the compounds and strategies to treat, prevent, revert, or inhibit drug resistant gram negative infections, as described herein, will be broadly applicable to MDR GN infections, exemplified although not limited to, some the organisms listed below.

*Acinetobacter* is a genus of Gram-negative bacteria belonging to the wider class of Gammaproteobacteria. In healthy individuals, *Acinetobacter* colonies on the skin correlate with low incidence of allergies. *Acinetobacter* is thought to be allergy-protective. *A. baumannii* is the second most commonly isolated nonfermenting bacterium in humans. In immunocompromised individuals, several *Acinetobacter* species can cause life-threatening infections. Such species also exhibit a relatively broad degree of antibiotic resistance.

*Acinetobacter* is frequently isolated in nosocomial infections, and is especially prevalent in intensive care units, where both sporadic cases and epidemic and endemic occurrences are common. *A. baumannii* is a frequent cause of nosocomial pneumonia, especially of 'late-onset' ventilator-associated pneumonia. It can cause various other infections, including skin and wound infections, bacteremia, and meningitis, but *A. lwoffi* is mostly responsible for the latter. *A. baumannii* can survive on the human skin or dry surfaces for weeks.

*Pseudomonas* is a genus of Gram-negative, aerobic gammaproteobacteria, belonging to the family Pseudomonadaceae containing 191 validly described species. The members of the genus demonstrate a great deal of metabolic diversity, and consequently are able to colonize a wide range of niches. Their ease of culture in vitro and availability of an increasing number of *Pseudomonas* strain genome sequences has made the genus an excellent focus for scientific research; the best studied species include *P. aeruginosa* in its role as an opportunistic human pathogen.

Being Gram-negative bacteria, most *Pseudomonas* spp. are naturally resistant to penicillin and the majority of related beta-lactam antibiotics, but a number are sensitive to piperacillin, imipenem, ticarcillin, or ciprofloxacin. Aminoglycosides such as tobramycin, gentamicin, and amikacin are other choices for therapy. This ability to thrive in harsh conditions is a result of their hardy cell walls that contain porins. Their resistance to most antibiotics is attributed to efflux pumps, which pump out some antibiotics before they are able to act.

*Pseudomonas aeruginosa* is increasingly recognized as an emerging opportunistic pathogen of clinical relevance. One of its most worrying characteristics is its low antibiotic susceptibility. This low susceptibility is attributable to a concerted action of multidrug efflux pumps with chromosomally encoded antibiotic resistance genes (e.g., mexAB-oprM, mexXY, etc., and the low permeability of the bacterial cellular envelopes.

Also provided is a method for inhibiting aminoarabinose glycosyltransferase (ArnT) of one or more gram negative bacteria comprising contacting the one or more gram negative bacteria with a compound having a structure set forth herein, or a pharmaceutically acceptable salt or stereoisomer of any thereof or a physiological functional derivative of any thereof, in an amount effective to inhibit ArnT of one or more gram negative bacteria.

In an embodiment, "patient" or "subject" refers to mammals and includes human and veterinary subjects. In certain embodiments, the subject is mammalian.

In an embodiment, the compound is administered in a composition comprising a pharmaceutically acceptable carrier.

In certain embodiments, the invention relates to a method of treatment or prophylaxis of a disorder or disease mediated by infection with one or more gram negative bacteria, comprising administering to a patient in need thereof a therapeutically effective amount of the compound of:

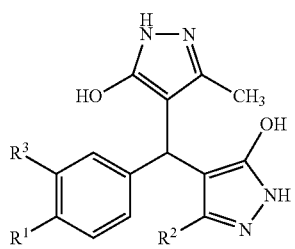

Formula 1

Wherein:

$R^1$ is selected from chloro, fluoro, OH, straight and branched alkyl of 1 to 6 carbon atoms with 1 to 3 carbon atoms preferred and dialkylamino of the formula —$NR^3R^4$ where $R^3$ and $R^4$ are independently selected from hydrogen, straight and branched alkyl of 1 to 6 carbon atoms with 1 to 3 carbon atoms preferred;

$R^2$ is straight and branched alkyl of 1 to 3 carbon atoms;

$R^3$ is H, straight and branched alkyl of 1 to 3 carbon atoms, OH and nitro;

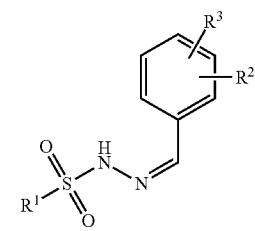

Formula II wherein:

$R^1$ is a moiety selected from the group:

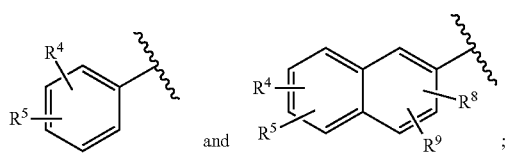

$R^2$, $R^3$, $R^4$, $R^5$, $R^8$ and $R^9$ are independently selected from hydrogen, hydroxyl, amino, fluoro, chloro, straight chain alkyl of 1 to 6 carbon atoms, branched chain alkyl of 3 to 7 carbon atoms, nitro and —$NR^6R^7$ where R and $R^7$ are independently selected from hydrogen, straight and branched alkyl of 1 to 6 carbon atoms with 1 to 3 carbon atoms preferred;

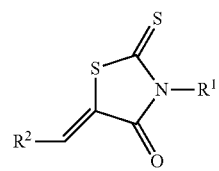

Formula III wherein:

$R^1$ is a moiety —$(CH_2)n$-COOH;

n is 1 to 3;

$R^2$ is selected from moieties of the group

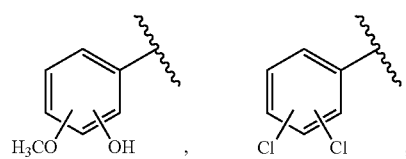

Formula IV

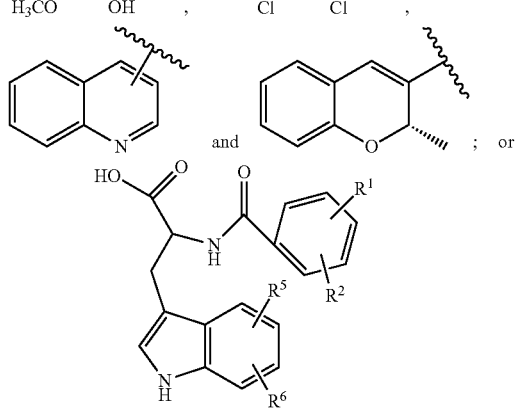

; or wherein:

$R^1$ and $R^2$ and $R^5$ and $R^6$ are independently selected from hydrogen, fluoro, chloro, straight chain alkyl of 1 to 6 carbon atoms, branched chain alkyl of 3 to 7 carbon atoms and —$NR^3R^4$ where $R^3$ and $R^4$ are independently selected from hydrogen, and straight and branched alkyl of 1 to 6 carbon atoms;

or any combination thereof, or a pharmaceutically acceptable salt, solvate, poly-morph, tautomer or prodrug thereof, or the pharmaceutical composition thereof, in combination with at least one additional antibacterial agent.

Also provided is a method for inhibiting ArnT of one or more gram negative bacteria comprising contacting the one or more gram negative bacteria with a compound having any of the structures set forth herein, or a pharmaceutically acceptable salt or stereoisomer of any thereof, or a physiological functional derivative of any thereof, in an amount effective to inhibit ArnT of one or more gram negative bacteria.

Pharmaceutical Compounds

The compounds used in the methods of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

When the structure of the compounds used in this invention includes an asymmetric carbon atom such compound can occur as racemates, racemic mixtures, and isolated single enantiomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "*Enantiomers, Racemates and Resolutions*" by J. Jacques, A. Collet and S. Wilen, Pub. John Wiley & Sons, N Y, 1981. For example, the resolution may be carried out by preparative chromatography on a chiral column.

The subject invention is also intended to include use of all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include carbon-13 and carbon-14.

It will be noted that any notation of a carbon in structures throughout this application, when used without further notation, are intended to represent all isotopes of carbon, such as $^{12}$C, $^{13}$C, or $^{14}$C. Furthermore, any compounds containing $^{13}$C or $^{14}$C may specifically have the structure of any of the compounds disclosed herein.

It will also be noted that any notation of a hydrogen in structures throughout this application, when used without further notation, are intended to represent all isotopes of hydrogen, such as $^1$H, $^2$H, or $^3$H. Furthermore, any compounds containing $^2$H or 3H may specifically have the structure of any of the compounds disclosed herein.

Isotopically-labeled compounds can generally be prepared by conventional techniques known to those skilled in the art or by processes analogous to those described in the Examples disclosed herein using an appropriate isotopically-labeled reagents in place of the non-labeled reagents employed.

The compounds of the instant invention may be in a salt form. As used herein, a "salt" is a salt of the instant compound which has been modified by making acid or base, salts of the compounds. In the case of compounds used for treatment of cancer, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately treating a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

As used herein. "alkyl" includes both branched and straight-chain saturated aliphatic hydrocarbon groups having the specified number of carbon atoms and may be unsubstituted or substituted. The Alkyls are C1-C10 alkyls, or a subset or individual thereof. In a non-limiting example, where the alkyl is C1-C5 as in "C1-C5 alkyl", it is defined to include groups having 1, 2, 3, 4 or 5 carbons in a linear or branched arrangement and specifically includes methyl, ethyl, n-propyl, isopropyl, n-butyl, t-butyl, and pentyl. Alkyl may optionally be substituted with phenyl or substituted phenyl to provide substituted or unsubstituted benzyl.

Heterocyclyl means a saturated or partially unsaturated monocyclic radical containing 3 to 8 ring atoms and preferably 5 to 6 ring atoms selected from carbon or nitrogen but not limited to pyrrolidine.

As used herein the term "aryl" refers to aromatic monocyclic or multicyclic groups containing from 5 to 15 carbon atoms. Aryl groups include, but are not limited to groups such as unsubstituted or substituted phenyl. When referring to said aryl being substituted, said substitution may be at any position on the ring, other than the point of attachment to the other ring system of a compound of the invention. Therefore, any hydrogen atom on the aryl ring may be substituted with a substituent defined by the invention. In embodiments where the aryl is a phenyl ring, said substitution may be at the meta- and/or ortho- and/or para-position relative to the point of attachment. Aryl may optionally be substituted with a heterocyclyl-C(O)— moiety which includes a pyrrolidinyl-C(O)— moiety.

The term "heteroaryl" as used herein, represents a stable monocyclic, bicyclic or polycyclic ring of up to 10 atoms in each ring, wherein at least one ring is aromatic and contains from 1 to 4 heteroatoms or particularly 1 to 2 heteroatoms selected from the group consisting of O, N and S. Bicyclic aromatic heteroaryl groups include phenyl, pyridine, pyrimidine or pyridazine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyriinidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

In the compounds of the present invention, the alkyl, aryl, or heteroaryl groups can be further substituted by replacing one or more hydrogen atoms be alternative non-hydrogen groups. These include, but are not limited to, 1-4 groups selected from alkyl, alkoxy, halo, hydroxy, mercapto, amino, carboxy, cyano and carbamoyl.

The term "substituted" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon (s) or hydrogen (s) atom are replaced by one or more bonds, including double or triple bonds, to a heteroatom. Examples of substituent groups include the functional groups described above, and, in particular, halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups: sulfonyl groups, such as trifluoromethanesulfonyl, methanesulfonyl, and p-toluenesulfonyl; nitro, nitrosyl: mercapto; sulfanyl groups, such as methylsulfanyl, ethylsulfanyl and propylsulfanyl; cyano; heterocyclyl-C(O)-moiety; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity. Moreover, where hydrogens are not shown in the carbon-based structures herein, implicit hydrogens are understood to complete valences as required.

Where a numerical range is provided herein for any parameter, it is understood that all numerical subsets of that numerical range, and all the individual integer values contained therein, are provided as part of the invention. Thus, C1-C10 alkyl includes the subset of alkyls which are 1-3 carbon atoms, the subset of alkyls which are 2-5 carbon atoms etc. as well as an alkyl which has 1 carbon atom, an alkyl which has 3 carbon atoms, an alkyl which has 10 carbon atom, etc.

In an embodiment, the purines discussed herein are one or more of adenosine, inosine, hypoxanthine, or adenine. In an embodiment, "determining" as used herein means experimentally determining.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing any one or combination of the compounds described herein, and pharmaceutically acceptable excipients.

As used herein, the term "optionally" means that the subsequently described event(s) may or may not occur, and includes both event(s), which occur, and events that do not occur.

As used herein, the term "substituted with one or more groups" refers to substitution with the named substituent or substituents, multiple degrees of substitution, up to replacing all hydrogen atoms with the same or different substituents, being allowed unless the number of substituents is explicitly stated. Where the number of substituents is not explicitly stated, one or more is intended.

As used herein, "a compound of the invention" includes any of the compounds described herein or a salt, solvate or physiologically functional derivative thereof.

As used herein, the term "solvate" refers to a complex of variable stoichiometry formed by a solute (or and for any of the compounds described herein, a salt thereof) and a solvent. Such solvents for the purpose of the invention may not interfere with the biological activity of the solute. Examples of suitable solvents include, but are not limited to, water, acetone, methanol, ethanol and acetic acid. Preferably the solvent used is a pharmaceutically acceptable solvent. Examples of suitable pharmaceutically acceptable solvents include water, ethanol and acetic acid. Most preferably the solvent is water.

As used herein, the term "physiologically functional derivative" refers to a compound (e.g. a drug precursor) that is transformed in vivo to yield any of the compounds described herein, or a pharmaceutically acceptable salt, hydrate or solvate of the compound. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

All combinations of the various elements described herein are within the scope of the invention unless otherwise indicated herein or otherwise clearly contradicted by context. Whilst the embodiments for each variable have generally been listed above separately for each variable, this invention also includes those compounds in which several or each embodiment is selected from each of the embodiments listed above. Therefore, this invention is intended to include all combinations of embodiments for each variable.

The compounds described herein including salts, solvates and physiologically functional derivatives thereof are believed to be inhibitors of aminoarabinase glycosyltransferase (ArnT), and thus be potentially useful in the prevention or treatment of diseases, disorders and conditions associated with infections with resistant gram negative organisms, including multidrug resistant organisms (MDR). In certain instances, any one or combination of the presently described compounds could be used prophylactically to prevent a drug resistant condition.

Any one or combination of two or more of the compounds described herein, or its pharmaceutically acceptable salts and pharmaceutical compositions can be used to treat or prevent a variety of conditions or diseases mediated by infection with one or more multidrug resistant gram negative organisms. Similarly, one or more additional agent such as an antibacterial agent (i.e. Polymyxin antibiotic) may be added in combination with the any one or combination of two or more of the compounds described herein or its pharmaceutically acceptable salts and pharmaceutical compositions can be used to treat or prevent a variety of conditions or diseases mediated by infection with one or more multidrug resistant gram negative organisms.

The invention thus provides any one or combination of two or more of the compounds described herein and salts, solvates and physiologically functional derivatives thereof for use in therapy, and particularly in the treatment of diseases and conditions mediated by exposure or infection with one or more resistant gram negative organisms, including multidrug resistant organisms.

In a further embodiment, the present invention provides a method of treatment of a patient suffering from a disorder mediated by infection with one or more drug resistant gram negative organisms, which comprises administering to said patient an effective amount of any one or combination of two or more of the compounds described herein or a pharmaceutically acceptable salt, solvate, or a physiologically functional derivative thereof.

In a further embodiment, the present invention provides for the use of any one or combination of two or more of the compounds described herein, or a pharmaceutically acceptable salt or solvate thereof, or a physiologically functional derivative thereof, in the preparation of a medicament for the treatment of a disorder mediated by infection with one or more drug resistant gram negative organisms, including multidrug resistant organisms.

While it is possible that, for use in therapy, any of the compounds described herein, as well as salts, solvates and physiological functional derivatives thereof, may be administered as the raw chemical, it is possible to present the active ingredient as a pharmaceutical composition. Accordingly, the invention further provides a pharmaceutical composition, which comprises a any of the compounds described herein and salts, solvates and physiological functional derivatives thereof, and one or more pharmaceutically acceptable carriers, diluents, or excipients. Any of the compounds described herein and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing any one or combination of two or more of the compounds described herein, or salts, solvates and physiological functional derivatives thereof, with one or more pharmaceutically acceptable carriers, diluents or excipients.

Pharmaceutical compositions of the present invention may be presented in unit dose forms containing a predetermined amount of active ingredient per unit dose. Such a unit may contain, for example, 5 µg to 1 g, preferably 1 mg to 700 mg, more preferably 5 mg to 100 mg of any of the compounds described herein, depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), inhaled, nasal, ocular, or parenteral (including intravenous and intramuscular) route. Such compositions may be prepared by any method known in the art of pharmacy, for example by bringing into association the active ingredient with the carrier(s) or excipient(s).

In a further embodiment, the present invention provides a pharmaceutical composition adapted for administration by the oral route, the treatment of diseases and conditions related to infection with one or more multidrug resistant gram negative organisms.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

It should be understood that in addition to the ingredients particularly mentioned above, the compositions may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of any of the compounds described herein for the treatment of diseases or conditions associated with one or more multi-drug resistant gram negative organisms, will generally be in the range of 5 µg to 10 mg/kg body weight of recipient (mammal) per day and more usually in the range of 5 µg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound, per se.

Compounds of the present invention, and their salts and solvates, and physiologically functional derivatives thereof, may be employed alone or more typically in combination with other therapeutic agents for the treatment of diseases and conditions related to infection with one or more multi-drug resistant gram negative organisms. Combination therapies according to the present invention thus comprise the administration of at least one compound, or a pharmaceutically acceptable salt or solvate thereof, or a physiologically functional derivative thereof, and the use of at least one other pharmaceutically active agent. The compound(s) and the other pharmaceutically active agent(s) may be administered together or separately and, when administered separately this may occur simultaneously or sequentially in any order.

The amounts of the compound(s) and the other pharmaceutically active agent(s) and the relative timings of administration will be selected in order to achieve the desired combined therapeutic effect.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

The compounds of this invention may be made by a variety of methods, including standard chemistry. The compounds utilized herein were purchased from a number of different sources listed in Table 1. Any previously defined variable will continue to have the previously defined meaning unless otherwise indicated.

Compounds of the present invention may be prepared by methods known in the art of organic synthesis. It is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of the present invention. Those skilled in the art will recognize if a stereocenter exists in compounds of the present invention. Accordingly, the present invention includes all possible stereoisomers and includes not only mixtures of stereoisomers (such as racemic compounds) but the individual stereoisomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel. S. H. Wilen, and L. N. Mander (Wiley-Interscience, 1994).

TABLE 1

Sources of ArnT Inhibitor/Antagonist Compounds

| Compound identifier | Commercial Source |
| --- | --- |
| 20 | ChemBridge Corp. |
| 14 | ChemBridge Corp. |
| 15 | ChemBridge Corp. |
| 19 | Vitas-M Laboratory, Ltd |
| U2 | Vitas-M Laboratory, Ltd |
| 36 | Vitas-M Laboratory, Ltd |
| 37 | Vitas-M Laboratory, Ltd |
| U5 | Vitas-M Laboratory, Ltd |
| U6 | Vitas-M Laboratory, Ltd |
| 3 | ChemBridge Corp. |
| 6 | NCI (Obtained from the Drug synthesis and Chemistry Branch, Developmental Therapeutics Program, Division of Cancer Treatment and Diagnosis, National Cancer Institute) |
| U4 | Vitas-M Laboratory, Ltd |
| U7 | Vitas-M Laboratory, Ltd |
| 2 | ChemBridge Corp. |
| 9 | Vitas-M Laboratory, Ltd |

Molecular Biology

Standard methods in molecular biology are described Sambrook. Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning*, $3^{rd}$ ed., Cold Spring Harbor Laboratory Press, Cold Spring Harbor, N.Y.; Wu (1993) *Recombinant DNA*. Vol. 217. Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York: Ausubel, et al. (2001) *Current Protocols in Molecular Biology*, Vol. 3, John Wiley and Sons. Inc., NY, NY, pp. 16.0.5-16.22.17: Sigma-Aldrich, Co. (2001) *Products for Life Science Research*, St. Louis, Mo.; pp. 45-89: Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York: Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

"Treating" or "treatment" of a state, disorder or condition includes:

(1) preventing or delaying the appearance of clinical symptoms of the state, disorder, or condition developing in a person who may be afflicted with or predisposed to the state, disorder or condition but does not yet experience or display clinical symptoms of the state, disorder or condition; or (2) inhibiting the state, disorder or condition, i.e., arresting, reducing or delaying the development of the disease or a relapse thereof (in case of maintenance treatment) or at least one clinical symptom, sign, or test, thereof; or (3) relieving the disease, i.e., causing regression of the state, disorder or condition or at least one of its clinical or sub-clinical symptoms or signs.

The benefit to a subject to be treated is either statistically significant or at least perceptible to the patient or to the physician.

"Patient" or "subject" refers to mammals and includes human and veterinary subjects. Certain veterinary subjects may include avian species.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

As used herein, the phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopeias for use in animals, and more particularly in humans.

This invention will be better understood from the Experimental Details, which follow. However, one skilled in the art will readily appreciate that the specific methods and results discussed are merely illustrative of the invention as described more fully in the claims that follow thereafter.

Kits

The present invention also provides kits comprising the components of the invention in kit form. A kit of the present invention includes one or more components including, but not limited to, ArnT inhibitor compounds, as discussed herein, in association with one or more additional components including, but not limited to a pharmaceutically acceptable carrier and/or one or more antibacterial agent or compounds, as discussed herein. The ArnT inhibitor compounds, composition and/or the therapeutic agent can be formulated as a pure composition or in combination with a pharmaceutically acceptable carrier, in a pharmaceutical composition.

In one embodiment, a kit includes ArnT inhibitor compounds/composition of the invention or a pharmaceutical composition thereof in one container (e.g., in a sterile glass, tube, or plastic vial) and a pharmaceutical composition thereof and/or one or more antibacterial agent or compounds in another container (e.g., in a sterile glass or plastic vial).

In another embodiment of the invention, the kit comprises one or any combination of ArnT inhibitor compounds, along with a pharmaceutically acceptable carrier, optionally in combination with one or more therapeutic agent components, such as one or more antibacterial agents or compounds, formulated together, optionally, in a pharmaceutical composition, in a single, common container.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

Examples

In gram negative bacteria, as typified by Escherichia coli and Salmonella typhimurium, the most effective modification for reduction of negative membrane charge is the attachment of the cationic sugar 4-amino-4-deoxy-L-arabinose (L-Ara4N) to lipid A phosphate groups at the 1 and 4' positions (7). L-Ara4N is provided by an undecaprenyl phosphate (UndP) carrier molecule. The reaction is catalyzed on the periplasmic side of the inner membrane by ArnT (also known as PmrK), an integral membrane lipid-to-lipid glycosyltransferase, and the last enzyme to act in the aminoarabinose biosynthetic pathway common to Gram-negative bacteria (4, 7, 8) (FIGS. 1A-B). Critically, in E. coli, the lipid A 1-phosphate group is also modified by EptA (PmrC), which adds phosphoethanolamine (pEtN) to this site, competing with ArnT enzymes for 1-phosphate specificity (9, 10).

In order to gain insight into the structure and mechanistic basis of ArnT function, we screened twelve prokaryotic putative ArnTs from species selected to cover a wide area of genomic space for expression and stability in detergents to find a suitable candidate for crystallization (11). ArnT from Cupriavidus metallidurans CH34 (ArnTCm), with overall percentage pairwise sequence identity to ArnT's from E. coli (ArnTEc) and S. typhimurium (ArnTSt) of ~25%, emerged as the most promising based on expression levels and behavior in size exclusion chromatography in detergent. Indeed, this protein crystallized in lipidic cubic phase (LCP) (12), and these crystals were suitable for structure determination.

We therefore sought to characterize the catalytic activity of ArnTCm to demonstrate its function as an ArnT enzyme capable of transferring L-Ara4N to lipid A. Thin layer chromatography of $^{32}$P-labeled lipid A isolated from E. coli showed that heterologous expression of ArnTCm in an E. coli strain lacking endogenous arnT and eptA (ΔarnTΔeptA) resulted in lipid A modification by L-Ara4N. The identity of the transferred sugar was confirmed using negative ion MALDI-TOF mass spectrometry. Indeed, expression of ArnTCm in ΔarnTΔeptA yielded two major peaks, the first at 1928.0 corresponding to L-Ara4N-modified lipid A and the second at 1797.0 corresponding to unmodified, bisphosphorylated hexa-acylated lipid A (FIG. 2A).

Functional Characterization of ArnT$_{Cm}$.

Next, we tested the ability of ArnTCm to confer resistance to polymyxin. Surprisingly, unlike ArnTSt, ArnTCm expressed in E. coli failed to rescue resistance to polymyxin in ΔarnT (13, 14) (FIG. 2B), and in ΔarnTΔeptA (FIG. 2C), despite its ability to transfer L-Ara4N to lipid A. However, while it is known that ArnTSt adds L-Ara4N to both the 1 and 4' phosphates of lipid A (7), ArnTCm appears only to yield a single lipid A species modified at the 1-phosphate position (FIG. 2D).

Figure 2A:
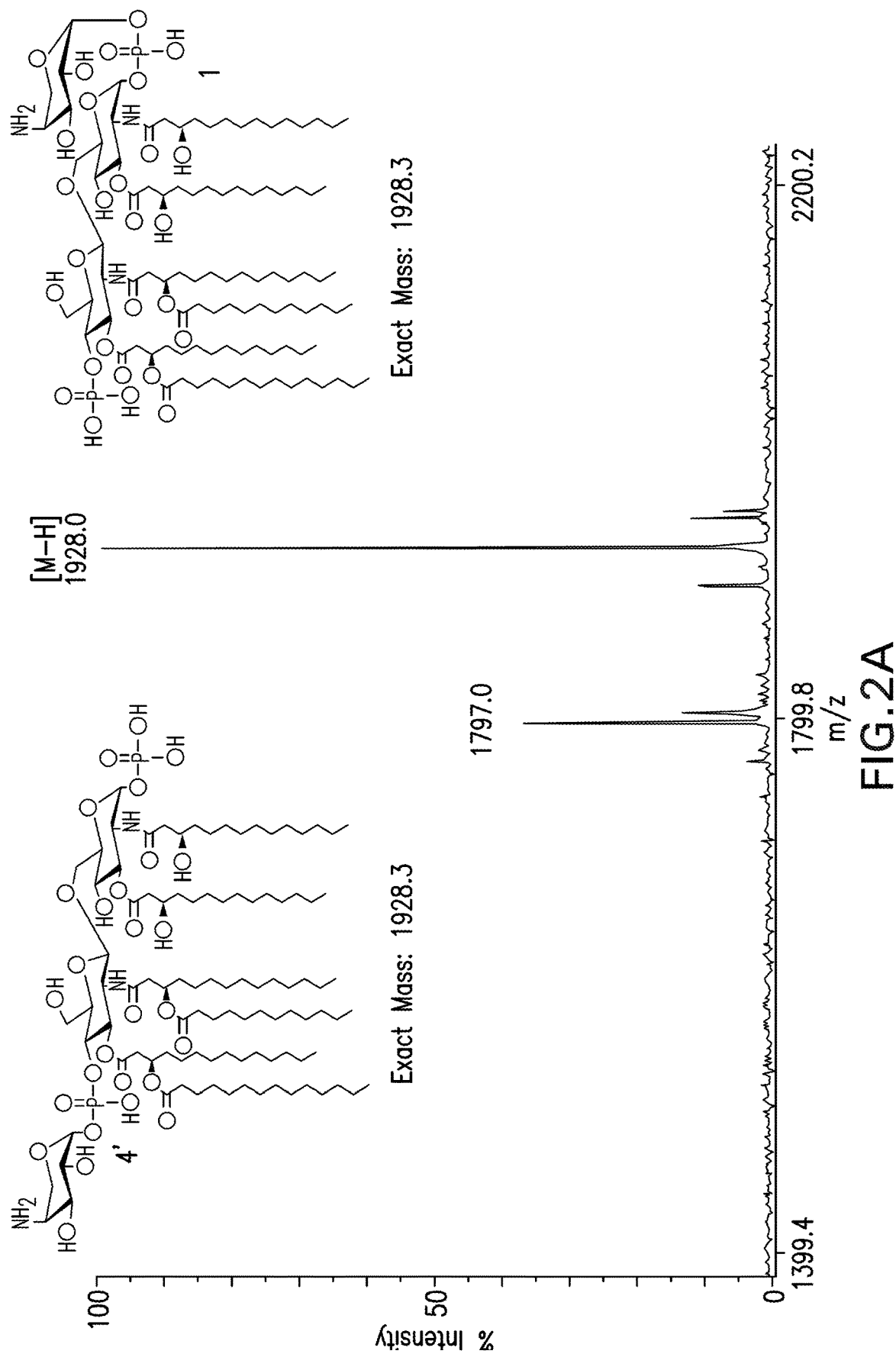
FIGS. 2A-D are graphs and blots showing functional characterization of ArnTCm

Specifically, FIG. 2A shows negative ion MALDI-TOF spectrometry of lipid A purified from E. coli WD101 ΔarnTΔeptA strain expressing ArnT$_{Cm}$. The major peak at 1928.0 corresponds to lipid A modified with L-Ara4N added at either the 4' (shown on the left) or 1 (shown on the right) acceptor position. The secondary peak at 1797.0 corresponds to bisphosphorylated hexa-acylated lipid A.

Figures 2B, 2C:
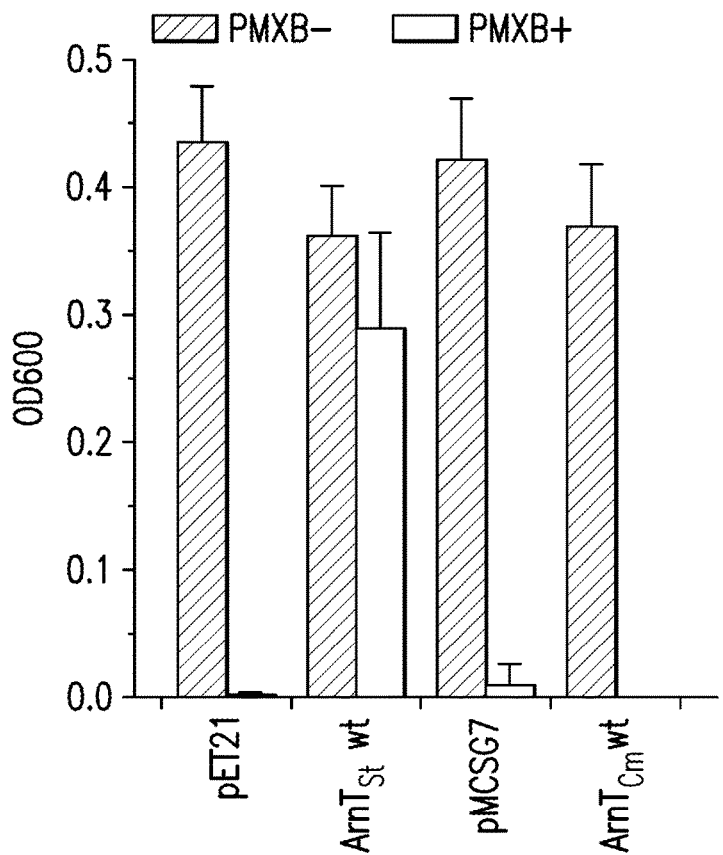
Figure 2D:
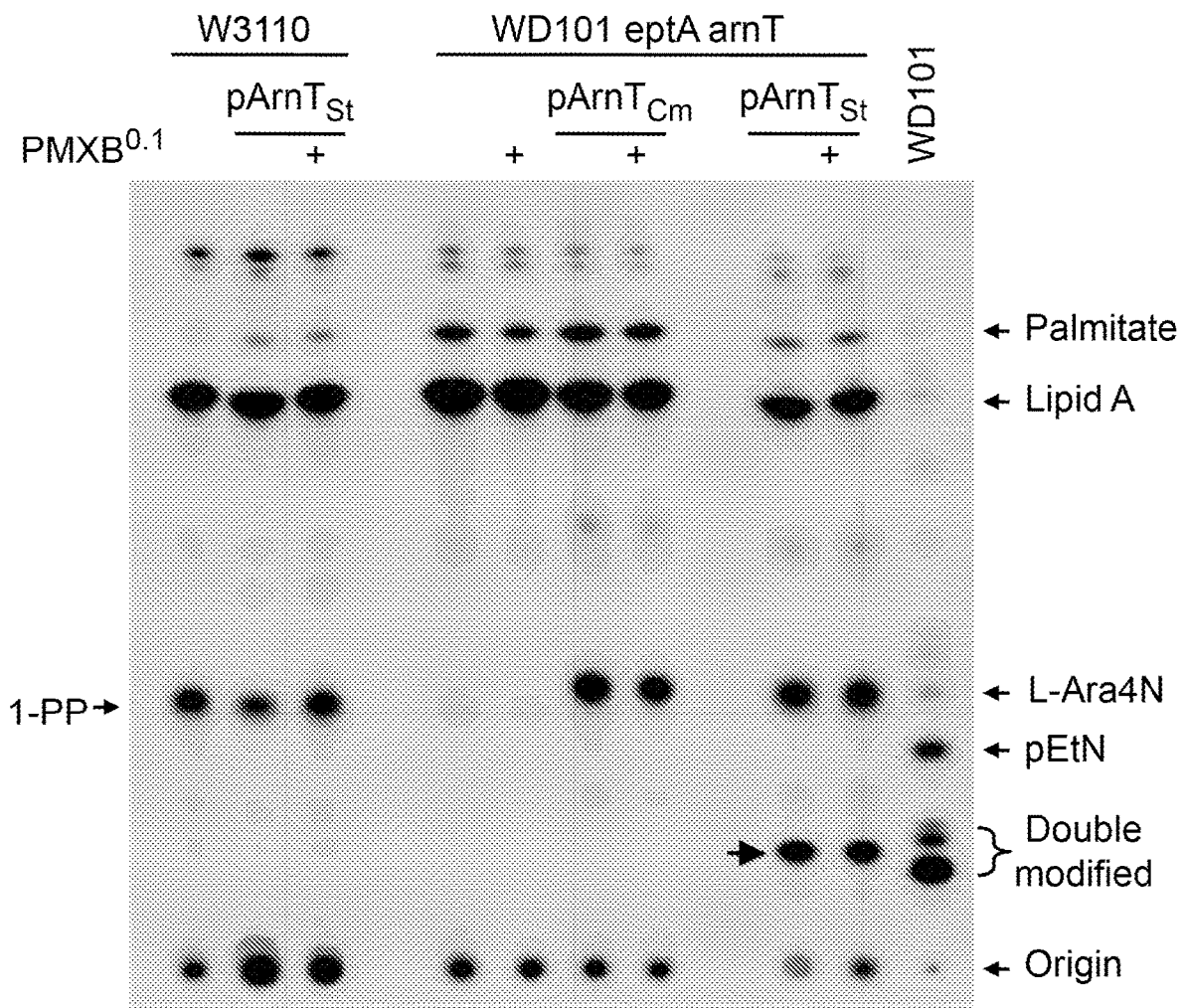

FIG. 2B is a bar graph showing the effect of introduction of ArnT$_{St}$ and ArnT$_{Cm}$ into the BL21(DE3)ΔarnT knockout E. coli strain. Only ArnT$_{St}$ is able to rescue polymyxin resistance. ArnT$_{Cm}$ was expressed here using the pMCSG7 vector, and not pNYCOMPS-Nterm used for crystallography-related protein production, because of matching antibiotic resistance of the former vector with pET21 used for ArnT$_{St}$ expression.

FIG. 2C illustrates the determination of minimal inhibitory concentration of polymyxin B (PMXB) in WD101 strain (PMXB-resistant) and ΔarnTΔeptA double-mutant (PMXBsensitive). Expression of ArnT$_{Cm}$ in ΔarnTΔeptA does not rescue resistance to PMXB.

FIG. 2D shows an expanded analysis of $^{32}$P-labeled lipid A by thin-layer chromatography (TLC). Lipid A in W3110 strain carries only a pyrophosphate modification (1-PP) and is sensitive to polymyxin B (PMXB). WD101 produces double modified lipid A with Ara4N and phosphoethanolamine (pEtN). In the absence of both arnT and eptA (a gene required for the addition of phosphoethanolamine to the 1 phosphate group of lipid A), ArnT$_{St}$ adds L-Ara4N to both the 1 and 4' phosphates, leading to both single- and double-modified lipid A spots (double-modified L-Ara4N lipid A indicated by red arrow). In contrast, ArnT$_{Cm}$ only yields a single modified lipid A species. Moreover, in a ΔarnT single knockout strain, ArnT$_{Cm}$ is unable to modify lipid A. The conclusion is that ArnT$_{Cm}$, is stereospecific for the 1 phosphate group of lipid A. Pre-induction with PMXB (0.1 µg/mL) did not significantly change the amount and/or character of lipid A modification.

These data suggest that modification at the 1-position does not confer protection to this antibiotic in E. coli, in agreement with the primacy of removal or modification of the 4'-phosphate in conferring polymyxin resistance shown in other species (15, 16). Therefore, we utilized a polymyxin growth assay previously established in E. coli for ArnTSt (13, 14), and structural hypotheses derived from the structure of C. metallidurans ArnT, as described below, to test the S. typhimurium enzyme. The overall pairwise sequence identity between ArnTSt and ArnTCm is 25%, but the degree of conservation in and around the key regions for activity is substantially higher, suggesting that their structure and function are likely conserved.

The structure of wild-type ArnTCm was determined to 2.8 Å resolution by the single-wavelength anomalous diffraction method using SeMet-substituted protein (Table 2). ArnTCm crystallized as a monomer, consisting of a transmembrane (TM) domain and a soluble periplasmic domain (PD) positioned above it (FIG. 3A-B). The TM domain, surrounded by a clearly distinguishable hydrophobic belt, shows 13 TM helices, similar to those recently predicted for ArnT from *Burkholderia cenocepacia* (17), in an intricate arrangement. The structure has three juxtamembrane (JM) helices (JM1-3). JM1 and JM2 are both part of the first periplasmic loop and are perpendicular to each other, creating a distinctive cross-shaped structure (FIG. 3A-B). JM3 leads into a flexible periplasmic loop between TM7 and TM8, previously shown to be functionally important (13). TM13 leads into the PD, which has an α/β/α arrangement consisting of 7 helices (α1-7) with 4 parallel beta strands (β1-4) and an antiparallel β5 one in a 21354 order.

ArnT can be classified as a representative of the GT-C fold of glycosyltransferases (18). The protein is similar in fold to a bacterial oligosaccharyltransferase (OST) from *Campylobacter lari* (PglB) and to an archaeal OST from *Archaeoglobus fulgidus* (AglB) (19, 20). The topology of the TM region differs amongst the three proteins, but an inner core of AglB's TM domain aligns well with that of ArnTCm. Moreover, one part of the periplasmic domains of ArnTCm and PglB is similar in structure. These similarities in fold may underscore an evolutionary relationship between the three proteins, but their functions are markedly different. Unique to ArnT, the glycosyl acceptor is a lipid (lipid A). Since both substrates have a lipidic component, ArnT is expected to be capable of bringing both from within the membrane to the active site for catalysis.

Three Major Cavities of ArnT and Metal Binding Regions

The structure of ArnT shows three major cavities (FIG. 3A), which differ in their electrostatic nature. By far the largest (over 3,000 Å3 within the membrane), cavity 1 is amphipathic with a lower, primarily hydrophobic portion located below the level of the membrane and an upper hydrophilic portion. We hypothesize that cavity 1 is where lipid A binds to the enzyme. Interestingly, the hydrophobic portion of cavity 1 is directly accessible from the outer leaflet of the inner membrane and it has a volume compatible with the acyl chains and the glucosamine sugar backbone of lipid A. This suggests a mechanism for lipophilic substrate recruitment from the membrane, although entrance to cavity 1 seems to be occluded by the periplasmic loop connecting TM7 and TM8 (FIG. 3A). The Kdo sugars of lipid A could bind to the hydrophilic upper portion of the cavity, possibly interacting with the PD. The smaller cavity 2 is primarily hydrophilic, despite being at least in part below the boundary of the membrane (FIG. 3A). Cavities 1 and 2 are connected through a narrow passage, making cavity 2 an attractive candidate for binding of the L-Ara4N moiety. Finally, cavity 3, located close to the cytoplasmic side of the molecule is entirely hydrophobic (FIG. 3A).

The present data also shows that ArnT binds a metal. Anomalous density likely corresponding to zinc is observed between JM1 and the periplasmic loop connecting helices 7 and 8. The $Zn^{+2}$ ion is bound with a five-point trigonal bipyramidal coordination by E84 (bidentate), H265 and H267, and likely by a water molecule (FIG. 3A-B), which is replaced in our crystals by the carboxy terminus from a symmetry-related molecule. All three metal-coordinating residues appear to be important for function, as shown by the lack of polymyxin resistance in ArnTSt when mutated. However, H265 is a valine (V241) in ArnTSt, and therefore its metal coordination must differ, although, perhaps indicatively, the mutation of V241 to histidine, as found in ArnTCm, is functional in the growth assay, whilst its mutation to cysteine is not (13).

Co-Crystallization of ArnTCm with UndP

Figure 6A:
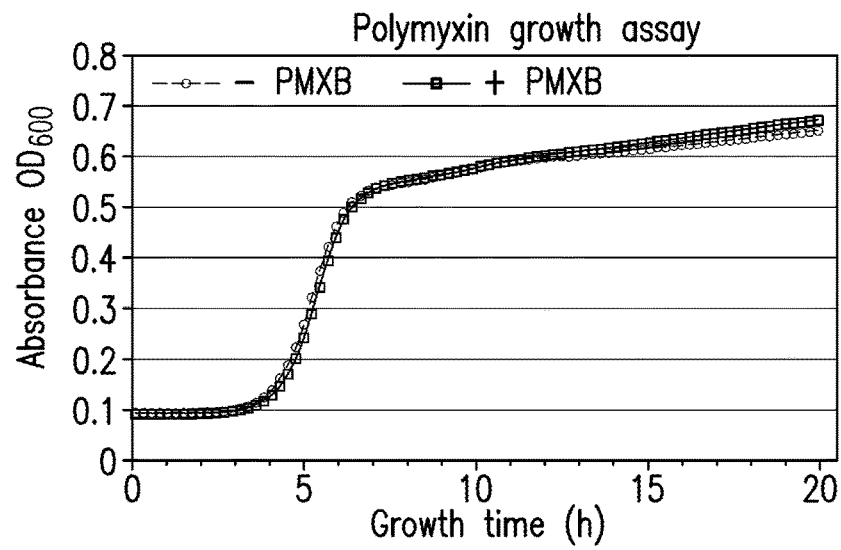
FIGS. 6A-C show graphic results of control polymyxin growth assays demonstrating the behavior of strains used for screening of compounds.
Figure 6B:
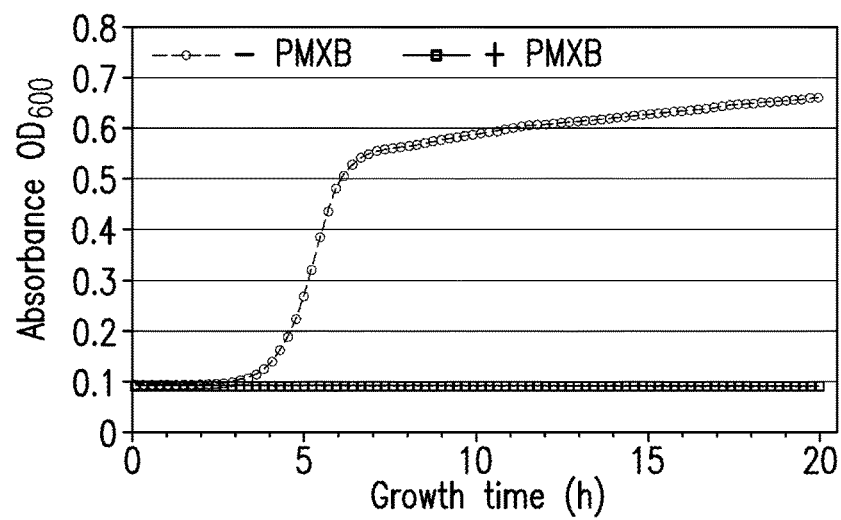
Figure 6C:
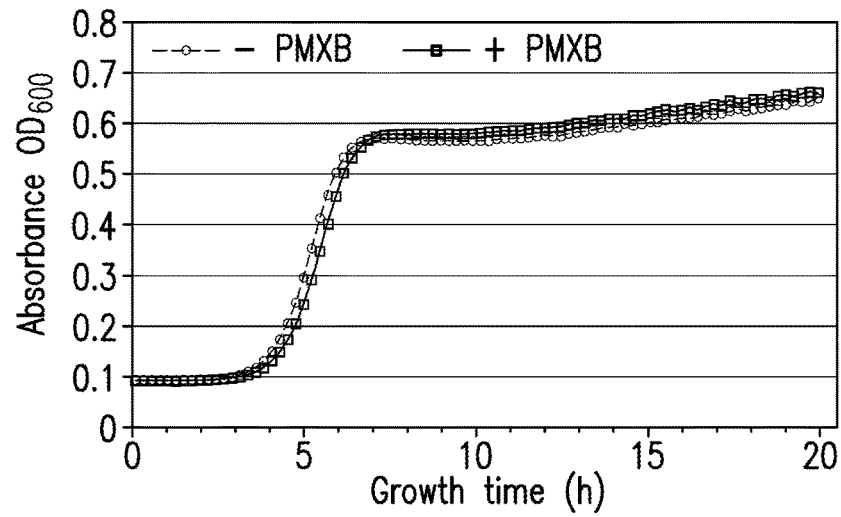

To investigate how ArnT interacts with its lipid substrates, we co-crystallized ArnTCm with UndP, by incorporating this hydrophobic compound into the LCP mixture. The structure of ArnTCm from a crystal grown with a monoolein/UndP mixture was solved at 3.2 Å (Table 2) and featured two discontinuous densities compatible with a poly-prenyl ligand, allowing us to locate the carrier lipid in the ArnTCm structure (FIG. 3A). The first density (FIG. 6A), stemming from inside cavity 2 corresponds to the phosphate headgroup and five prenyl groups (FIG. 4A). These data allow us to define the approximate location within cavity 2 of the L-Ara4N group, which is attached to the phosphate of the polyprenyl carrier for catalysis, and to explain the hydrophilic lining observed within this cavity. The second region of density, corresponding to four prenyl groups of UndP, extends from cavity 3, which is lined with hydrophobic residues providing an ideal environment for accommodating the lipid tail. Mutations within this region to alanine or threonine, or attempts to block the access to cavity 3 by introducing tryptophan mutations, had only a marginal effect on ArnTSt function. These results may indicate flexibility of the UndP binding mode away from the active site.

Strikingly, in the UndP-bound structure a structural rearrangement of the periplasmic loop between TMs 7 and 8 is observed, located proximal to the active site, and previously shown to have functional relevance (13). A coil to helix transition results in an extension of JM3 by two full turns, leading to a repositioning of several residues around UndP, and the loss of metal coordination. The nature of $Zn^{+2}$ coordination is consistent with a role in fixing the loop in a conformation that allows the UndP substrate to bind. The conformation observed in the UndP-bound structure substantially reduces the volume of cavity 2, as the extension of JM3 envelopes the head of the substrate. Furthermore, although the volume of cavity 1 is only marginally changed, the UndP-mediated structural rearrangement enables unbinding of the TM7-TM8 loop from the cavity 1 surface, potentially to enable access to lipid A.

The phosphate of UndP is coordinated by K85 and R270, whilst the oxygen of the phosphodiester bond participates in hydrogen bonding with Y345 (FIG. 4A). These three residues are absolutely conserved, and their mutation in ArnTSt leads to complete loss of function (FIG. 4B and (13)). Interestingly, a sulfate ion present in AglB, thought to occupy the position of the UndP phosphate (20), is superimposable with the phosphate of UndP in our structure, suggesting a common modality for donor substrate orientation.

Figure 4C:
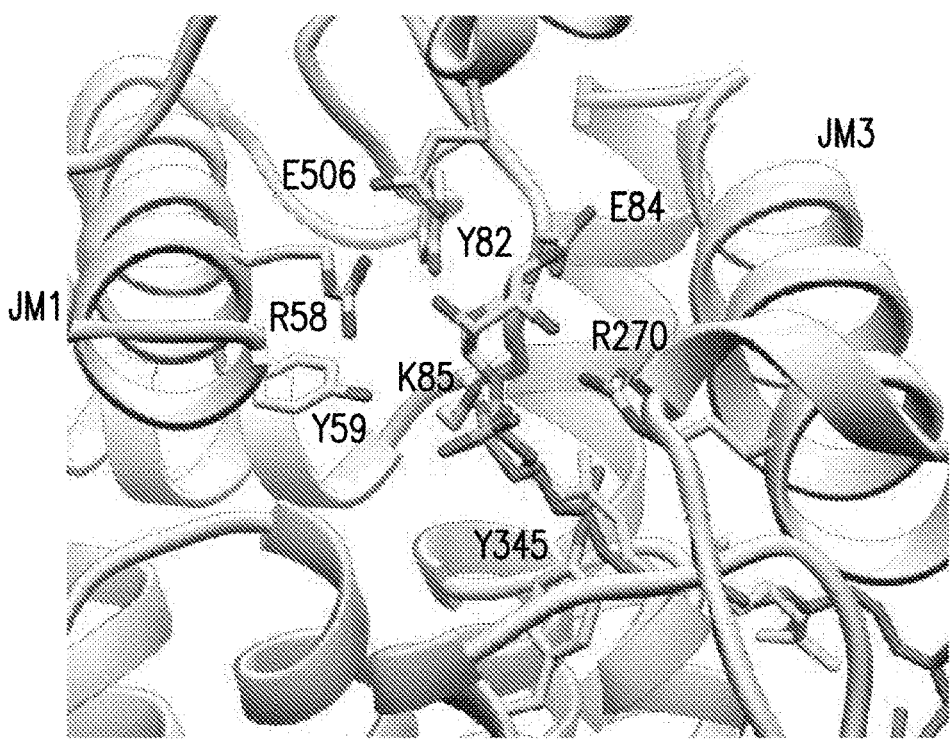
Figure 4B:
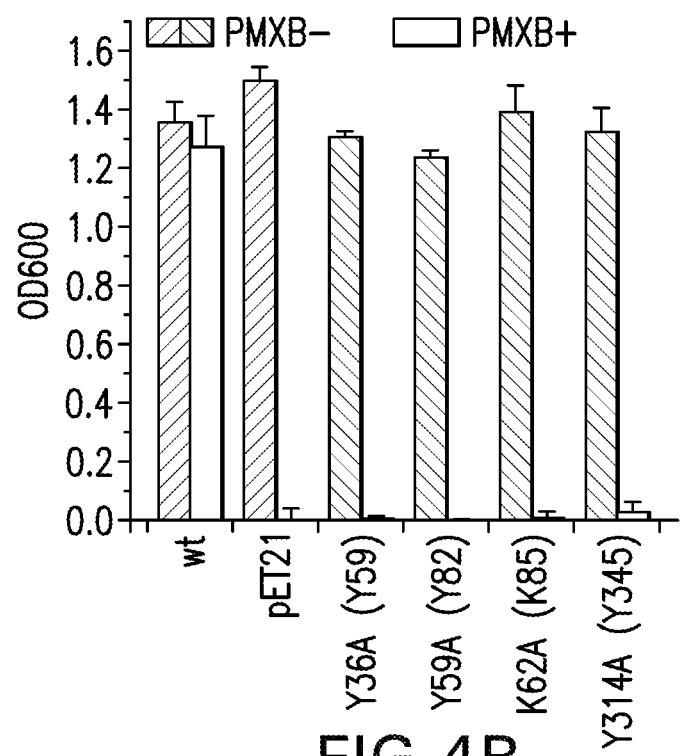

Naïve docking to position L-Ara4N-tri-prenyl phosphate on the ArnTCm structure yielded several families of consistent poses. We selected one highly populated pose, based on lowest energy and the positions of the phosphate and three included prenyl groups compared to the experimentally observed UndP. This pose revealed three additional conserved residues (Y59, Y82 and E506) that are likely to interact with the substrate. We confirmed the importance of Y59 and Y82 in ArnTSt function (FIG. 4B). In addition, the residues corresponding to Y59, K85, R270 and E506, have been shown to be functionally relevant in ArnT from *Burkholderia cenocepacia* (17). Intriguingly, E84, which participates in metal coordination in the apo conformation, appears here to bind to the amino group of L-Ara4N, suggesting a possible role for this residue in transitioning to the substrate-bound form (FIG. 4C).

These crystal structures of ArnT from *Cupriavidus metallidurans* (Cme) alone and the other bound to UndP at 2.8 and 3.2 Å resolution respectively, have provided the first molecular insights into the transmembrane architecture and the catalytic machinery of ArnTs (FIG. 3A-B). The structures revealed the respective binding cavities for both substrate, lipid A and the UndP carrier, as well as atomic-level details of the active site where LAra4N is actually transferred and where the two cavities converge (FIG. 3A-B). These structures provided the basis for identifying and mapping key functional residues inside the UndP cavity and within the active site, and to propose a catalytic mechanism in which two highly conserved Asp residues "activate" the Lipid A phosphate group for a nucleophilic attack. Importantly, while the overall pairwise sequence identity between ArnT from Cme and ArnT from *E. coli* or *S. typhimurium* is ~25%, conservation is substantially higher for the residues lining the cavities or the active site, and the key residues identified are conserved across the three species (FIGS. 3A-B). These data further provide the basis for designing inhibitors of ArnT and for developing compounds and treatments for MDR gram negative infections.

Reaction Mechanism for ArnT's

Figure 5A:
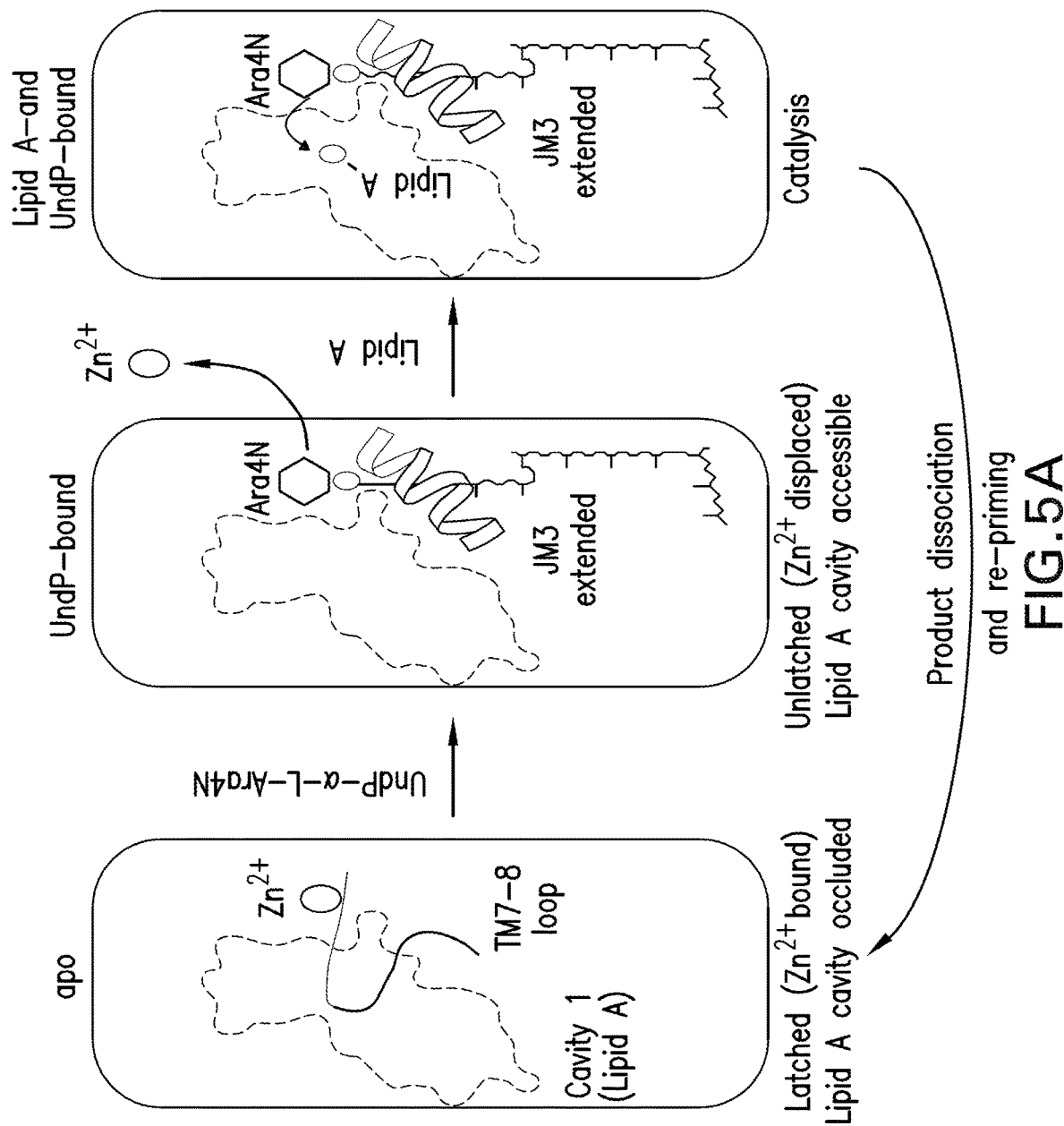
FIGS. 5A-D show catalytic mechanisms of ArnT.
Figure 5B:
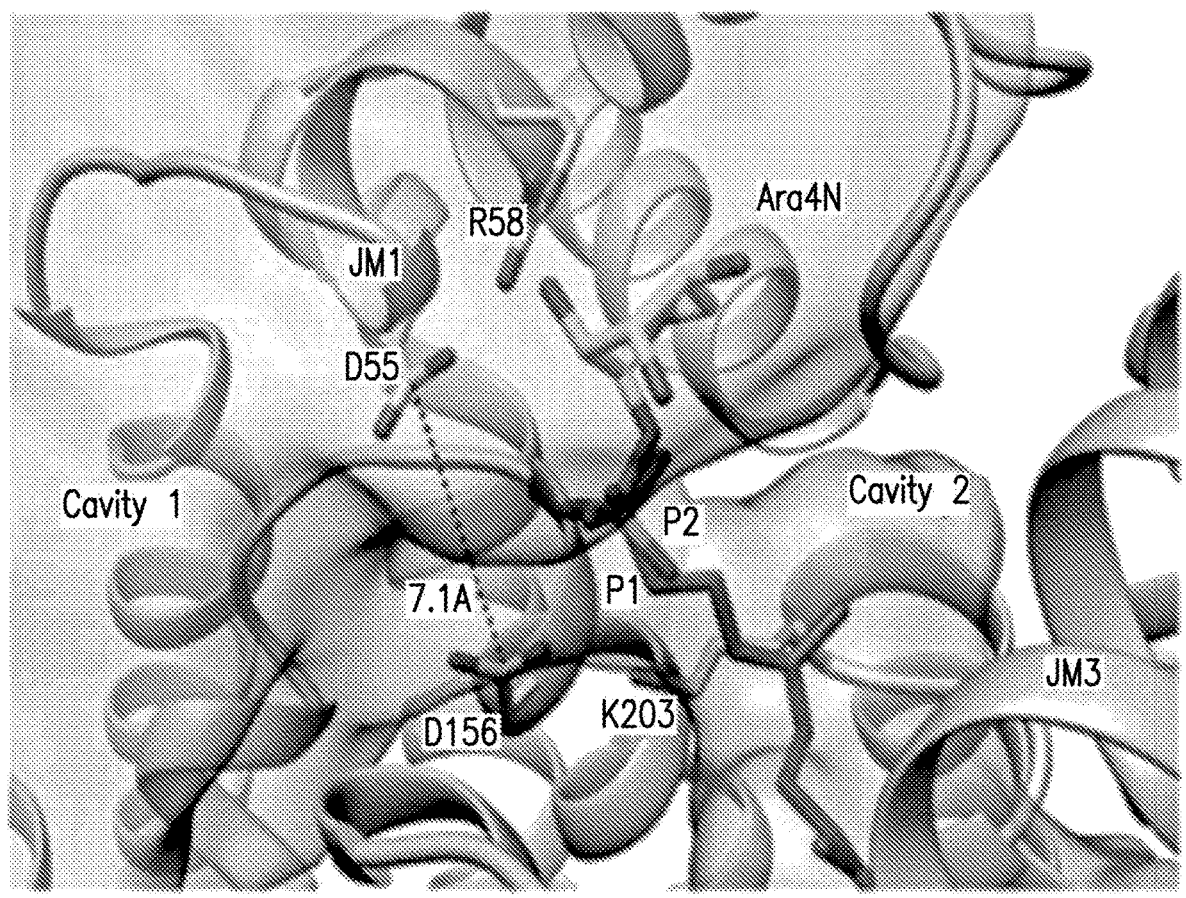
Figure 5C:
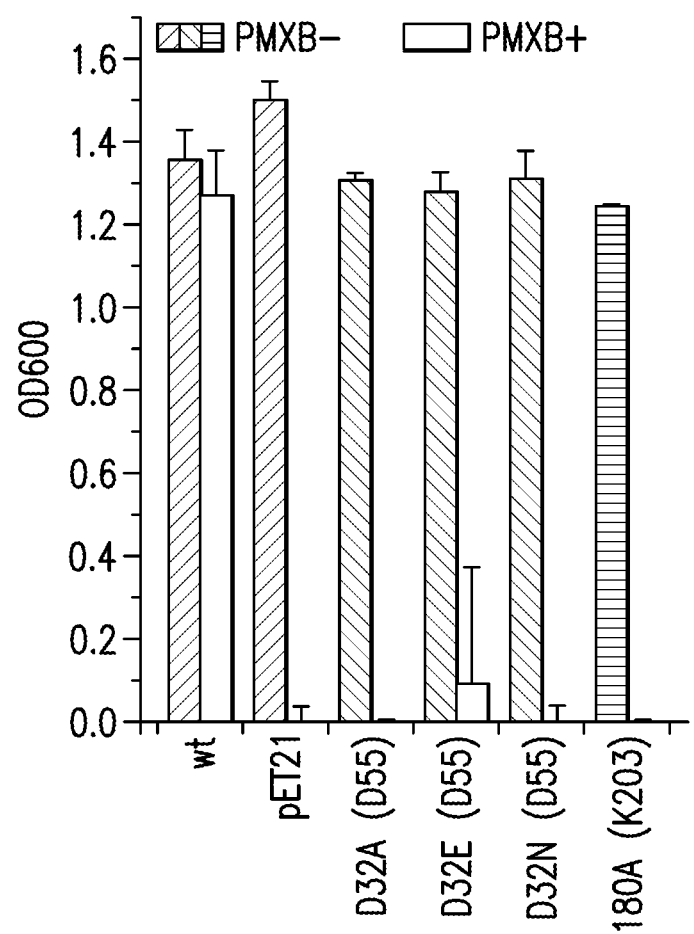
Figure 5D:
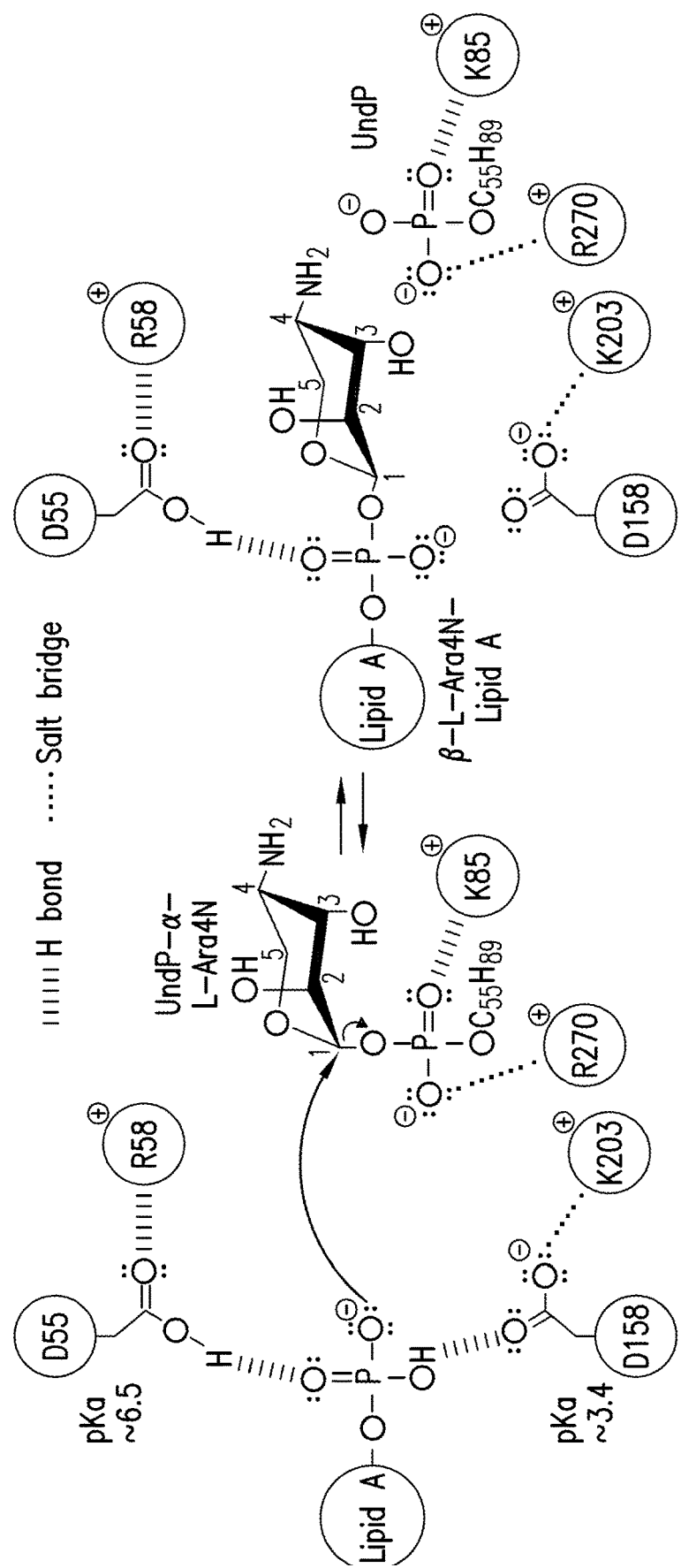

Based on these data, we propose a possible reaction mechanism for ArnT's. Overall, the structures of apo and UndP-bound ArnTCm suggest that the binding of substrates may be sequential, with UndP-α-L-Ara4N preceding lipid A, which may access the now-exposed cavity 1 from the membrane (FIG. 5A). The active site, at the interface between the two substrate cavities, is completed by elements of the extended JM3 helix only upon UndP binding (FIGS. 3A-B and FIG. 5A). The structure of the active site with bound UndP and modeled L-Ara4N also suggests a possible catalytic mechanism. Two conserved aspartic acid residues D55 and D158, located at the interface between cavities 1 and 2 and spatially adjacent with Cγ-Cγ distance of 7.1 Å, are each involved in salt bridges with conserved positively charged residues (R58 and K203, respectively) (FIG. 5B). Mutations of D55 or K203 lead to loss of activity (FIG. 5C). We propose that the two aspartates, with charges localized due to their ligation by positive side chains, may coordinate two of the oxygen atoms of the acceptor lipid A phosphate, leaving the third oxygen atom with a net negative charge. We propose that this charged oxygen atom performs the nucleophilic attack on the C carbon of the UndP-α-L-Ara4N donor sugar ring (FIG. 5D). This mechanism is consistent with inversion of the glycosidic bond, as reported for L-Ara4N attachment to lipid A (21). Examples of phosphate acting as a nucleophile have been described previously, for example in glucose-1-phosphate uridylyltransferase, which catalyzes the production of UDP-glucose from glucose-1-phosphate and UTP (22). For PglB, it has been suggested that catalysis relies on a nucleophilic attack by the acceptor amide (19, 23). An active site Mg2+ appears to localize the charge of an aspartate and a glutamate that coordinate the acceptor amide. In ArnT, we propose that this function is accomplished on D55 and D158 by R58 and K203, and that these two aspartates then coordinate the acceptor phosphate.

Designing *S. typhimurium* and *E. coli* ArnT Inhibitors Derived from L-Ara4N.

To date, the only small molecule reported to reduce L-Ara4N transfer onto lipid A by ArnT is an analog of LAra4N [A57], validating the L-Ara4N binding pocket as an attractive target for inhibitor development. The analog of LAra4N is not a potent inhibitor of ArnT, and illustrates the need for improved compounds. The structures of ArnTCme have revealed the atomic details of the L-Ara4N pocket, both in its apo and UndP-bound conformations. Importantly, the residues within the L-Ara4N pocket are highly conserved in Cme, *E. coli* and *S. typhimurium* (FIG. 3A-B).

Computational methods, in vivo functional assays, mutagenesis and co-crystallization experiments will be combined to develop an in-depth understanding of the interactions of L-Ara4N with its binding pocket and of the structure-activity relationship among its analogs, for designing novel ArnT inhibitors. As an initial step, the ArnT binding mode for L-Ara4N and for the analogs for which experimental data is available will be predicted, using in silico docking. The pocket residues interacting with the compounds will be validated using directed mutagenesis experiments. As a preliminary result, this approach allowed prediction of a binding mode for L-Ara4N-tri-prenyl phosphate that is very consistent with the crystallographic position of the phosphate and the first three prenyl groups of UndP. Furthermore, it pointed to specific residues as being involved in the binding of the L-Ara4N moiety. For several of these residues, functional importance has been confirmed experimentally in a recent study in *B. cenocepacia* [A58] and further in *S. typhimurium*. This iterative process will be used between computation and experiments to refine and validate predictions of the new L-Ara4N analog binding modes. Validated binding modes will in turn serve not only to explain structure-activity relationships for tested compounds, but more importantly to guide the design of optimized new ones. Using these high resolution data and functional assays in combination with cutting edge computational methods (namely free energy perturbation plus) to efficiently guide the chemical optimization of new L-Ara4N derived ArnT inhibitors will be expected to produce a series of new compounds for restoring sensitivity of MDR/resistant gram negative bacteria to polymyxin B and perhaps be effective in combination with other antibiotics for inhibiting or stopping the growth of certain gram negative bacteria.

Additionally, it is expected that in certain embodiments, the ArnT inhibitors described herein may be effective as single agents effective as single agents for inhibiting or stopping the growth of certain gram negative bacteria. In additional embodiments, any combination of at least two of the ArnT inhibitors described herein may also be effective without additional active agents for inhibiting or stopping the growth of certain gram negative bacteria.

Screening for Novel *S. typhimurium* and *E. coli* ArnT Inhibitors.

Figure 8A:
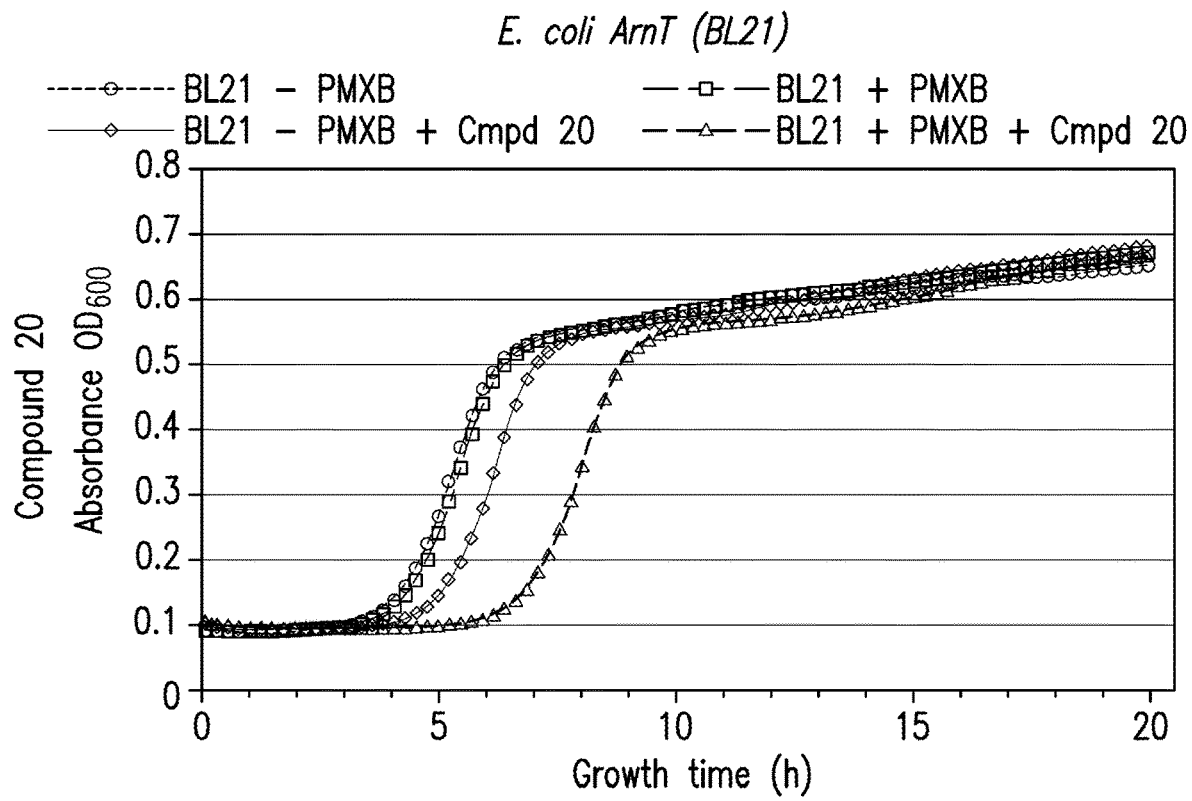
FIGS. 8A-J show graphic results of the polymyxin growth assay for the five Class I compounds obtained in target-based virtual screening. In this and all subsequent figures showing results of compound testing in the polymyxin growth assay, four curves are shown, (i) growth of test strain (BL21 for targeting E. coli ArnT or Gi24 for targeting S. typhimurium ArnT) in the absence of PMXB (−PMXB, represented by an open circle), (ii) growth of test strain in the presence of PMXB (+PMXB, represented by an open square), (iii) growth of test strain in the absence of PMXB and in the presence of test compound (−PMXB+Cmpd, represented by open diamond), and (iv) growth of test strain in the presence of PMXB and test compound (+PMXB+Cmpd, represented by an open square). Each point in the curves represents the mean of six measurements of absorbance (OD) at 600 nm (triplicate samples from two independent experiments). Standard deviation is not shown, but typically ranged from 0.001 to 0.1. Growth of E. coli BL21 strain (carrying the E. coli ArnT) was measured in the presence of Class I compounds 20, 14, 15, 19, or U2 (FIGS. 8A, 8C, 8E, 8G and 8I, respectively). Growth of E. coli Gi24 strain (carrying the S. typhimurium ArnT) was measured in the presence of Class I compounds 20, 14, 15, 19, or U2 (FIGS. 8B, 8D, 8F, 8H and 8J, respectively). All compounds were tested at a final concentration of 0.5 mM.
Figure 8B:
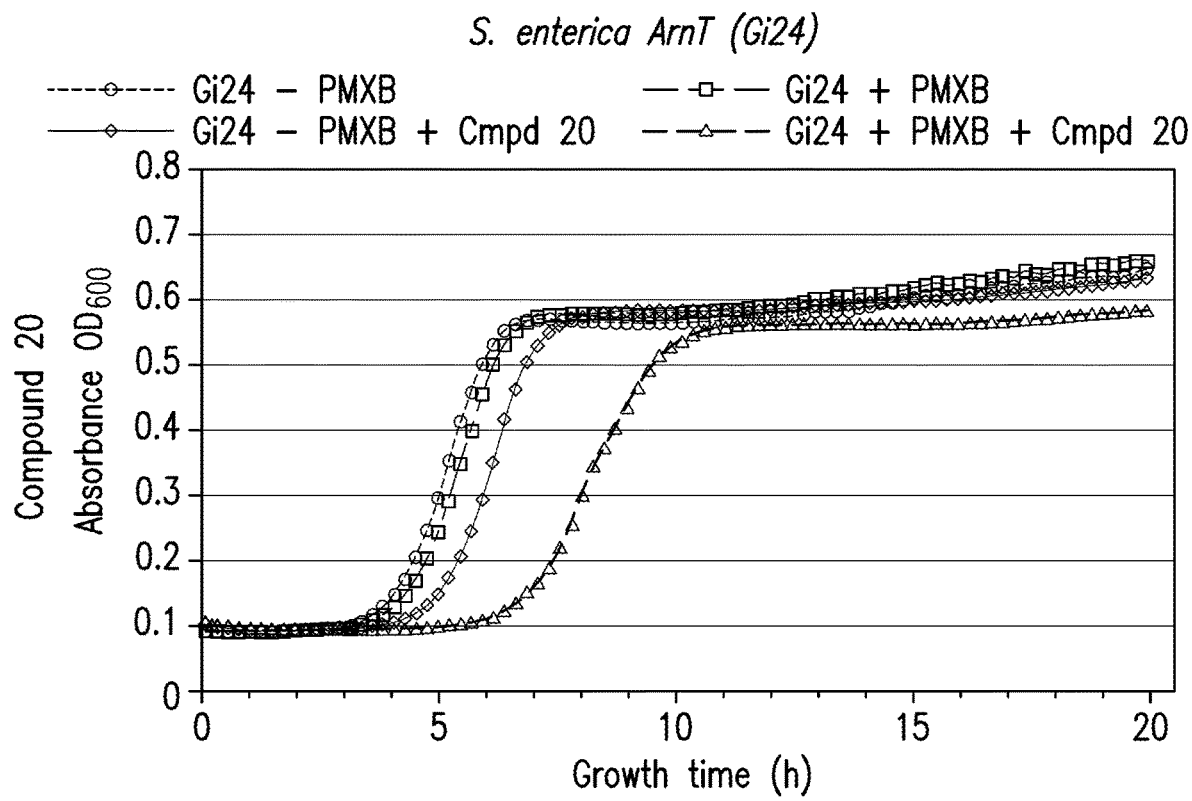
Figure 8C:
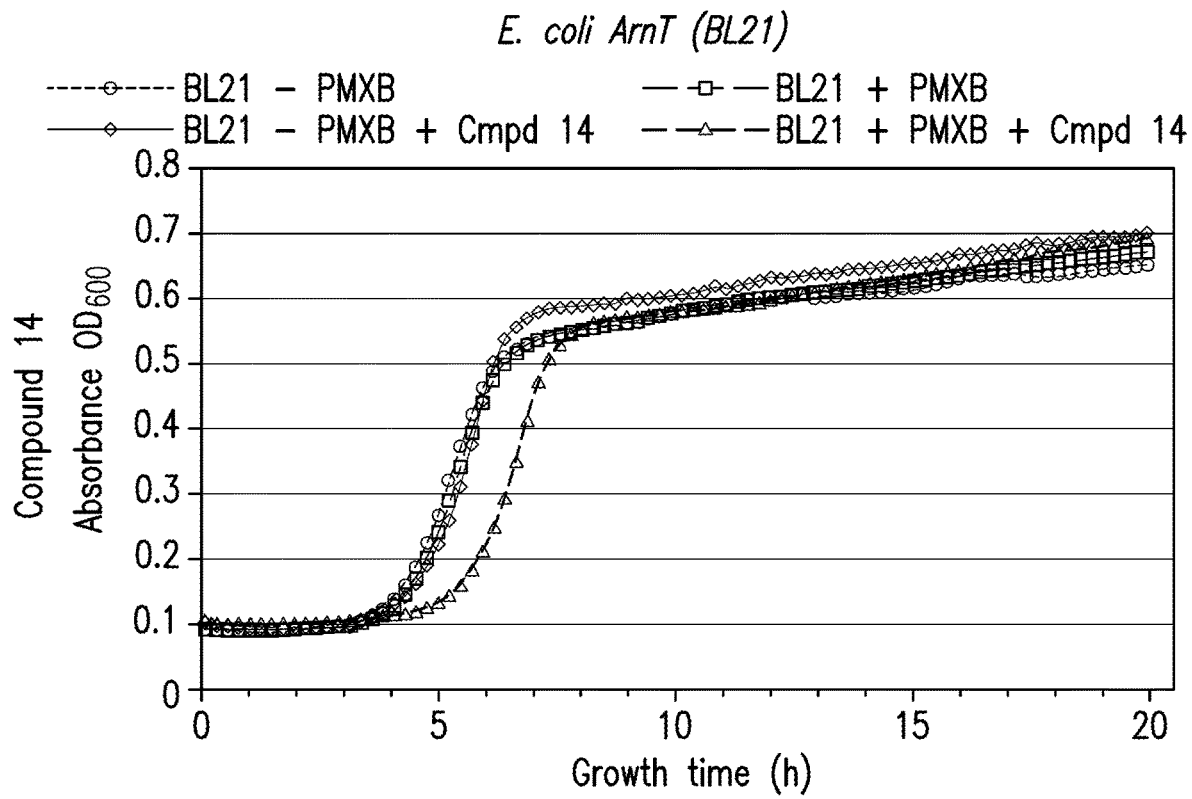
Figure 8D:
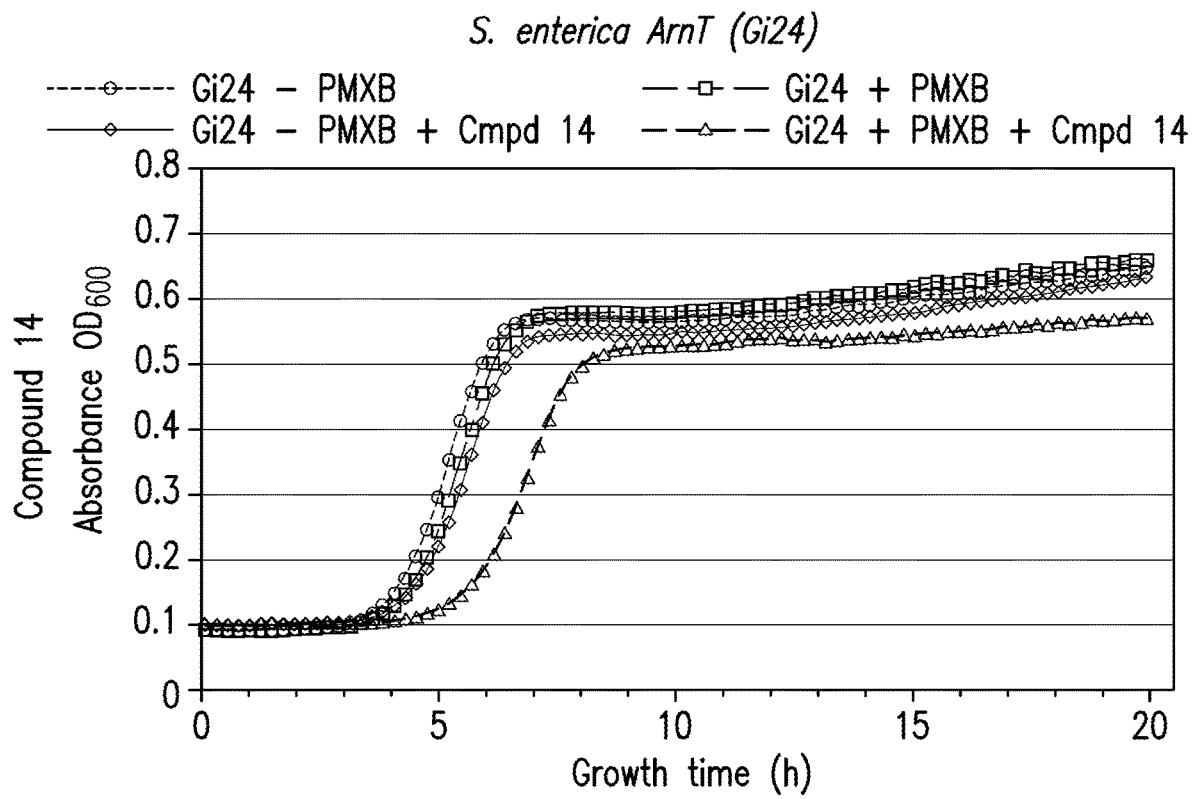
Figure 8E:
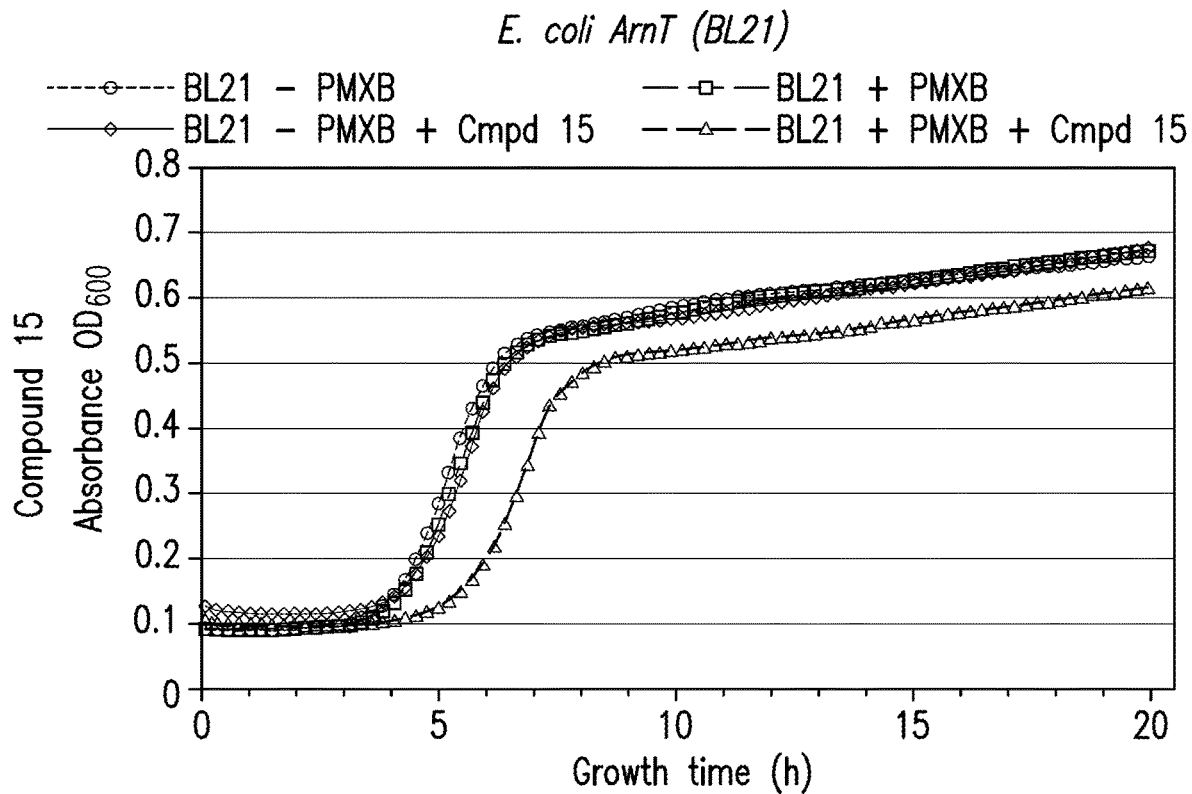
Figure 8F:
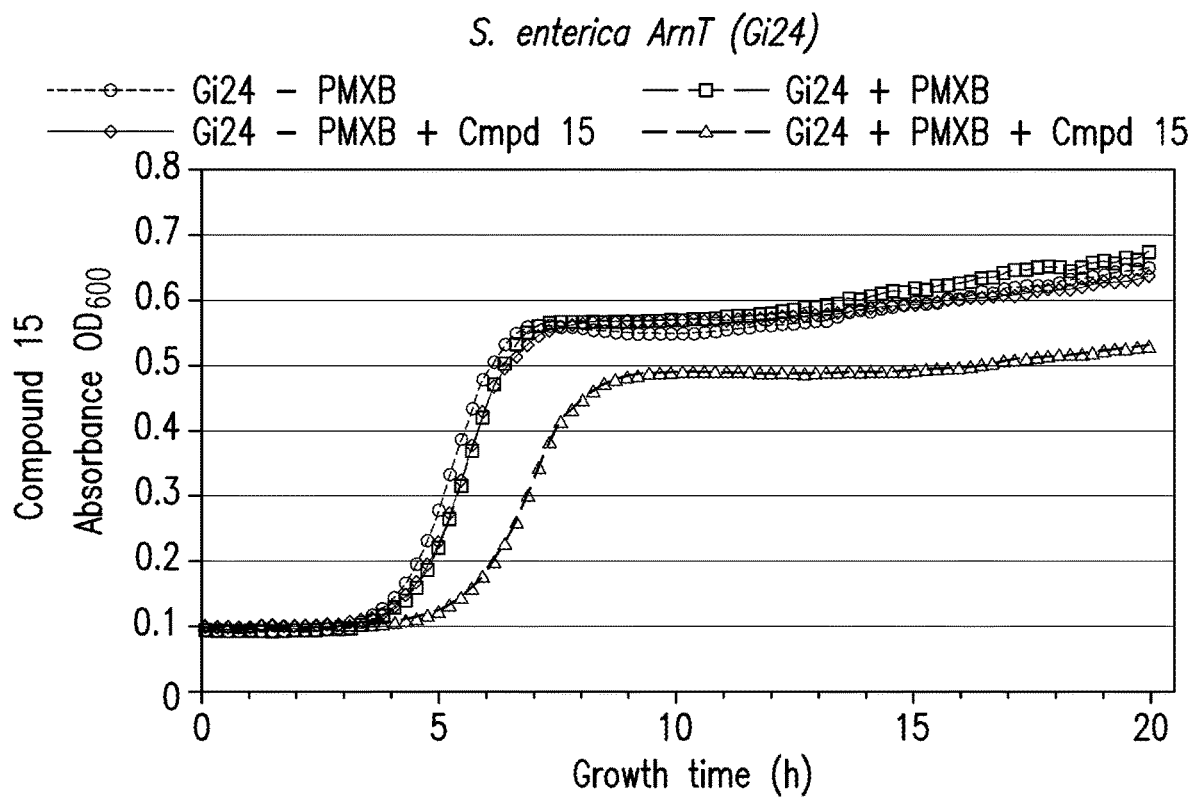
Figure 8G:
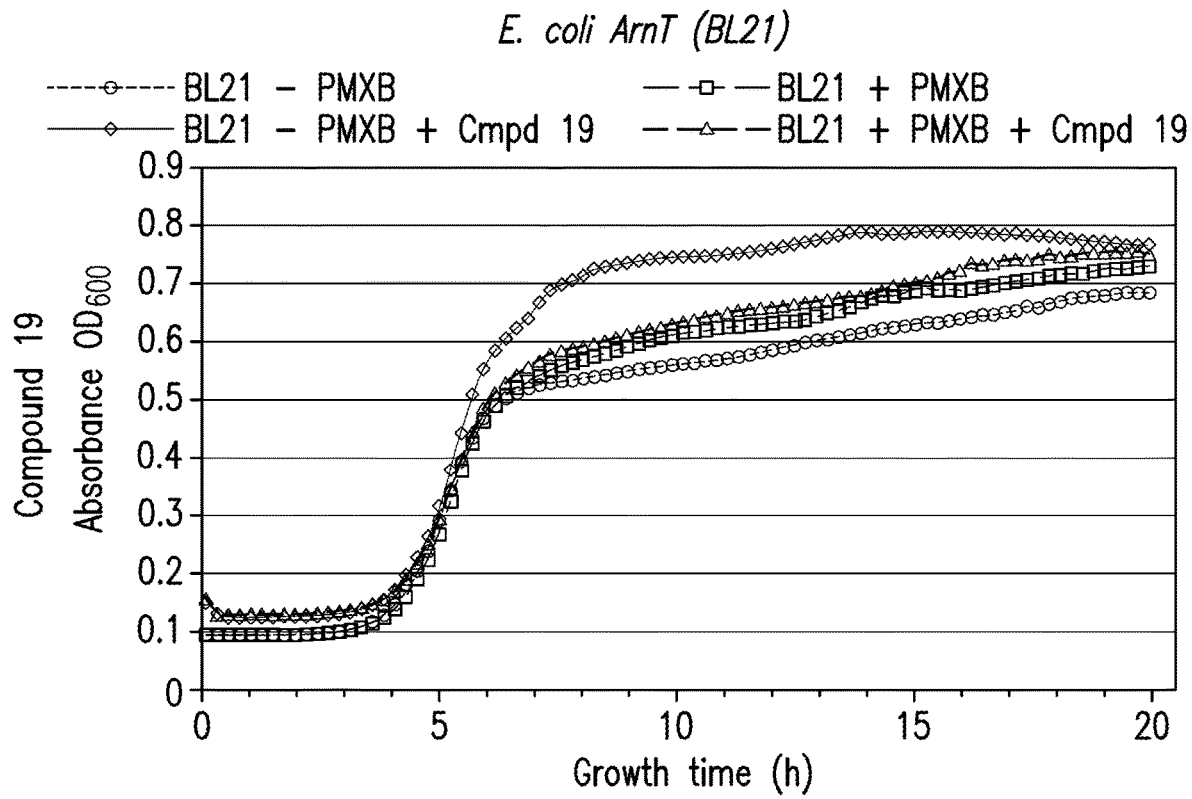
Figure 8H:
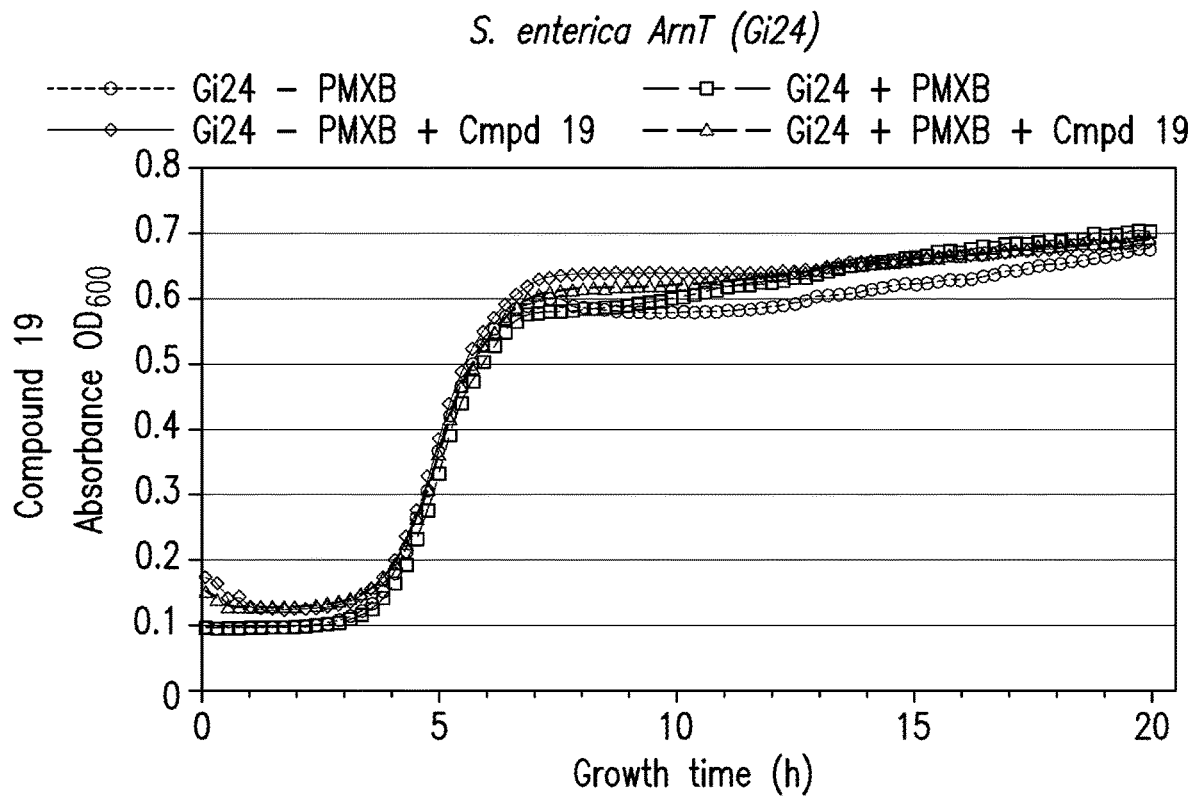
Figure 8I:
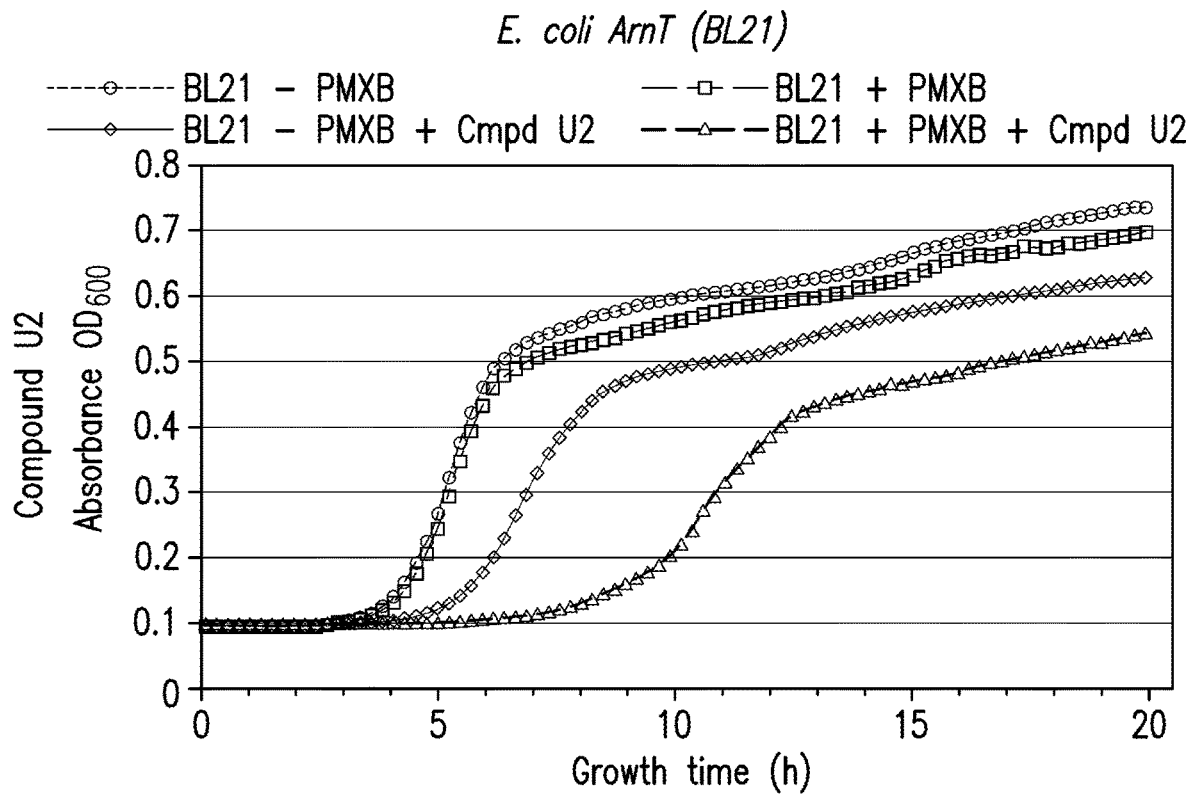
Figure 8J:
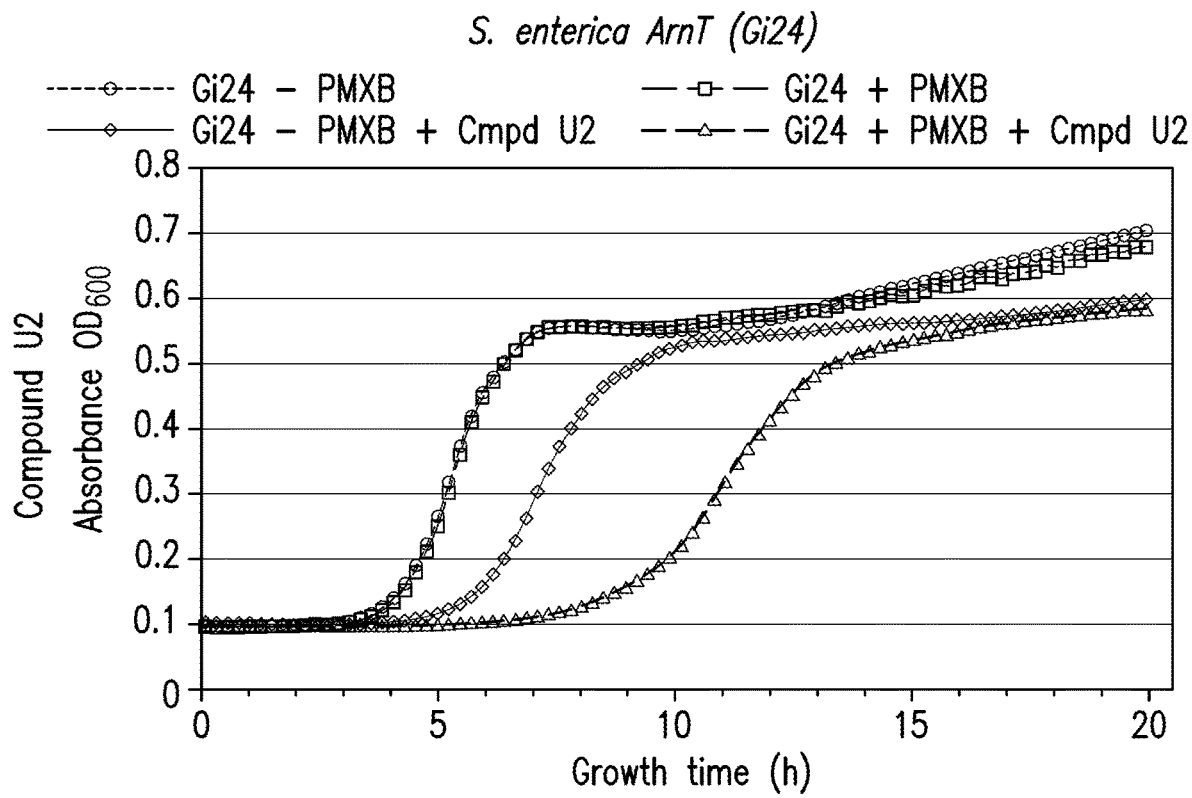
Figure 10A:
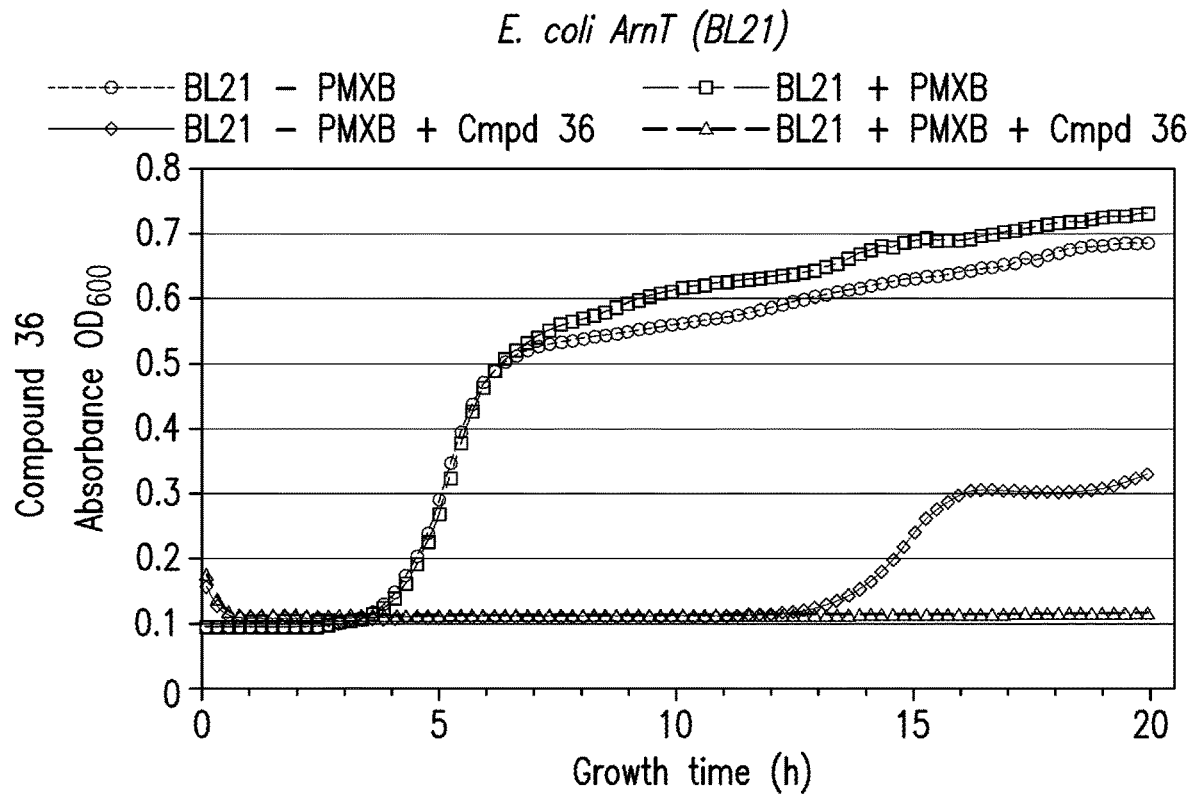
FIG. 10A-H show graphic results of the polymyxin growth assay for the four Class H compounds identified in target-based virtual screening. Each panel presents four curves as described in FIG. 8A-J. Growth of E. coli BL21 strain (carrying the E. coli ArnT) was measured in the presence of Class II compounds 36, 37, U5, or U6 (FIGS. 10A, 10C, 10E and 10G, respectively). Growth of E. coli Gi24 strain (carrying the S. typhimurium ArnT) was measured in the presence of Class II compounds 36, 37, U5, or U6 (FIGS. 10B, 10D, 10F and 10H, respectively). Each point in the curves represents the mean of six measurements of absorbance (OD) at 600 nm (triplicate samples from two independent experiments). Standard deviation is not shown, but typically ranged from 0.001 to 0.2. All compounds were tested at a final concentration of 0.5 mM.
Figure 10B:
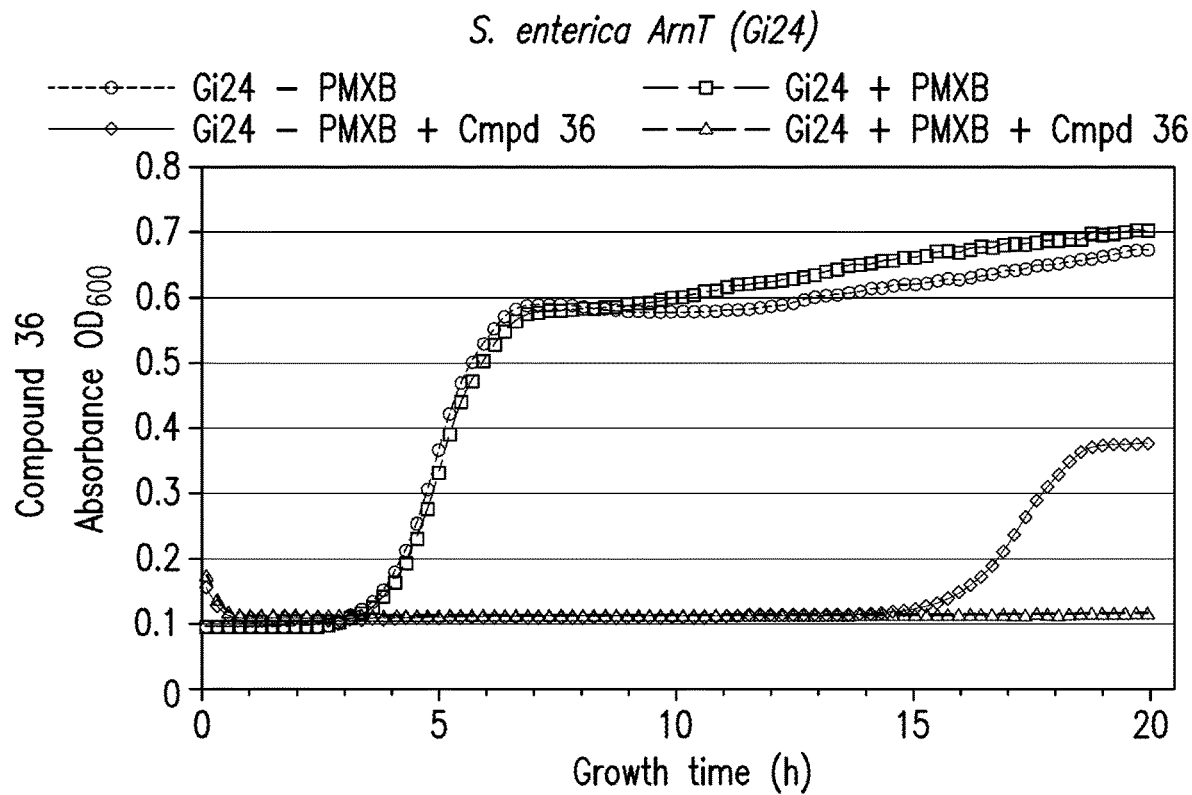
Figure 10C:
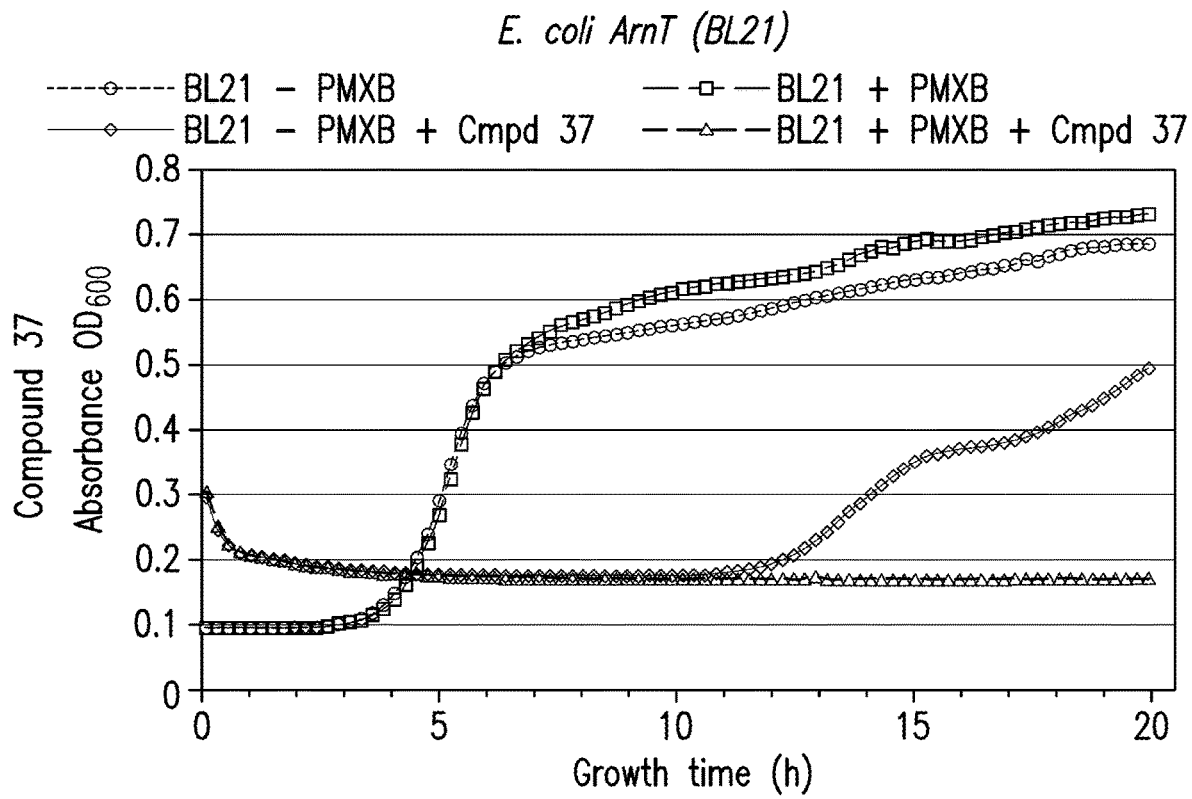
Figure 10D:
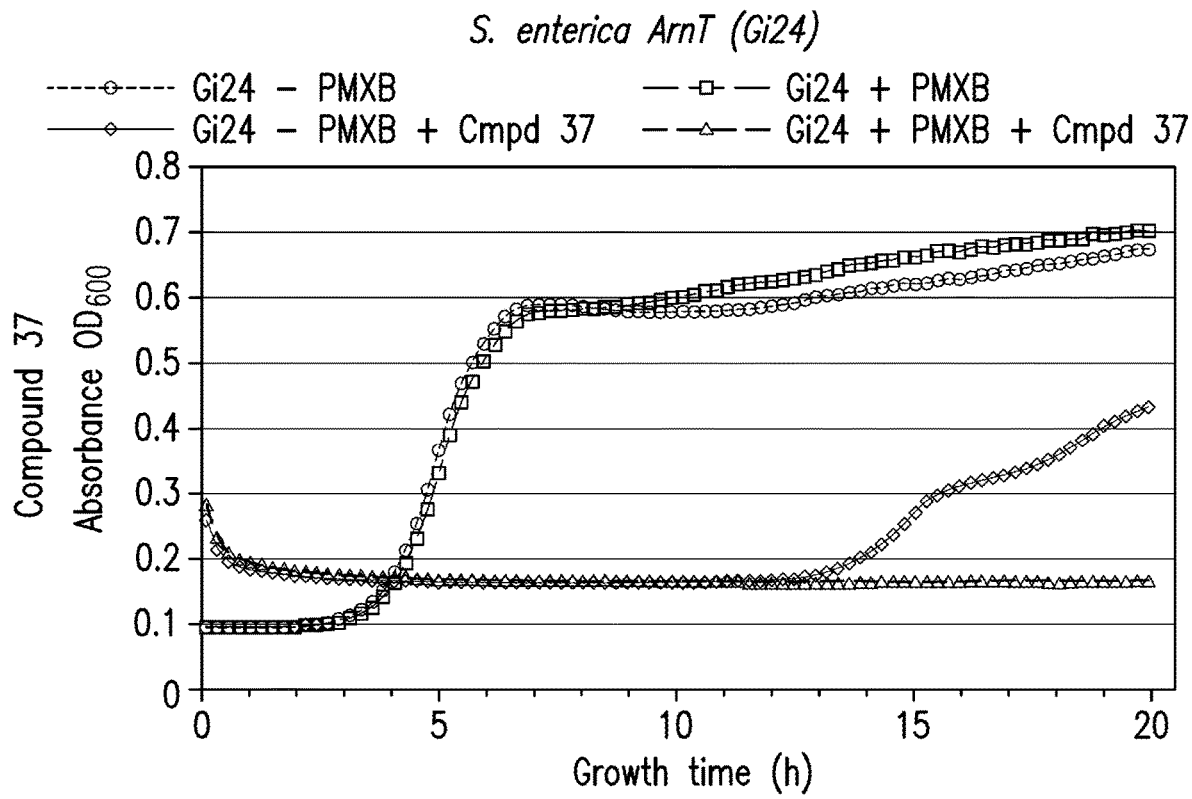
Figure 10E:
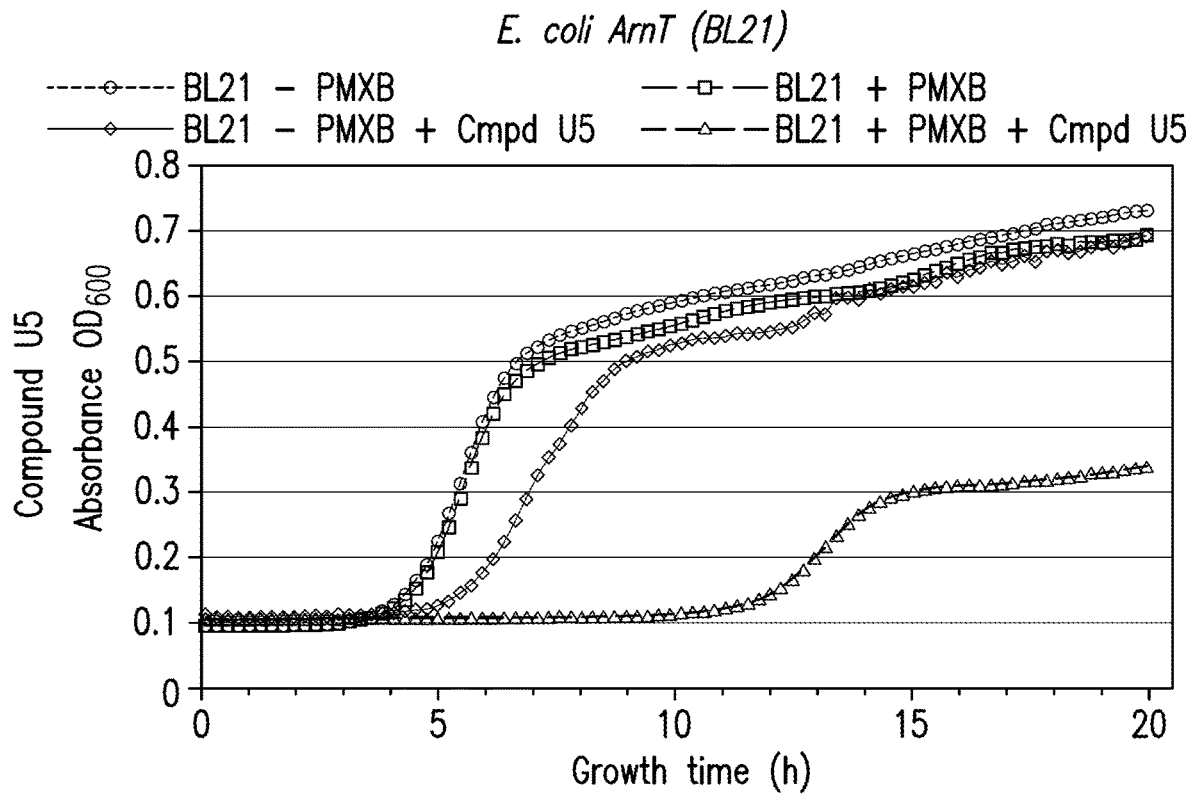
Figure 10F:
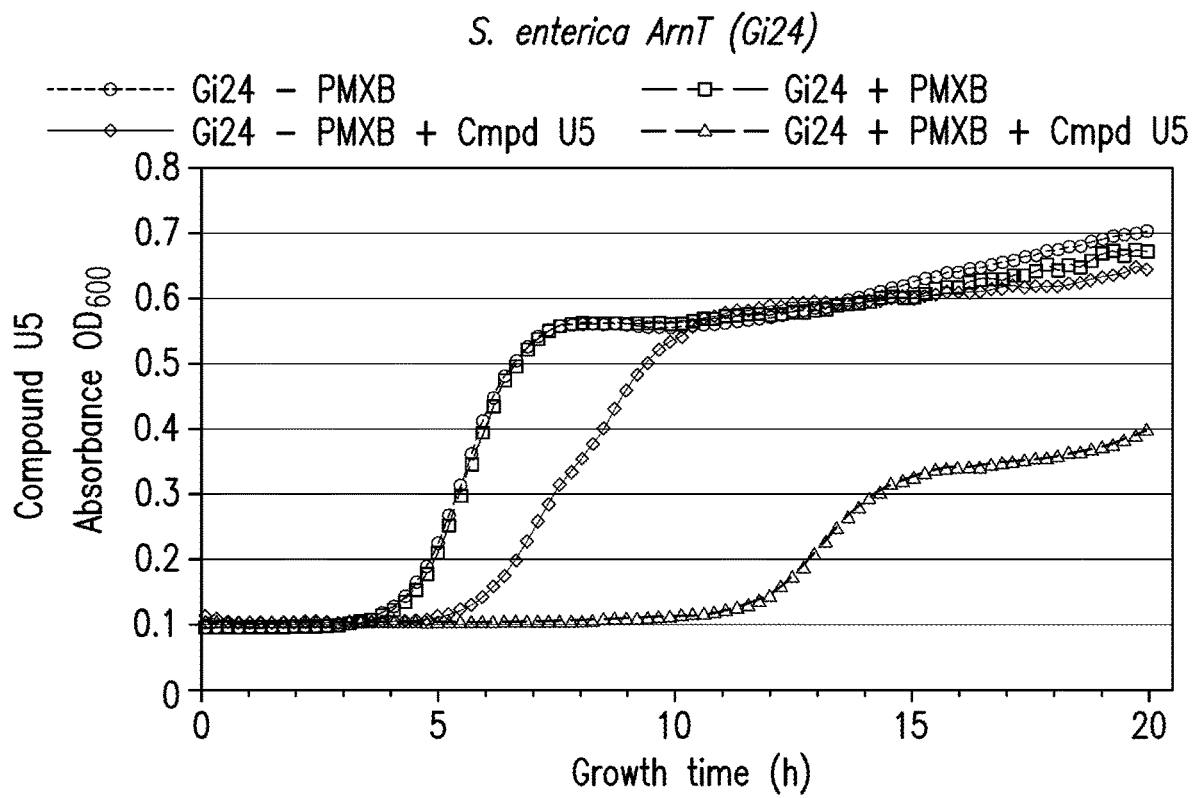
Figure 10G:
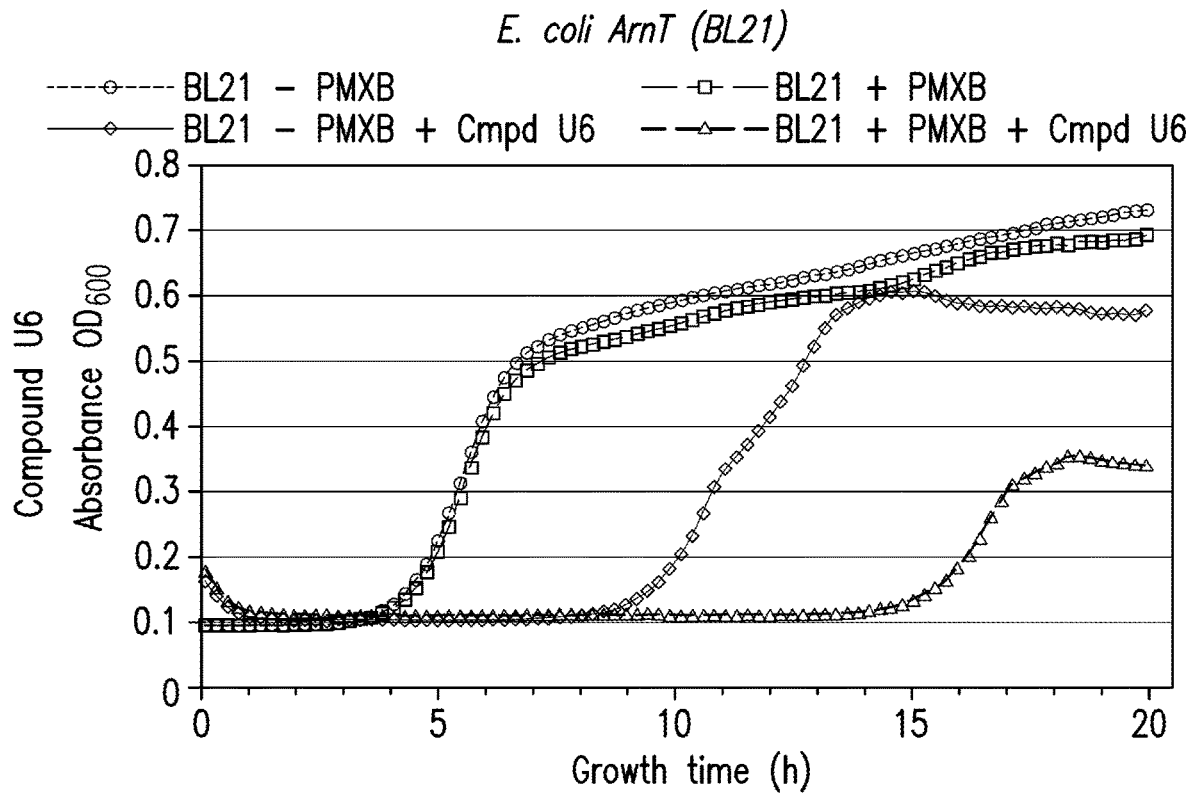
Figure 10H:
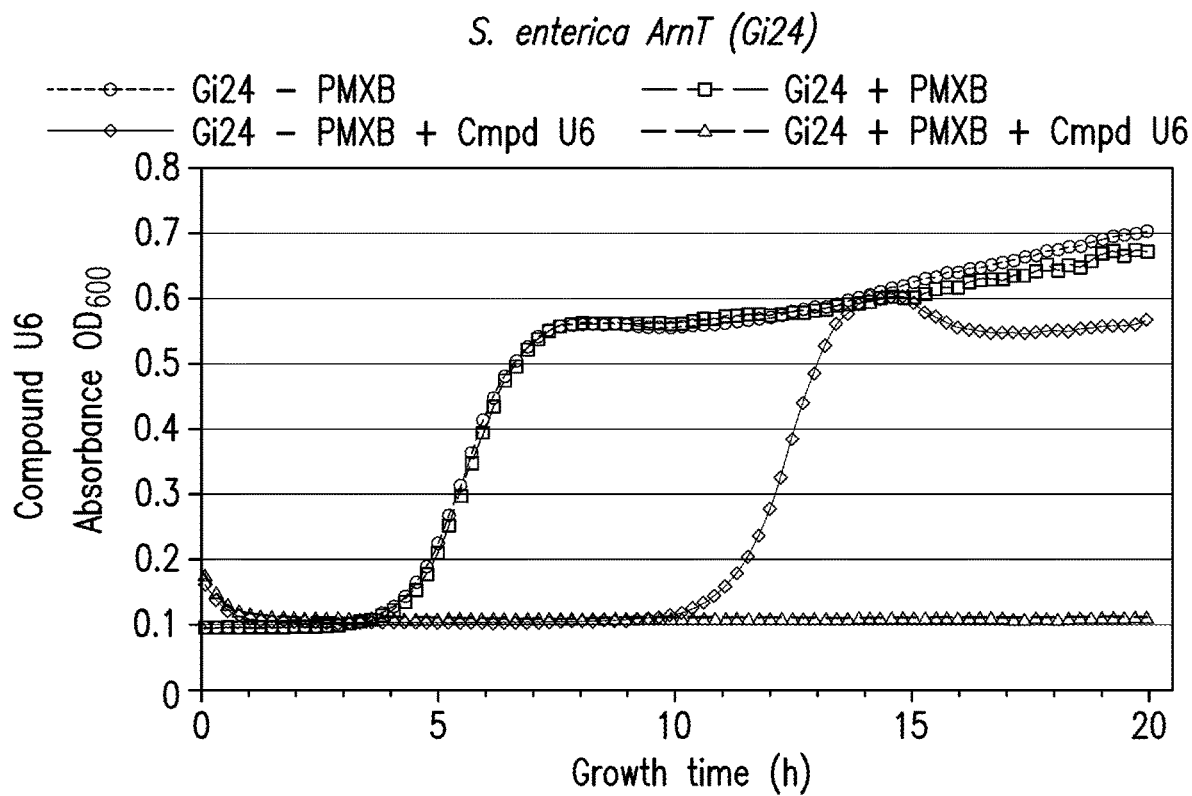
Figure 12A:
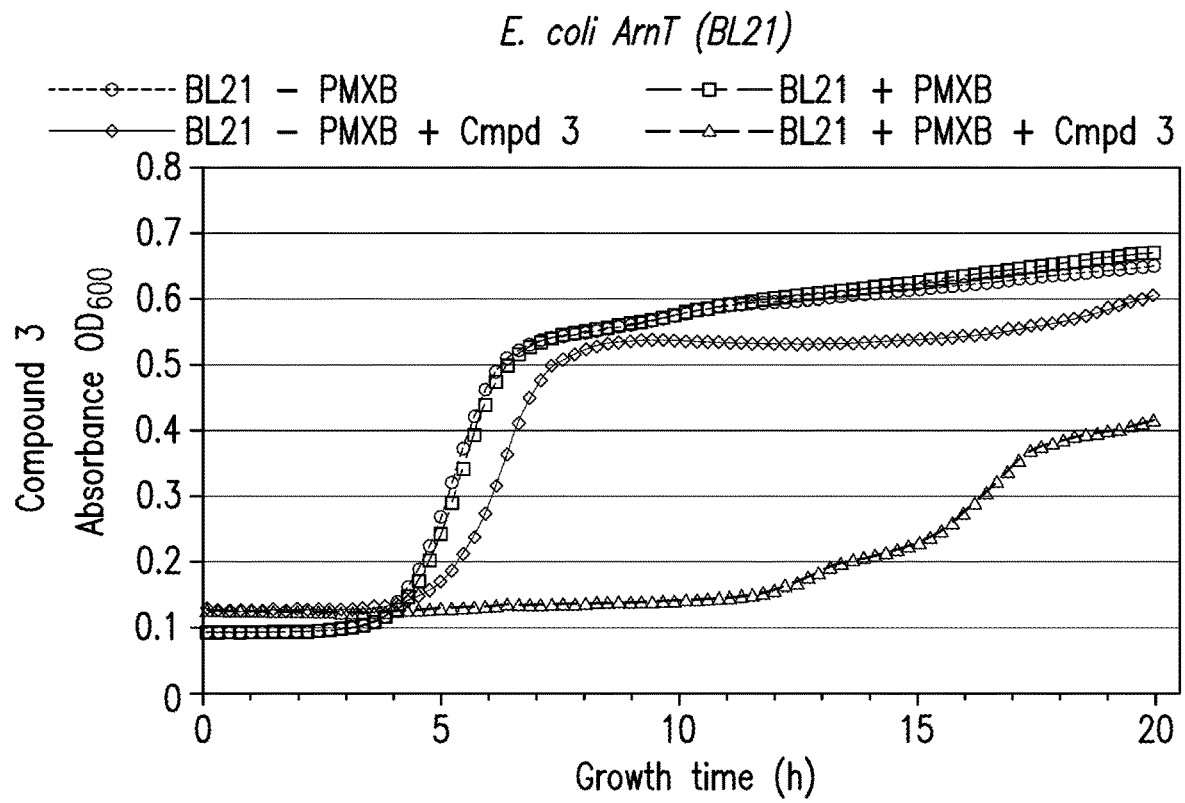
FIGS. 12A-F show graphic results of the polymyxin growth assay for the three Class III compounds obtained in target-based virtual screening. Each panel presents four curves as described in FIG. 8A-J. Growth of E. coli BL21 strain (carrying the E. coli ArnT) was measured in the presence of Class III compounds 3, U4, or U7 (FIGS. 12A, 12C and 12E, respectively). Growth of E. coli Gi24 strain (carrying the S. typhimurium ArnT) was measured in the presence of Class III compounds 3, U4, or U7 (FIGS. 12B, 12D and 12F, respectively). Results for compound 6 were omitted because irregular growth due to poor solubility does not permit confident interpretation of derived data. Only a qualitative assessment of this compound was included in FIG. 11. Each point in the curves represents the mean of six measurements of absorbance (OD) at 600 nm (triplicate samples from two independent experiments). Standard deviation is not shown, but typically ranged from 0.001 to 0.1. All compounds were tested at a final concentration of 0.5 mM.
Figure 12B:
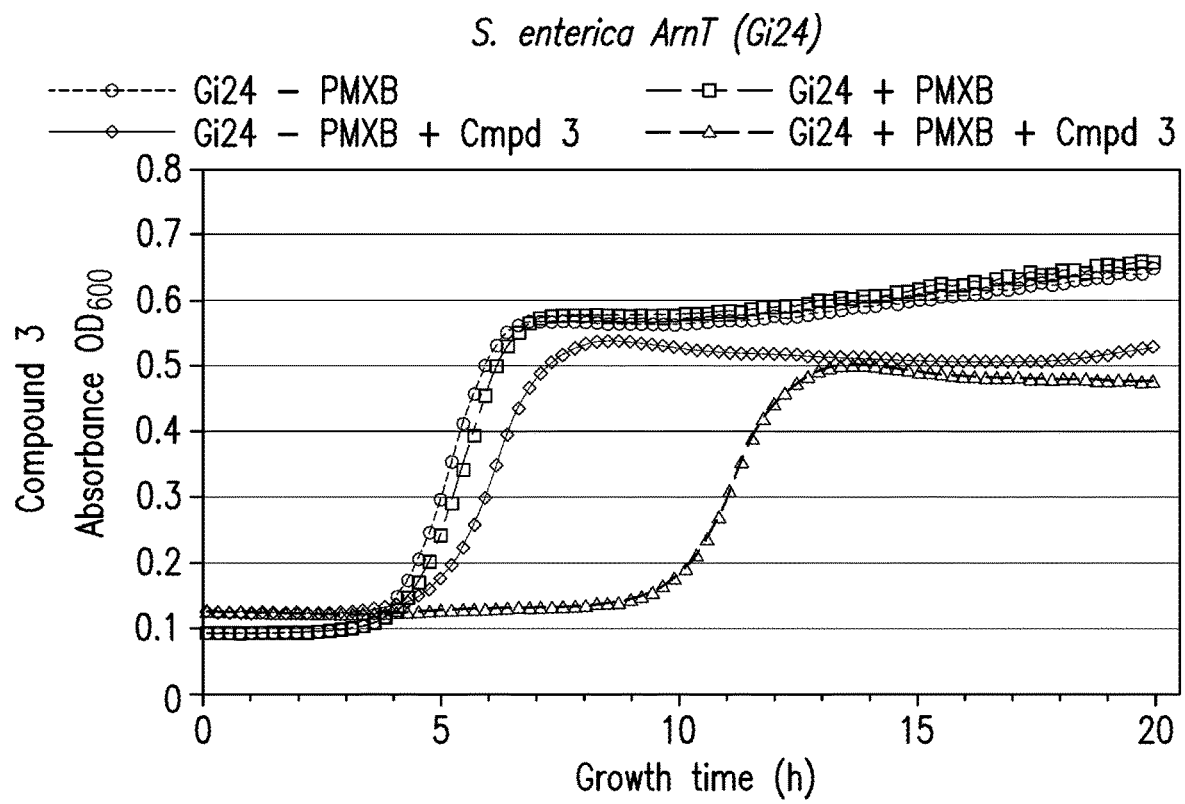
Figure 12C:
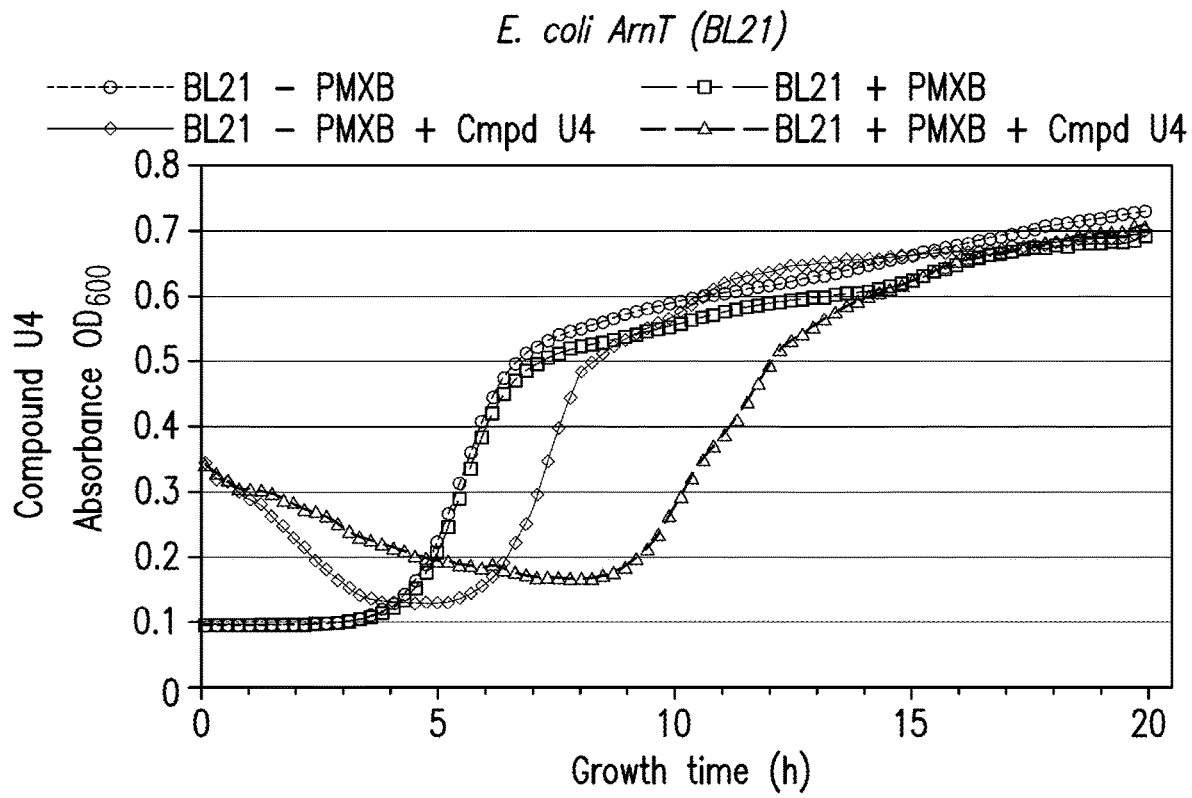
Figure 12D:
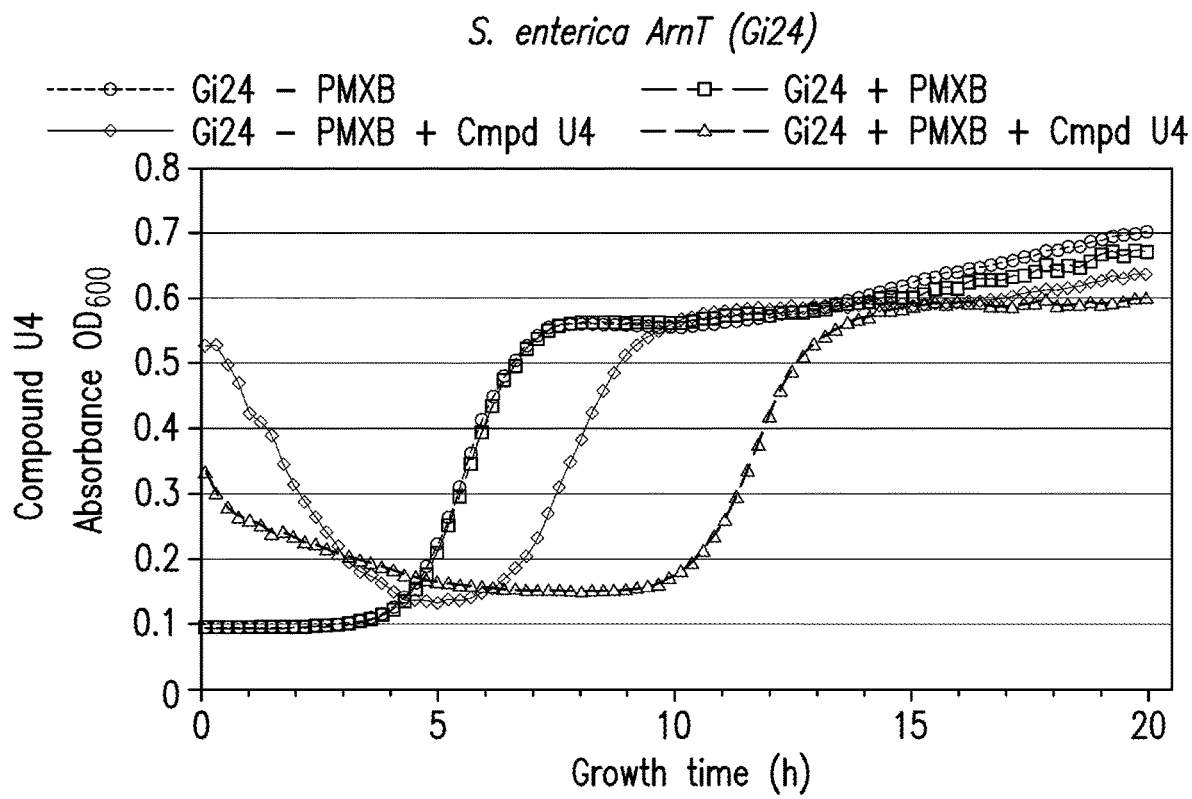
Figure 12E:
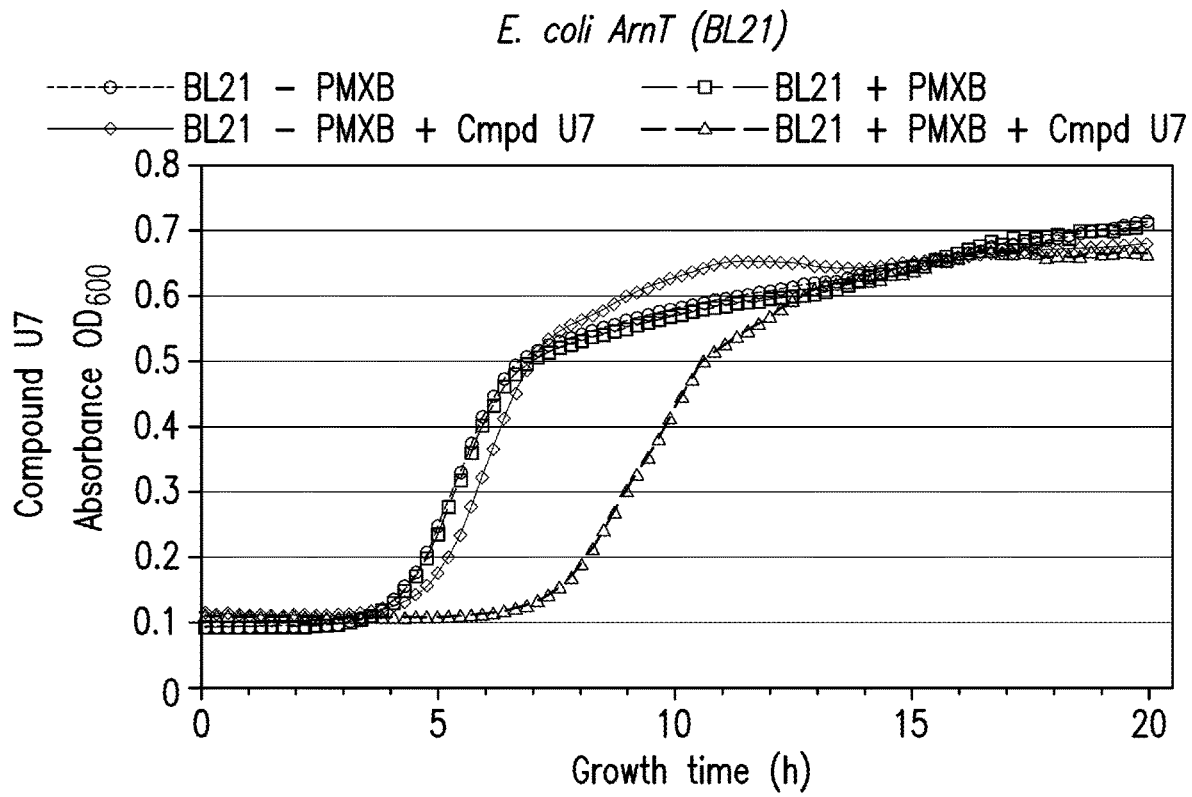
Figure 12F:
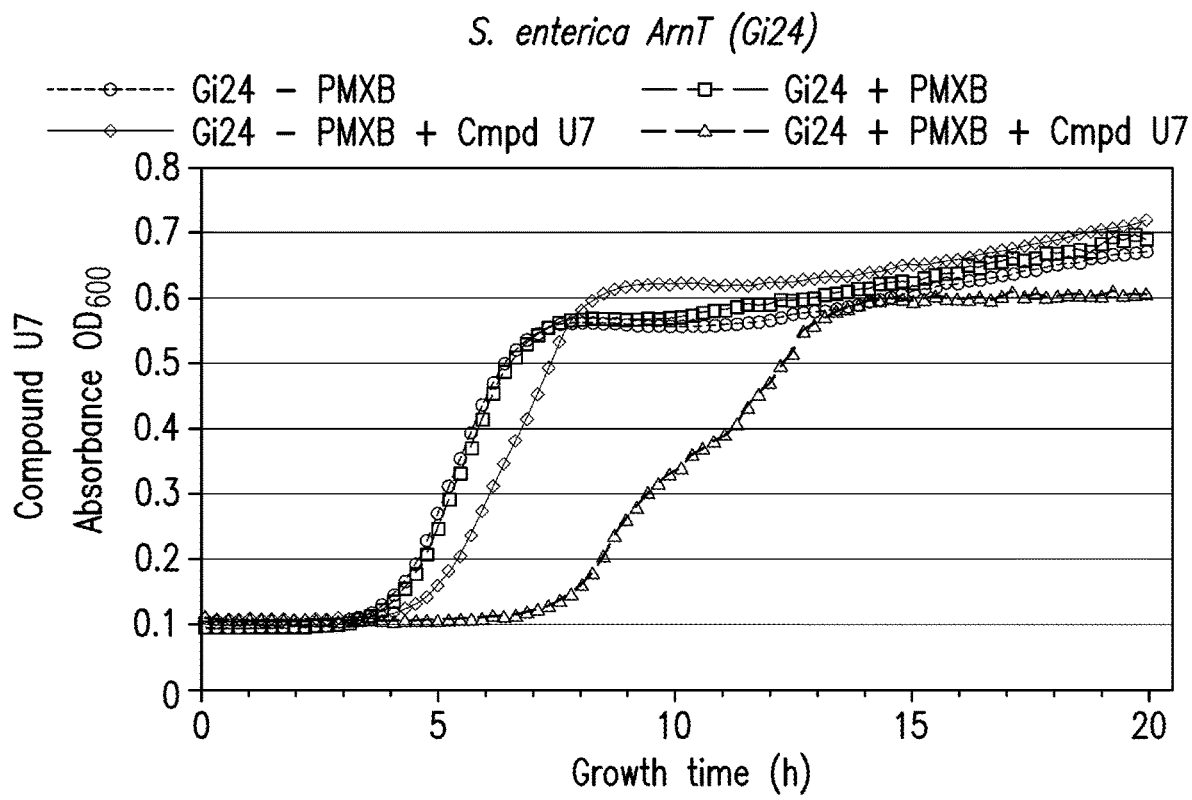
Figure 14A:
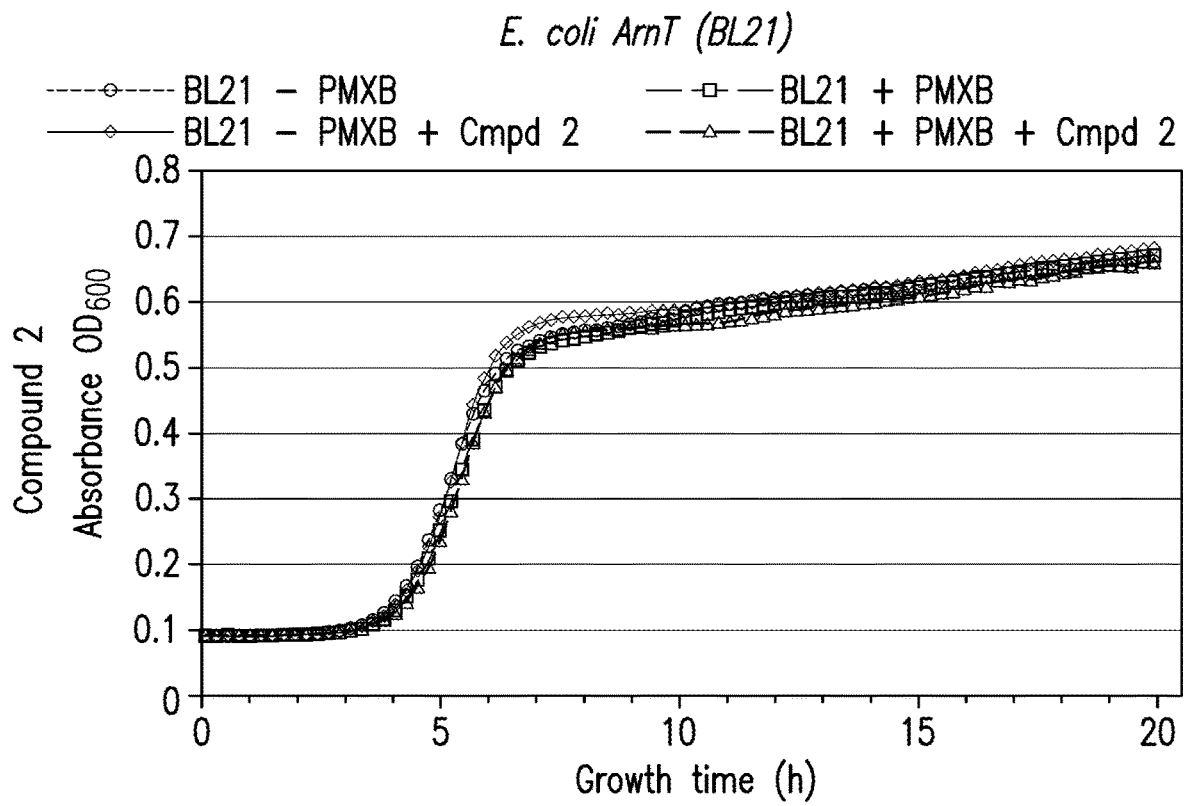
FIGS. 14A-D show graphic results of the polymyxin growth assay for the two Class IV compounds obtained in target-based virtual screening. Each panel presents four curves as described in FIG. 8A-J. Growth of E. coli BL21 strain (carrying the E. coli ArnT) was measured in the presence of Class IV compounds 2 or 9 (FIGS. 14A and 14C, respectively). Growth of E. coli Gi24 strain (carrying the S. typhimurium ArnT) was measured in the presence of Class 1 compounds 2 or 9 (FIGS. 14B and 14D, respectively). Each point in the curves represents the mean of six measurements of absorbance (OD) at 600 nm (triplicate samples from two independent experiments). Standard deviation is not shown, but typically ranged from 0.001 to 0.1. All compounds were tested at a final concentration of 0.5 mM.
Figure 14B:
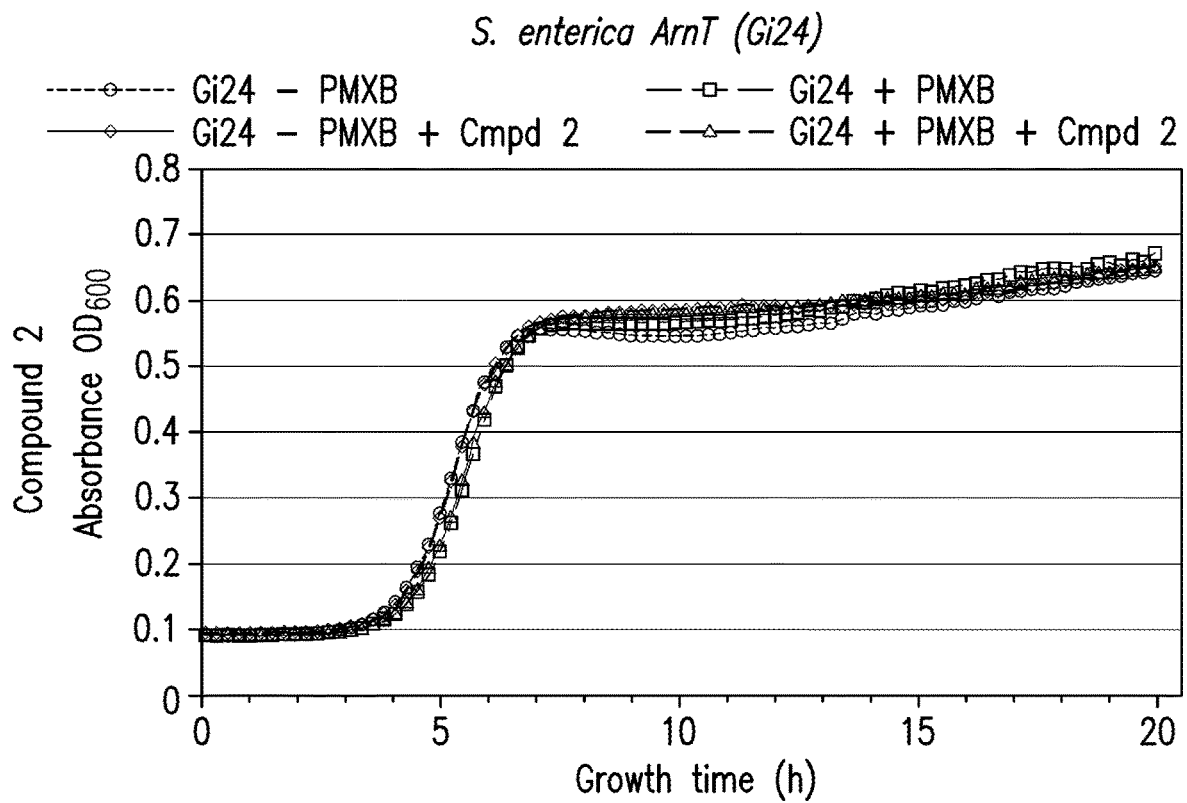
Figure 14C:
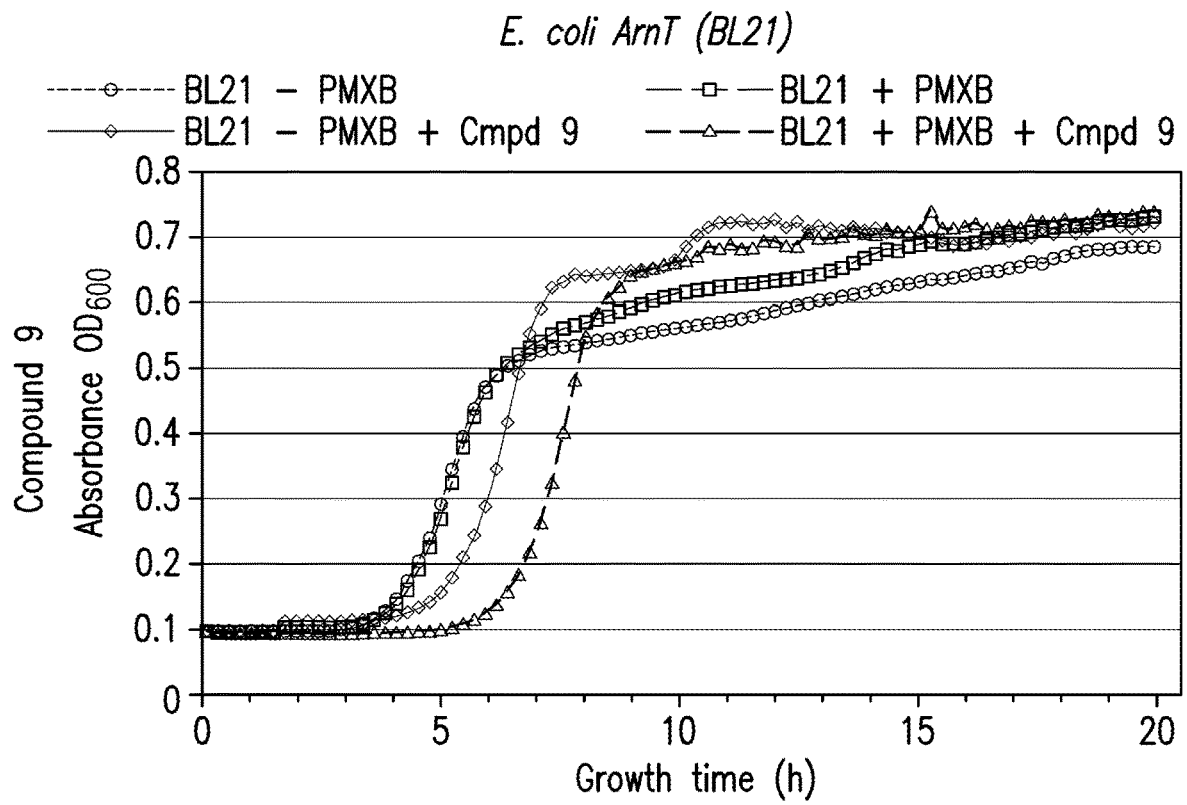
Figure 14D:
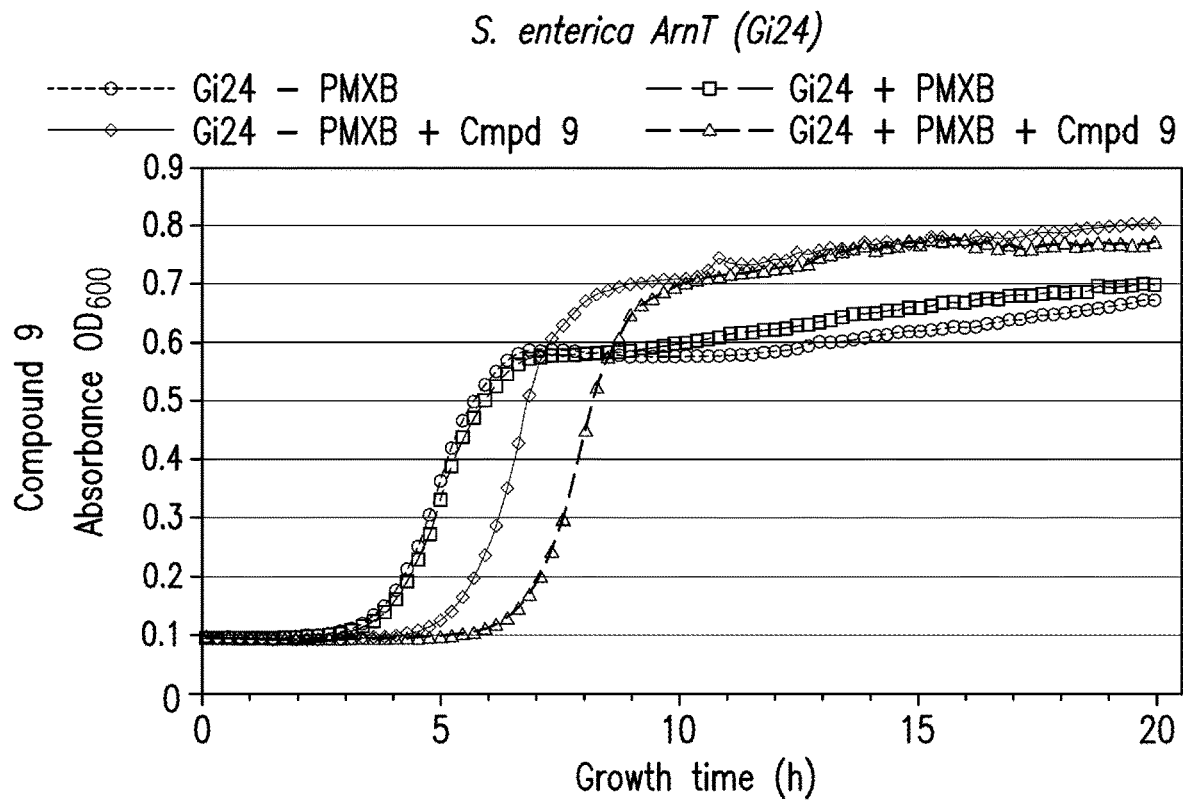

Only one small molecule with some ArnT inhibiting activity has been reported so far [57]. A polymyxin growth assay will allow for testing the inhibiting activity of compounds on ArnT from both *E. coli* and *S. typhimurium*. In parallel with the design of potent L-Ara4N derived inhibitors (described above), and in order to discover more diverse small molecules that can serve as the basis for further development, a large-scale structure-guided search for new ArnT inhibitors is being conducted. An in-house virtual library of small molecule comprising more than 22 million compounds will be utilized in combination with a high-throughput in silico pipeline consisting of three successive docking steps with increasing accuracy, to perform a target-based screening for potential small molecules inhibitors of ArnT. The L-Ara4N pocket will be specifically targeted as it adjoins the catalytic site and forms a "druggable" cavity. The high-resolution structures of ArnTCm in the apo and the UndP-bound conformation will both serve as structural target since both are relevant functional states for inhibition. Structures resulting from the approach described herein will be used as structural targets as well. An initial virtual screening of about 2 million compounds on both the Apo and the UndP-bound conformations of the L-Ara4N pocket has been performed. More than 1500 (highly scoring virtual hits have been obtained, most on the UndP-bound structure, but many also on the Apo conformation. Clustering of these virtual hits based on chemical similarity shows that while a fraction of them are similar to the natural substrate of the pocket, L-Ara4N, a variety of new chemical scaffolds were identified. Further filtering and selection was performed. While compounds in the most populated chemical clusters are particularly attractive candidates for initial testing, we also selected compounds from less populated clusters to ensure the chemical diversity of the virtual hits obtained. A very first short list of 80 compounds has been selected through this process. Screening and testing results show that one compound designated Class I compound 20:

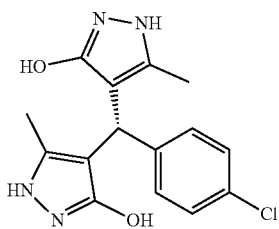

and named 4,4'-[(4-chlorophenyl)methylene]bis(3-methyl-1H-pyrazol-5-ol, shows especially strong ArnT inhibiting activity (FIGS. 8A-B).

In total. Four Classes of compounds, with 15 representative specific compounds have been identified, as listed in the tables of FIGS. 7, 9, 11, and 13. Details of the structures of the compounds are provided below.

Class 1/Formula I

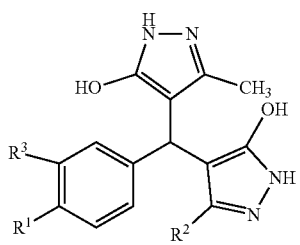

In general Class I compounds are encompassed by the following:
wherein:
$R^1$ is selected from chloro, fluoro, OH, straight and branched alkyl of 1 to 6 carbon atoms with 1 to 3 carbon atoms preferred and dialkylamino of the formula —$NR^3R^4$ where $R^3$ and $R^4$ are independently selected from hydrogen, straight and branched alkyl of 1 to 6 carbon atoms with 1 to 3 carbon atoms preferred:
$R^2$ is straight and branched alkyl of 1 to 3 carbon atoms;
$R^3$ is H, straight and branched alkyl of 1 to 3 carbon atoms, OH and nitro: or a pharmaceutically acceptable salt thereof.

The compounds of Formula I may be obtained as inorganic or organic pharmaceutically acceptable salts using methods known to those skilled in the art (Richard C. Larock, Comprehensive Organic Transformations, VCH Publishers, 411-415, 1989). It is well known to one skilled in the art that an appropriate salt which include but not limited to inorganic salts which may be sodium, calcium, potassium or magnesium and the like or equivalent thereof or hydrochloric, hydrobromic, hydroiodic, phosphoric, nitric or sulfate and the like.

Specific Examples of Formula I/Class I Compounds Include (Also Shown in FIGS. 7A-B):
Compound 20:
4-[(4-chlorophenyl)-(3-methyl-5-oxo-1,2-dihydropyrazol-4-yl)methyl]-5-methyl-1,2-dihydropyrazol-3-one;
Compound 14:
5-methyl-4-[(3-methyl-5-oxo-1,2-dihydropyrazol-4-yl)-(4-propan-2-ylphenyl)methyl]-1,2-dihydropyrazol-3-one:
Compound 15:
4-[[4-(dimethylamino)phenyl]-(3-methyl-5-oxo-1,2-dihydropyrazol-4-yl)methyl]-5-methyl-1,2-dihydropyrazol-3-one;
Compound 19:
4-[(S)-(3,4-dihydroxyphenyl)-(3-methyl-5-oxo-1,2-dihydropyrazol-4-yl)methyl]-5-methyl-1H-pyrazol-3-olate; and
Compound U2:
4-[(4-hydroxy-3-nitrophenyl)-(3-methyl-5-oxo-1,2-dihydropyrazol-4-yl)methyl]-5-methyl-1,2-dihydropyrazol-3-one.

Class II/Formula II

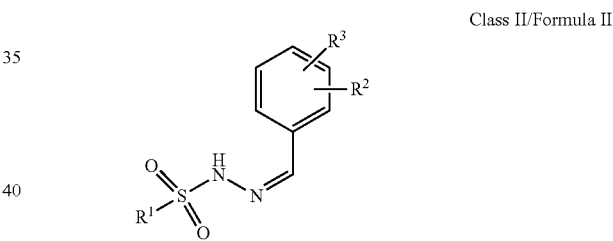

In general Class II compounds are those wherein:
$R^1$ is a moiety selected from the group:

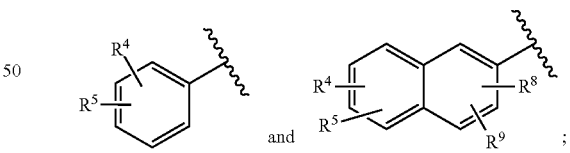

$R^2$, $R^3$, $R^4$, $R^5$, $R^8$ and $R^9$ are independently selected from hydrogen, hydroxyl, amino, fluoro, chloro, straight chain alkyl of 1 to 6 carbon atoms, branched chain alkyl of 3 to 7 carbon atoms, nitro and —$NR^6R^7$ where $R^6$ and $R^7$ are independently selected from hydrogen, straight and branched alkyl of 1 to 6 carbon atoms with 1 to 3 carbon atoms preferred; or a pharmaceutically acceptable salt thereof.

The compounds of Formula II may be obtained as inorganic or organic pharmaceutically acceptable salts using methods known to those skilled in the art (Richard C. Larock, Comprehensive Organic Transformations, VCH Publishers, 411-415, 1989). It is well known to one skilled in the art that an appropriate salt which include but not limited to inorganic salts which may be sodium, calcium, potassium or magnesium and the like or equivalent thereof or hydrochloric, hydrobromic, hydroiodic, phosphoric, nitric or sulfate and the like.

Specific Examples of Formula I/Class II Compounds Include (as Shown in FIG. 9):
Compound 36:
N'-[(3-hydroxy-4-oxocyclohexa-2,5-dien-1-ylidene) methyl]-4-propylbenzenesulfonohydrazide:
Compound 37:
N'-[(3-hydroxy-4-oxocyclohexa-2,5-dien-1-ylidene) methyl]-4-(2-methylpropyl)benzenesulfonohydrazide;
Compound U5:
N'-[(5-hydroxy-6-oxocyclohexa-2,4-dien-1-ylidene)methyl] naphthalene-2-sulfonohydrazide; and
Compound U6:
N'-[(5-hydroxy-6-oxocyclohexa-2,4-dien-1-ylidene) methyl]-4-(2-methylpropyl)benzenesulfonohydrazide.

Class/Formula III

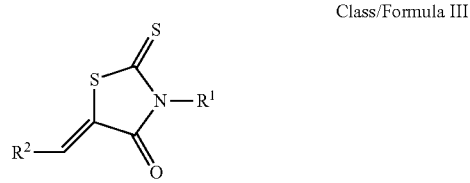

In general Class III compounds are those wherein:
$R^1$ is a moiety —$(CH_2)_n$-COOH;
n is 1 to 3;
$R^2$ is selected from moieties of the group

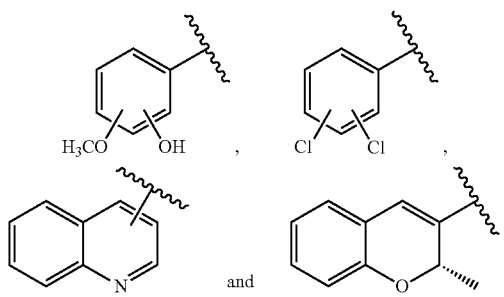

or a pharmaceutically acceptable salt thereof.

The compounds of Class/Formula III may be obtained as inorganic or organic pharmaceutically acceptable salts using methods known to those skilled in the art (Richard C. Larock, Comprehensive Organic Transformations, VCH Publishers. 41 1415, 1989). It is well known to one skilled in the art that an appropriate salt which include but not limited to inorganic salts which may be sodium, calcium, potassium or magnesium and the like or equivalent thereof or hydrochloric, hydrobromic, hydroiodic, phosphoric, nitric or sulfate and the like.

Specific Examples of Formula III/Class III Compounds Include (as Shown in FIG. 11):
Compound 3:
2-[(5E)-5-[(2-hydroxy-3-methoxyphenyl)methylidene]-4-oxo-2-sulfanylidene-1,3-thiazolidin-3-yl]acetate;
Compound 6:
2-[(5Z)-4-oxo-5-(quinolin-4-ylmethylidene)-2-sulfanylidene-1,3-thiazolidin-3-yl]acetate;

Compound U4:
2-[(5Z)-5-[(3,4-dichlorophenyl)methylidene]-4-oxo-2-sulfanylidene-1,3-thiazolidin-3-yl]acetic acid; and
Compound U7:
3-[(5E)-5-[[(2S)-2-methyl-2H-chromen-3-yl]methylidene]-2,4-dioxo-1,3-thiazolidin-3-yl]propanoic acid.

Class/Formula IV

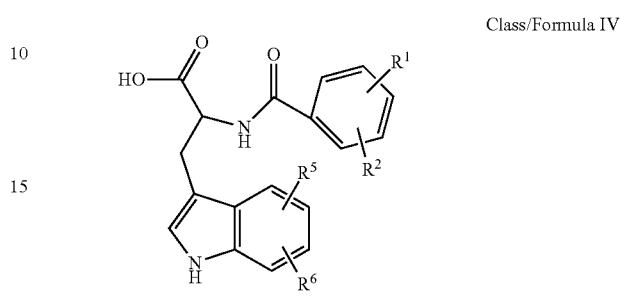

In general Class IV compounds are those wherein:
$R^1$ and $R^2$ and $R^5$ and $R^6$ are independently selected from hydrogen, fluoro, chloro, straight chain alkyl of 1 to 6 carbon atoms, branched chain alkyl of 3 to 7 carbon atoms and —$NR^3R^4$ where $R^3$ and $R^4$ are independently selected from hydrogen, and straight and branched alkyl of 1 to 6 carbon atoms, or a pharmaceutically acceptable salt thereof.

The compounds of Formula IV may be obtained as inorganic or organic pharmaceutically acceptable salts using methods known to those skilled in the art (Richard C. Larock, Comprehensive Organic Transformations, VCH Publishers, 411-415, 1989). It is well known to one skilled in the art that an appropriate salt which include but not limited to inorganic salts which may be sodium, calcium, potassium or magnesium and the like or equivalent thereof or hydrochloric, hydrobromic, hydroiodic, phosphoric, nitric or sulfate and the like.

Specific Examples of Formula IV/Class IV Compounds Include (as Shown in FIG. 13):
Compound 2:
(2S)-3-(1H-indol-3-yl)-2-[(4-methylbenzoyl)amino]propanoate; and
Compound 9:
(2S)-2-[(2,4-difluorobenzoyl)amino]-3-(1H-indol-3-yl)propanoate.

The aim of the polymyxin growth assay used for compound screening is to identify compounds that are capable of reverting resistance to polymyxin-class antibiotics in Gram-negative bacteria. Thus, retardation of growth of polymyxin resistant strains (BL21 and Gi24) in the presence of polymyxin B (PMXB) is the major hallmark that was used to identify compounds that are active against the ArnT protein responsible in large part for conferring polymyxin resistance to Gram-negative bacteria. This attribute can be observed in varying degrees in the growth results presented for compound classes I, II, III and IV in FIGS. 8, 10, 12 and 14 respectively, as a right shift of the growth curve in time when both PMXB and the corresponding compound are present. Moreover, the so called "off-target" effects represent a partial action of the compound itself (in the absence of PMXB) on the growth of polymyxin resistant strains, which may correspond to an "antibiotic-like" effect of the compounds that exists in addition to their activity as ArnT inhibitors. Further exploration of these effects (specific and off-target) through hit optimization strategies designed to increase efficacy of the compound classes described herein is expected to lead to derivative compounds that are capable of reversing polymyxin resistance and thus lead to clearance of infections under clinical conditions when used either alone or in combination of polymyxin-class antibiotics.

This structure-based drug design of ArnT inhibitors, combined with medicinal chemistry techniques will serve to develop novel compounds for restoring polymyxin susceptibility in resistant GN pathogens. Importantly, it is expected that positive results from this work will not only to be beneficial for combatting drug resistant/MDR infections from bacteria such as *E. coli* and *S. typhimurium* but from a large spectrum of GN bacteria including those from the Enterobacteriaceae and Gammaproteobacteria, for example.

Materials and Methods

Target Identification and Cloning

Twelve target ArnT genes corresponding to a wide genomic background were identified based on a bioinformatics approach (26). Ligation independent cloning (LIC) was used to clone the targets into four different LIC-adapted expression vectors (pNYCOMPS-Nterm, pNYCOMPS-Cterm, pMCSG7, pMCSG28), all bearing protease cleavable decahistidine tags for metal-affinity chromatography-based purification. All cloning and initial protein characterization were performed at the protein production core facility of the New York Consortium on Membrane Protein Structure (NYCOMPS) (27).

Protein Expression and Purification

ArnT from *Cupriavidus metallidurans* (ArnTCm) cloned in the pNYCOMPS-Nterm vector was transformed into BL21(DE3) pLysS *E. coli* competent cells, and grown overnight in 2×YT medium supplemented with 50 µg/mL kanamycin and 35 µg/mL chloramphenicol at 37° C. with shaking (240 rpm). The next day, 800 mL (large scale) or 8 mL (small scale to test expression) of the same medium were inoculated with the starter culture at 1:100 ratio, and left to grow at 37° C. with shaking (240 rpm), until OD600 reached 1.0 (approximately 3 hours). Temperature was then reduced to 22° C., protein expression was induced with 0.2 mM isopropyl β-D-1-thiogalactopyranoside (IPTG), and the culture was incubated overnight with shaking (240 rpm). Cells were harvested by centrifugation (3,700 rpm for 15 min) at 4° C., washed once with 1× phosphate buffered saline (PBS) and centrifuged again to produce a solid pellet that was stored at −80° C., until needed. For expression of selenomethionine substituted protein, cells were grown in a minimal medium of M9 salts using a kit (M9 SeMet High-Yield Growth Media Kit, Shanghai Medicilon Inc.). An additional 150 mg selenomethionine were added per liter of medium above the amount provided by the kit. The rest of the growth conditions were identical as those described for the expression of native protein.

Small scale purification tests were performed as previously described (11). For large-scale purification of ArnTCm, cell pellets were resuspended in lysis buffer containing 20 mM HEPES pH 7.5, 200 mM NaCl, 20 mM MgSO4, 10 µg/mL DNase 1.8 µg/mL RNase A. I mM tris(2-carboxyethyl) phosphine hydrochloride (TCEP), 1 mM PMSF, and Complete Mini EDTA-free protease inhibitor cocktail (Roche) used according to the manufacturer's instructions. Cells were lysed using an Emulsiflex C3 homogenizer (Avestin) and the lysate was solubilized for 1.5-2 hours with n-dodecyl-β-D-maltopyranoside (DDM; Affymetrix) added to a final concentration of 1% (w/v), in a volume of approximately 40 mL per cell pellet from 800 mL culture (~6 grams cells). Insoluble material was removed by ultracentrifugation at 34.000 rpm for 30 min at 4° C. and the protein was purified from the supernatant by metal-affinity chromatography using Ni-NTA agarose beads (Qiagen). Briefly, the supernatant was incubated with pre-equilibrated Ni-NTA agarose beads (0.7 mL per pellet from an 800 mL culture) overnight. The beads were then loaded on a column and washed with 10 column volumes of 20 mM HEPES pH 7.5, 200 mM NaCl. 60 mM Imidazole and 0.1% (w/v) DDM. Protein was eluted with 4 column volumes of 20 mM HEPES pH 7.0, 200 mM NaCl, 300 mM Imidazole, and 0.05% (w/v) DDM. Imidazole was removed from the eluted protein by exchanging buffer to 20 mM HEPES pH 7.0, 200 mM NaCl, 0.05% (w/v) DDM. 1 mM TCEP (Final protein buffer) using a PD-10 desalting column (GE Healthcare). Subsequently, the protein was subjected to TEV protease treatment (28) to cleave the decahistidine tag (~0.5 mg TEV protease added per pellet equivalent from 800 mL of initial bacterial culture) for 2-2.5 hours at 4° C. The sample was then re-passaged through the column containing Ni-NTA beads to remove the cleaved decahistidine tag, the TEV protease and uncleaved protein. A protein aliquot was subjected to size-exclusion chromatography (SEC) using either a 24 mL bed volume Superdex 200 Increase 5/150 GL column (GE Healthcare) or a TSKgel G4000SWXL, 7.8 mm×30 cm column (TOSOH Biosciences) in Final protein buffer to assess quality of the purified sample. Protein typically eluted as a sharp monodispersed peak, observed by monitoring A280, 0.7-1 mg of purified protein could typically be obtained from 800 mL of initial bacterial culture. Selenomethionine-substituted protein was purified using the same protocol as the native protein, and yields were comparable.

Crystallization.

Lipidic cubic phase (LCP) (12) mixes were prepared at room temperature by mixing concentrated protein with host lipid at 1:1.5 (w/w) protein:lipid ratio using coupled syringes. Total purified protein (not subjected to SEC) was concentrated using a centrifugal concentrator (Millipore) with a 100 kDa MW cutoff to 30-35 mg/mL and mixed with different host lipids: a) For the "apo" structure, native protein was mixed with a lipid mixture containing 0.8% decaprenyl phosphate (DecaP, Indofine Chemical Co., Inc.) and 99.2% monoolein (NuChek Prep), b) For the UndP-ArnTCm structure, native protein was mixed with a lipid mixture containing 1% undecaprenyl phosphate (UndP: Indofine Chemical Co., Inc.) and 99% monoolein, and c) Selenomethionine-substituted protein was mixed with 100% monoolein. The host lipid mixtures were prepared by dissolving appropriate amounts of both lipids in a chloroform methanol mixture (1:1 chloroform:methanol for UndP, 74:23:3 chloroform:methanol:water for decaP) and mixing them until homogeneous. The mixture was then evaporated under nitrogen gas and desiccated overnight in a vacuum desiccator. A LCP Mosquito robot (TIP Labtech) was used to dispense 50 nL of protein/lipid mixture and 750 nL of precipitant solution onto a 96-well glass plate, which was sealed with a glass cover slip and stored in a 22° C. incubator. Crystals typically appeared after 1-2 days and grew to full size in about 1 week. Initial crystallization trials were set up using the MemMeso HT screen (Molecular Dimensions). Crystals grew in (a) 30% (v/v) PEG 400, 0.1 M MES pH 6.0, 0.1 M Sodium chloride, 0.1 M Magnesium chloride hexahydrate, (b) 30% (v/v) PEG 500 DME, 0.1 M HEPES pH 7.0, 0.1 M Sodium chloride, 0.1 M Magnesium chloride hexahydrate and (c) 30% (v/v) PEG 500 DME, 0.1 M HEPES pH 7.0, 0.1 M Sodium chloride, 0.1 M Calcium chloride dihydrate. These conditions were further optimized to yield best quality crystals. Selenomethionine-substituted protein crystals showed a preference towards PEG 400 as precipitant. A tungsten carbide glass-cutter (Hampton Research) was used to cut the glass cover slip, and crystals were flash-frozen directly in liquid nitrogen without additional cryoprotection. Both ArnTCm and UndP-ArnTCm crystallized in space group P 21 21 21 with four monomers in the asymmetric unit. Unit cell parameters are given in Table 2 (46).

TABLE 2

Data collection and refinement statistics.

| | apo (decaP) - PDB code: 5EZM | bound (UndP) - PDB code: 5F15 | SeMet |
|---|---|---|---|
| Data Collection | | | |
| Wavelength (Å) | 0.979 | 0.979 | 0.979 |
| Resolution range (Å) | 46.2-2.7 (2.8-2.7) | 47.9-3.2 (3.3-3.2) | 75.5-3.3 (3.4-3.3) |
| Space group | $P2_12_12_1$ | $P2_12_12_1$ | $P2_12_12_1$ |
| Unit cell: a, b, c (Å) | 58.60, 80.63, 150.25 | 59.65, 80.32, 150.16 | 58.91, 81.21, 151.63 |
| Total reflections | 554,931 (41,515) | 89,964 (8,386) | 265,697 (25,867) |
| Unique reflections | 20,239 (2,000) | 12,427 (1,212) | 11,387 (1,120) |
| Multiplicity | 27.4 (20.8) | 7.2 (6.9) | 23.3 (23.1) |
| Completeness (%) | 99.9 (100.0) | 99.8 (99.5) | 100 (99.9) |
| Mean I/sigma(I) | 25.5 (0.9) | 5.6 (1.3) | 11.4 (2.4) |
| Wilson B-factor (Å$^2$) | 65.2 | 63.8 | 81.5 |
| R-merge | 0.38 (3.5) | 0.37 (1.9) | 0.23 (1.3) |
| R-meas | 0.39 (3.6) | 0.40 (2.0) | 0.23 (1.3) |
| R-pim | 0.075 (0.767) | 0.144 (0.748) | 0.048 (0.271) |
| CC1/2 | 0.999 (0.218) | 0.994 (0.468) | 1.000 (0.839) |
| Resolution where I/sigma (I) > 2.0 (overall) | 2.83 | 3.40 | N/A |
| Resolution where I/sigma (I) > 2.0 (along h) | 2.92 | 3.20 | N/A |
| Resolution where I/sigma (I) > 2.0 (along k) | 2.70 | 4.11 | N/A |
| Resolution where I/sigma (I) > 2.0 (along l) | 2.84 | 3.58 | N/A |
| Resolution where CC (1/2) > 0.5 (overall) | 2.86 | 3.20 | N/A |
| Resolution where CC (1/2) > 0.5 (along h) | 2.81 | 3.20 | N/A |
| Resolution where CC (1/2) > 0.5 (along k) | 2.83 | 3.85 | N/A |
| Resolution where CC (1/2) > 0.5 (along l) | 2.94 | 3.36 | N/A |
| Refinement | | | |
| Reflections used in refinement | 20.239 (1,962) | 12,427 (1,208) | N/A |
| Reflections used for R-free | 1047 (96) | 668 (59) | N/A |
| R-work | 0.21 (0.41) | 0.22 (0.32) | N/A |
| R-free | 0.26 (0.42) | 0.26 (0.38) | N/A |
| Number of non-hydrogen atoms | 4,562 | 4,804 | N/A |
| macromolecules | 4,097 | 4,171 | N/A |
| ligands | 431 | 627 | N/A |
| Protein residues | 537 | 541 | N/A |
| RMS (bonds) | 0.003 | 0.002 | N/A |
| RMS (angles) | 0.56 | 0.49 | N/A |
| Ramachandran favored (%) | 97 | 96 | N/A |
| Ramachandran allowed (%) | 2.8 | 3.7 | N/A |
| Ramachandran outliers (%) | 0 | 0.2 | N/A |
| Rotamer outliers (%) | 0.5 | 0.5 | N/A |
| Clashscore | 4.25 | 4.96 | N/A |
| Average B-factor | 75.8 | 50.6 | N/A |
| macromolecules | 74.4 | 49.5 | N/A |
| ligands | 89.6 | 57.4 | N/A |
| solvent | 65.1 | 44.2 | N/A |
| Number of TLS groups | 2 | 2 | N/A |

Statistics for the highest-resolution shell are shown in parentheses.

Data Collection and Structure Determination.

X-ray diffraction data were collected on the NECAT beamlines 24-ID-C and 24-ID-E at the Advanced Photon Source (Argonne National Laboratory, Argonne, Ill.). For structure determination, six datasets collected from selenomethionine-substituted protein crystals were scaled together using XDS/XSCALE (29). Twenty one selenium sites were located using these data employing SHELXD via HKL2MAP software (30, 31). The sites were input to the program PHASER (32) for SAD phasing. PHASER was able to locate six additional sites. The resulting phases showed helical features in the electron density map. Initial phases were improved by placing a model derived from PDB entry 3WAJ in the electron density map using the program MOLREP (33). One copy of the molecule could be clearly positioned in the electron density map. PHASER was run once again using the selenium sites and the positioned model together. The resulting phases were subjected to density modification using the program RESOLVE (34), yielding phases of great quality that allowed tracing the molecule in the electron density map.

Data were collected from five isomorphous crystals for the "apo" structure, and from one crystal for the UndP-bound structure. The datasets were indexed, integrated, scaled and merged using XDS (29) and AIMLESS (35). The initial model was rigid-body fitted in the final datasets using the PHENIX crystallographic software package (36). The models were manually corrected and completed using Coot (37), and refined using PHENIX, alternating between cycles of manual building in Coot and refinement in PHENIX. The electron density maps for both structures featured many partially-ordered lipid molecules which most likely correspond to monoolein. As no head groups or identifying features were discernable in the densities, all unidentified lipids were modeled as isolated alkyl chains and assigned the residue code UNL, the PDB recommended code for all unidentified ligands. The UndP-bound dataset contained densities for the head and tail of UndP. The "apo" dataset also had a density inside cavity 3 corresponding to the two terminal prenyls of decaP or an endogenous polyprenyl ligand (since a similar density was observed in a true "apo" dataset, from crystals prepared using monoolein alone as a host lipid, data not shown). The SeMet dataset did not feature a similar density. UndP was built from a SMILES string and had geometrical restrains generated using the program eLBOW (in the PHENIX suite). It was manually fitted to the densities and position optimized during regular refinement of the model with PHENIX. UndP in the bound dataset was assigned the residue code 5TR. Many ordered water molecules can be seen in the "apo" structure and some in the UndP dataset, and have been added to each model. The final ArnTCm model has an Rwork/Rfree of 0.21/0.26 and the final UndP-ArnTCm model an Rwork/Rfree of 0.22/0.26. All protein structure figures were prepared using UCSF Chimera (38).

The densities presented used for building the UndP ligand in the bound structure correspond to a feature-enhanced omit map for UndP. To remove the possibility of bias, the UndP ligand was set to zero occupancy, and the coordinates for the resulting model were perturbed using phenix.dynamics. The model was then refined against the UndP-bound dataset and a feature-enhance map was calculated in PHENIX.

In Silico Molecular Docking

Initial structures for the 4-Amino-4-deoxy-L-arabinose-phospate, with either zero, one, two or three prenyl group(s) attached to it were built using MarvinSketch. These four initial structures were prepared for docking using Ligprep (version 2.9, Schrödinger Inc.), with the OPLS 2.1 force field. Possible ionization states of the phosphate and amine groups around pH 7 (+/−2) were calculated using the Epik option.

The prepared ligand structures were docked on the ArnTCm structure (UndP-bound conformation), using Glide (version 6.2, Schrödinger Inc.). The standard precision flexible docking procedure was used, allowing the generation and docking of multiple ligand conformations. The search space was defined as a cube of 36 Å edge length centered on the center of mass of residues Asp 55, Asp 158 and Tyr 59. As part of the standard Glide search algorithm, the diameter midpoint of each ligand had to stay within a smaller concentric cube (size set at 16 Å edge length). The potential for the non-polar part of the ligands was "softened" by scaling down the van der Waals radii of atoms with a partial charge smaller than 0.15, by a factor of 0.85.

Finally, poses with the best energy were kept and post-docking minimization was performed. Number of poses obtained is as follows: No prenyl (only sugar-phosphate) 57, 1 prenyl group 37, 2 prenyl groups 48, and 3 prenyl groups 38. The poses obtained from the ligand containing 3 prenyl groups show the best match with experimentally-derived positions for the phosphate and first three prenyl groups of UndP.

Isolation of Labeled Lipid A

Overnight bacterial cultures were diluted to an OD600 of 0.05 and labeled with 2.5 µCi ml-1 32Pi (Perkin Elmer) in 5 mL LB broth. The cells were harvested at OD600 1.0. Labeled 32P-lipid A isolation, separation and visualization were performed as previously described (9).

Isolation of Lipid a and Mass Spectrometry

A total of 500 mL bacterial culture was grown in LB medium at 37° C. When the culture reached OD600 1.0, cells were harvested by Centrifugation at 10,000×g for 10 minutes. Lipid A was prepared by mild acidic hydrolysis (39). Lipid A species were separated by Thin Layer Chromatography (TLC) Silica Gel 60 (Merck KGaA) using the solvent system chloroform/pyridine/88% formic acid/water (50:50:16:5). Lipid A was purified as previously described (7) and analyzed using a MALDI-TOF/TOF (ABI 4700 Proteomic Analyzer) mass spectrometer in the negative-ion linear mode, also as previously described (9).

Determination of Polymyxin B Minimum Inhibitory Concentration (MIC)

Overnight cultures were diluted 100-fold in fresh LB medium and grown until OD600 reached 0.5. To determine the MIC value, these cultures were diluted again to OD600 0.05 in LB containing a range of the antimicrobial peptide concentrations. Cultures were incubated for 3 hours at 37° C., and 200 rpm. The MIC was defined as the lowest concentration of polymyxin B that reduced the cell growth (A600) by 50% compared to the growth in LB without polymyxin B. The table in FIG. 2C indicates the MIC ranges after 3 biological repetitions.

Mutagenesis and Polymyxin B Growth Assay.

Mutations of ArnTSt were generated with whole plasmid PCR using Phusion High-Fidelity PCR Master Mix with HF buffer (New England Biolabs) and custom primers. The "wild-type" ArnTSt used carries the background mutation P547A (Note: These methods apply only for polymyxin growth assay used for mutagenesis functional experiments. The implementation of the polymyxin growth assay for drug screening, as described below, uses a true wt ArnTSt gene for expression of S. typhimurium ArnT). This mutation has been shown to improve the yield of purified protein (13), and is present in every mutant examined here using the polymyxin B growth assay. All mutants shown have been tested for total ArnTSt protein expression and all express to comparable levels. The in vivo polymyxin B growth assay used to assess function of ArnTSt mutants has been described previously (13, 14). Briefly, plasmids encoding mutant ArnTSt proteins were electroporated into BL21 (DE3) ΔarnT *E. coli* cells, plated onto LB/ampicillin plates and grown overnight at 37° C. $10^5$ cells from a single colony were inoculated into 2 mL LB/ampicillin and incubated overnight at 37° C. with shaking in the presence and absence of 2 μg/mL polymyxin. Growth was continuously quantitated spectrophotometrically at 600 nm with a Varioscan microplate reader (Thermo Scientific). Assays were carried out twice and in duplicate for each mutation. Empty vector (pET21) and P547A ArnTSt (wt) were included in all experiments as polymyxin-sensitive and polymyxin-resistant controls, respectively. All error bars in bar graphs represent standard deviation.

96-Well Plate Implementation of the Polymyxin B Growth Assay for Compound Screening.

Three strains were used for the implementation of the polymyxin B growth assay for compound screening in a 96-well plate format: (1) BL21 (DE3) *E. coli* strain (referred to as BL21). BL21 strain is inherently resistant to polymyxin B as it carries the endogenous *E. coli* ArnT gene. *E. coli* BL21 strain is used to test efficacy of tested compounds towards the *E. coli* ArnT protein. (2) *E. coli* BL21(DE3) ΔArnT the endogenous *E. coli* ArnT gene has been deleted, thus rendering the *E. coli* BL21 ΔArnT strain sensitive to polymyxin B (referred to as ΔArnT). (3) *E. coli* BL21(DE3) ΔArnT that has been transformed with the plasmid pGi24 that expresses the wt *Salmonella typhimurium* ArnT (referred to as Gi24). Expression of wt *Salmonella typhimurium* ArnT restores resistance to polymyxin B demonstrated by growth of the Gi24 strain in the presence of PMXB. The Gi24 strain is used to test efficacy of tested compounds towards the *Salmonella typhimurium* ArnT protein.

Overnight cultures of the three strains were used to inoculate LB media containing 100 μg/ml Ampicillin alone (PMXB−) or 100 μg/ml and 3 μg/ml Polymyxin B (PMXB+) at 1:2000 dilution, as appropriate. Compounds to be screened were dissolved in DMSO to a stock concentration of 100 mM and diluted to a final concentration of 0.5 mM in aliquots of the different strains in PMXB− and PMXB+ LB media. The resulting aliquots of test strains (BL21 and Gi24) with test compounds in PMXB− and PMXB+ LB media were transferred to a 96-well plate producing triplicates of each sample laid out in a documented manner. Each well was loaded with 150 μl of appropriate formulation (strain/compound/PMXB). The 96-well plate was transferred to an Epoch 2 microplate reader (Biotek) and shaken continuously at 37° C. Growth was continuously quantitated spectrophotometrically at 600 nm. Each compound was tested in two independent experiments for retardation of growth of test strains (BL21 and Gi24).

DISCUSSION

ArnTCm represents the first structure of a lipid-to-lipid glycosyltransferase and provides a structural framework for understanding the function of ArnTs in molecular detail. Overall, the structures described herein provide insight into how amphipathic bilayer-embedded substrates are utilized by integral membrane enzymes, and illustrate a mechanism for the ArnT family. These structures enable the informed design of novel compounds targeted at reversing resistance to polymyxin-class antibiotics.

"A" REFERENCES

A1. Infectious Diseases Society of A. 2010. The 10×'20 Initiative: pursuing a global commitment to develop 10 new antibacterial drugs by 2020. Clin Infect Dis 50:1081-3.

A2. 2014. Antimicrobial Resistance Global Report on Surveillance, World Health Organization.

A3. 2013. Antibiotic Resistance Threats in the United States, 2013. Center for Disease Control and Prevention.

A4. Payne D J, Gwynn M N, Holmes D J. Pompliano D L. 2007. Drugs for bad bugs: confronting the challenges of antibacterial discovery. Nat Rev Drug Discov 6:29-40.

A5. Boucher H W, Talbot G H, Benjamin D K, Jr., Bradley J, Guidos R J, et al. 2013. 10×'20 Progress—development of new drugs active against gram-negative bacilli: an update from the Infectious Diseases Society of America. Clin Infect Dis 56:1685-94.

A6. Curcio D. 2014. Multidrug-resistant Gram-negative bacterial infections: are you ready for the challenge? Curt Clin Pharmacol 9:27-38.

A7. Pop-Vicas A, Opal S M. 2014. The clinical impact of multidrug-resistant gram-negative bacilli in the management of septic shock. *Virulence* 5:206-12.

A8. Viale P. Giannella M. Tedeschi S, Lewis R. 2015. Treatment of MDR-Gram negative infections in the 21st century: a never ending threat for clinicians. Curr Opin Pharmacol 24:30-7.

A11. Kumarasamy K K, Toleman M A, Walsh T R, Bagaria J, Butt F, et al. 2010. Emergence of a new antibiotic resistance mechanism in India. Pakistan, and the U K: a molecular, biological, and epidemiological study. Lancet Infect Dis 10:597-602.

A12. Velkov T, Roberts K D. Nation R L, Thompson P E, Li J. 2013. Pharmacology of polymyxins: new insights into an 'old' class of antibiotics. Future Microbiol 8:711-24.

A13. Li J, Nation R L, Turnidge J D, Milne R W, Coulthard K, et al. 2006. Colistin: the re-emerging antibiotic for multidrug-resistant Gram-negative bacterial infections. Lancet Infect Dis 6:589-601.

A14. Bergen P J, Landersdorfer C B, Zhang J, Zhao M. Lee H J, et al. 2012. Pharmacokinetics and pharmacodynamics of 'old' polymyxins: what is new? Diagn Microbiol Infect Dis 74:213-23.

A15. Velkov T, Thompson P E, Nation R L, Li J. 2010. Structure—activity relationships of polymyxin antibiotics. J Med Chem 53:1898-916.

A16. Cajal Y, Rogers J, Berg O G, Jain M K. 1996. Intermembrane molecular contacts by polymyxin B mediate exchange of phospholipids. Biochemistry 35:299-308.

A17. Clausell A, Garcia-Subirats M. Pujol M, Busquets M A, Rabanal F. Cajal Y. 2007. Gram-negative outer and inner membrane models: insertion of cyclic cationic lipopeptides. J Phys Chem B 111:551-63.

A18. Zhiliang Y. Wangrong Q, Jianxun L. Shisong F, Juanping Q. 2015. Antibacterial Mechanisms of Polymyxin and Bacterial Resistance. BioMed Research International.

A19. Mares I, Kumaran S, Gobbo M, Zerbe O. 2009. Interactions of lipopolysaccharide and polymyxin studied by NMR spectroscopy. J Biol Chem 284:11498-506.

A20. Tan C H, Li J, Nation R L. 2007. Activity of colistin against heteroresistant *Acinetobacter baumannii* and emergence of resistance in an in vitro pharmacokinetic/pharmacodynamic model. Antimicrob Agents Chemother 51:3413-5.

A21. Bergen P J, Li J, Nation R L. Turnidge J D, Coulthard K, Milne R W. 2008. Comparison of once-, twice- and thrice-daily dosing of colistin on antibacterial effect and emergence of resistance: studies with *Pseudomonas aeruginosa* in an in vitro pharmacodynamic model. J Antimicrob Chemother 61:636-42.

A22. Poudyal A, Howden B P, Bell J M. Gao W, Owen R J, et al. 2008. In vitro pharmacodynamics of colistin against multidrug-resistant *Klebsiella pneumoniae. J Antimicrob Chemother* 62:1311-8.

A23. Matthaiou D K, Michalopoulos A, Rafailidis P I, Karageorgopoulos D E. Papaioannou V, et al. 2008. Risk factors associated with the isolation of colistin-resistant gram-negative bacteria: a matched case-control study. Crit Care Med 36:807-11.

A24. Raetz C R, Reynolds C M, Trent M S, Bishop R E, 2007. Lipid A modification systems in gram-negative bacteria. Annu Rev Biochem 76:295-329.

A25. Brogden K A. 2005. Antimicrobial peptides: pore formers or metabolic inhibitors in bacteria? Nat Rev Microbiol 3:238-50.

A26. Needham B D, Trent M S. 2013. Fortifying the barrier: the impact of lipid A remodelling on bacterial pathogenesis. Nat Rev Microbiol 11:467-81.

A27. Gales A C. Jones R N, Sader H S. 2011. Contemporary activity of colistin and polymyxin B against a worldwide collection of Gram-negative pathogens: results from the SENTRY Antimicrobial Surveillance Program (2006-09). J Antimicrob Chemother 66:2070-4.

A57. Kline, T., et al., Synthesis of and evaluation of lipid A modification by 4-substituted 4-deoxy arabinose analogs as potential inhibitors of bacterial polymyxin resistance. Bioorg Med Chem Lett, 2008. 18(4): p. 1507-10.

A58. Tavares-Carreon. F., K. B. Patel, and M. A. Valvano, *Burkholderia cenocepacia* and *Salmonella enterica* ArnT proteins that transfer 4-amino-4-deoxy-1-arabinose to lipopolysaccharide share membrane topology and functional amino acids. Sci Rep, 2015. 5: p. 10773.

REFERENCES

1. A. P. Zavaski, L. Z. Goldani, J. Li, R. L. Nation, Polymyxin B for the treatment of multidrug-resistant pathogens: a critical review. *J. Antimicrob. Chemother.* 60, 1206-1215 (2007).
2. D. Landman, C. Georgescu, D. A. Martin, J. Quale, Polymyxins revisited. *Clin. Microbiol. Rev.* 21. 449-465 (2008).
3. J. Mares, S. Kumaran, M. Gobbo, O. Zerbe. Interactions of lipopolysaccharide and polymyxin studied by NMR spectroscopy. *J. Biol. Chem.* 284, 11498-11506 (2009).
4. C. R. H. Raetz, C. M. Reynolds, M. S. Trent, R. E. Bishop, Lipid A modification systems in gram-negative bacteria. *Annu. Rev. Biochem* 76. 295-329 (2007).
5. K. A. Brogden, Antimicrobial peptides: pore formers or metabolic inhibitors in bacteria?*Nat. Rev. Microbiol.* 3, 238-250 (2005).
6. B. D. Needham, M. S. Trent, Fortifying the barrier: the impact of lipid A remodelling on bacterial pathogenesis. *Nat. Rev. Microbiol.* 11, 467-481 (2013).
7. M. S. Trent, A. A. Ribeiro, S. Lin, R. J. Cotter, C. R. H. Raetz, An inner membrane enzyme in *Salmonella* and *Escherichia coli* that transfers 4-amino-4-deoxy-L-arabinose to lipid A: Induction in polymyxin-resistant mutants and role of a novel lipid-linked donor. *J. Biol. Chem.* 276. 43122-43131 (2001).
8. M. S. Trent et al., Accumulation of a polyisoprene-linked amino sugar in polymyxin-resistant *Salmonella typhimurium* and *Escherichia coli*: structural characterization and transfer to lipid A in the periplasm. *J. Biol. Chem.* 276, 43132-43144 (2001).
9. C. M. Herrera, J. V. Hankins, M. S. Trent, Activation of PmrA inhibits LpxT-dependent phosphorylation of lipid A promoting resistance to antimicrobial peptides. *Mol. Microbiol.* 76, 1444-1460 (2010).
10. H. Lee, F.-F. Hsu, J. Turk, E. A. Groisman, The PmrA-regulated pmrC gene mediates phosphoethanolamine modification of lipid A and polymyxin resistance in *Salmonella enterica. J. Bacteriol.* 186, 4124-4133 (2004).
11. F. Mancia, J. Love, High-throughput expression and purification of membrane proteins. J. Struct. Biol. 172, 85-93 (2010).
12. M. Caffrey, Crystallizing Membrane Proteins for Structure Determination: Use of Lipidic Mesophases. *Annu. Rev. Biophys.* 38, 29-51 (2009).
13. N. A. Impellitteri, J. A. Merten, L. E. Bretscher, C. S. Klug, Identification of a functionally important loop in *Salmonella typhimurium* ArnT. *Biochemistry* 49, 29-35 (2010).
14. L. E. Bretscher, M. T. Morrell, A. L. Funk. C. S. Klug, Purification and characterization of the L-Ara4N transferase protein ArnT from *Salmonella typhimurium. Protein Erpr. Purif* 46. 33-39 (2006).
15. T. W. Cullen et al., *Helicobacter pylori* versus the host: remodeling of the bacterial outer membrane is required for survival in the gastric mucosa. *PLoS Pathog.* 7, e 1002454 (2011).
16. X. Wang. S. C. McGrath, R. J. Cotter, C. R. H. Raetz, Expression cloning and periplasmic orientation of the *Francisella novicida* lipid A 4'-phosphatase LpxF. *J. Biol. Chem.* 281, 9321-9330 (2006).
17. F. Tavares-Carreón, K. B. Patel, M. A. Valvano, *Burkholderia cenocepacia* and *Salmonella enterica* ArnT proteins that transfer 4-amino-4-deoxy-1-arabinose to lipopolysaccharide share membrane topology and functional amino acids. *Sci. Rep.* 5 (2015), doi: 10. 1038/srep 10773.
18. L. L. Lairson, B. Henrissat, G. J. Davies, S. G. Withers, Glycosyltransferases: structures, functions, and mechanisms. *Annu. Rev. Biochem.* 77, 521-555 (2008).
19. C. Lizak, S. Gerber. S. Numao, M. Aebi, K. P. Locher, X-ray structure of a bacterial oligosaccharyltransferase. *Nature.* 474, 350-355 (2011).
20. S. Matsumoto et al., Crystal structures of an archaeal oligosaccharyltransferase provide insights into the catalytic cycle of N-linked protein glycosylation. *Proc. Natl. Acad Sci.* 110, 17868-17873 (2013).
21. Z. Zhou, A. A. Ribeiro, C. R. H. Raetz, High-resolution NMR spectroscopy of lipid A molecules containing 4-amino-4-deoxy-1-arabinose and phosphoethanolamine substituents. Different attachment sites on lipid A molecules from NH4VO3-treated *Escherichia coli* versus kdsA mutants of *Salmonella typhimurium. J. Biol. Chem.* 275, 13542-13551 (2000).
22. J. B. Thoden, H. M. Holden, Active site geometry of glucose-1-phosphate uridylyltransferase. *Protein Sci.* 16, 1379-1388 (2007).

23. C. Lizak et al., Unexpected reactivity and mechanism of carboxamide activation in bacterial N-linked protein glycosylation. *Nat. Commun.* 4 (2013), doi: 10.1038/ncomms3627.
24. M. A. Lomize, I. D. Pogozheva, H. Joo, H. I. Mosberg, A. L. Lomize, OPM database and PPM web server: resources for positioning of proteins in membranes. *Nucleic Acids Res.* 40, D370-D376 (2012).
25. N. R. Voss, M. Gerstein, 3V: cavity, channel and cleft volume calculator and extractor. *Nucleic Acids Res.* 38, W555-W562 (2010).
26. M. Punta et al., Structural genomics target selection for the New York consortium on membrane protein structure. *J. Struct. Funct. Genomics.* 10, 255-268 (2009).
27. J. Love et al., The New York Consortium on Membrane Protein Structure (NYCOMPS): a high-throughput platform for structural genomics of integral membrane proteins. *J. Struct. Funct. Genomics.* 11. 191-199 (2010).
28. R. B. Kapust. J. Tözsér, T. D. Copeland, D. S. Waugh, The P1' specificity of tobacco etch virus protease. *Biochem. Biophys. Res. Commun.* 294, 949-955 (2002).
29. W. Kabsch, Integration, scaling, space-group assignment and post-refinement. *Acta Crstallogr. D Biol. Crystallogr.* 66, 133-144 (2010).
30. G. M. Sheldrick, A short history of SHELX. *Acta Crystallogr. A.* 64, 112-122 (2008).
31. T. Pape. T. R. Schneider, HKL2MAP: a graphical user interface for macromolecular phasing with SHELX programs. *J. Appl. Crystallogr.* 37, 843-844 (2004).
32. A. J. McCoy et al., Phaser crystallographic software. *J. Appl. Crystallogr.* 40, 658-674 (2007).
33. A. Vagin, A. Teplyakov, Molecular replacement with MOLREP. *Acta Crystallogr. D Biol. Crystallogr.* 66, 22-25 (2010).
34. T. C. Terwilliger, Maximum-likelihood density modification. *Acta Crystallogr. D Biol. Crystallogr.* 56, 965-972 (2000).
35. P. R. Evans, G. N. Murshudov, How good are my data and what is the resolution? *Acta Crstallogr. D Biol. Crystallogr.* 69, 1204-1214 (2013).
36. P. D. Adams et al. PHENIX: a comprehensive Python-based system for macromolecular structure solution. *Acta Crystallogr. D Biol. Crystallogr.* 66, 213-221 (2010).
37. P. Emsley. B. Lohkamp, W. G. Scott, K. Cowtan. Features and development of Coot. *Acta Crystallogr. D Biol. Crystallogr.* 66, 486-501 (2010).
38. E. F. Pettersen et al., UCSF Chimera—a visualization system for exploratory research and analysis. *J. Comput. Chem.* 25, 1605-1612 (2004).
39. Z. Zhou, S. Lin, R. J. Cotter, C. R. Raetz, Lipid A modifications characteristic of *Salmonella typhimurium* are induced by $NH_4VO_3$ in *Escherichia coli* K12. Detection of 4-amino-4-deoxy-L-arabinose, phosphoethanolamine and palmitate. *J. Biol. Chem.* 274, 18503-18514 (1999).
40. M. Laitaoja, J. Valjakka, J. Jänis, Zinc Coordination Spheres in Protein Structures. *Inorg. Chem.* 52, 10983-10991 (2013).
41. K. Katoh, H. Toh, Recent developments in the MAFFT multiple sequence alignment program. *Brief. Bioinform.* 9, 286-298 (2008).
42. M. A. Larkin et al., Clustal W and Clustal X version 2.0. *Bioinformatics.* 23, 2947-2948 (2007).
43. D. H. Huson, C. Scornavacca, Dendroscope 3: An Interactive Tool for Rooted Phylogenetic Trees and Networks. *Syst. Biol.* 61. 1061-1067 (2012).
44. J. Pei, B.-H. Kim, N. V. Grishin, PROMALS3D: a tool for multiple protein sequence and structure alignments. *Nucleic Acids Res.* 36. 2295-2300 (2008).
45. G. E. Crooks, G. Hon, J.-M. Chandonia, S. E. Brenner, WebLogo: A Sequence Logo Generator. *Genome Res.* 14. 1188-1190 (2004).
46. V. I. Petrou et al., Structures of aminoarabinose transferase ArnT suggest a molecular basis for lipid A glycosylation. *Science.* 351, 608-612 (2016).

Many modifications and variations of this invention can be made without departing from its spirit and scope, as will be apparent to those skilled in the art. The invention is defined by the terms of the appended claims, along with the full scope of equivalents to which such claims are entitled. The specific embodiments described herein, including the following examples, are offered by way of example only, and do not by their details limit the scope of the invention.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

What is claimed is:

1. A method of treating, preventing, or inhibiting a gram negative infection in a patient, the method comprising administering to the patient an effective amount of a compound having the formula according to:

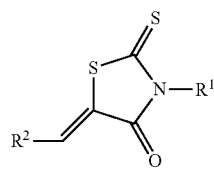

Formula III wherein:
$R^1$ is a moiety-$(CH_2)n$-COOH;
n is 1 to 3;
$R^2$ is selected from the group consisting of:

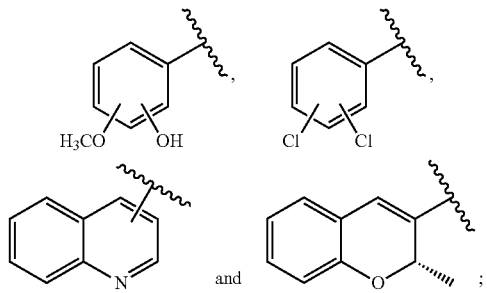

or a pharmaceutically acceptable salt, solvate, poly-morph, tautomer or prodrug thereof, wherein the method further comprises administering to the patient at least one additional antibacterial agent comprising a polymyxin class antibiotic.

2. The method of claim 1, wherein the polymyxin is Polymyxin B or Polymyxin E.

3. The method of claim 1, wherein the gram negative infection is caused by one or more bacteria from the class Enterobacteriaceae or Gammaproteobacteria.

4. The method of claim 3, wherein the Enterobacteriaceae comprises one or more organisms from the genus *Salmonella, Escherichia, Yersinia, Klebsiella, Shigella, Proteus, Enterobacter, Serratia,* or *Citrobacter.*

5. The method of claim 4, wherein the genus is at least one species comprising: *Escherichia coli, Klebsiella pneumoniae, Proteus vulgaris, Salmonella typhimurium,* and *Serratia marcescens.*

6. The method of claim 3, wherein the gammaproteobacteria comprises one or more organisms from the genus *Acinetobacter* or *Pseudomonas.*

7. The method of claim 6, wherein the genus is at least one species comprising: *A. baumannii* or *P. aeruginosa.*

8. The method of claim 1, wherein the patient is a mammal.

9. The method of claim 1, comprising administering a pharmaceutically effective amount of the compound.

10. A method for increasing susceptibility of at least one drug resistant gram negative organism to polymyxin class antibiotics, the method comprising contacting the at least one gram negative organism with an effective amount of a compound having the formula according to:

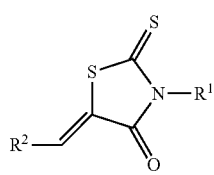

Formula III wherein:
$R^1$ is a moiety-$(CH_2)n$-COOH;
n is 1 to 3;
$R^2$ is selected from the group consisting of:

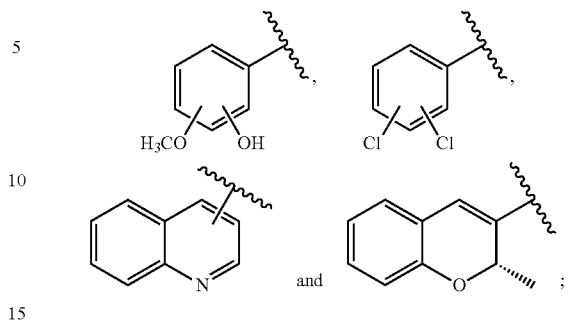

or a pharmaceutically acceptable salt, solvate, poly-morph, tautomer or prodrug thereof.

11. A method for inhibiting aminoarabinase glycosyltransferase (ArnT) of a gram negative bacterium, the method comprising: contacting the bacterium with a compound having the formula according to:

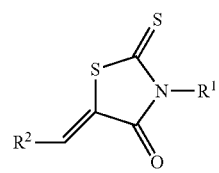

Formula III wherein:
$R^1$ is a moiety-$(CH_2)n$-COOH;
n is 1 to 3;
$R^2$ is selected from the group consisting of:

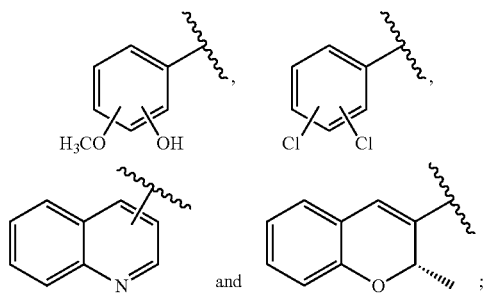

or a pharmaceutically acceptable salt, solvate, poly-morph, tautomer or prodrug thereof, in an amount effective to block L-Ara4N binding to an ArnT active site.

12. A compound comprising:
3[(5E)-5-[[(2S)-2-methyl-2H-chromen-3-yl]methyl-idene]-2,4-dioxo-1,3-thiazolidin-3-yl]propanoic acid;
or a pharmaceutically acceptable salt, solvate, poly-morph, tautomer or prodrug thereof.

13. A method of treatment or prophylaxis of a disorder or disease mediated by infection with at least one gram negative organism, the method comprising administering to a patient in need thereof a therapeutically effective amount of compound having the formula according to:

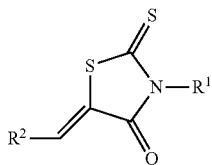

Formula III wherein:
R¹ is a moiety-(CH₂)n-COOH;
  n is 1 to 3;
R² is selected from the group consisting of:

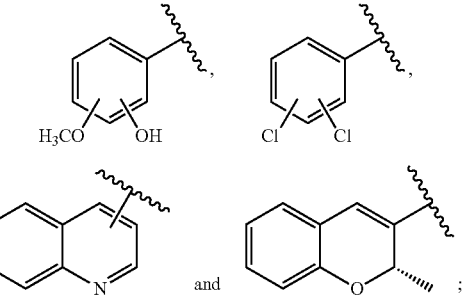

or a pharmaceutically acceptable salt, solvate, poly-morph, tautomer or prodrug thereof, in combination with at least one additional antibacterial agent or compound.

14. A composition comprising a first compound and a second agent, the first compound having the formula:

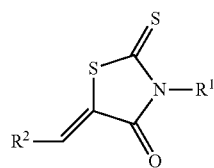

Formula III wherein:
R¹ is a moiety-(CH₂)n-COOH;
  n is 1 to 3;
R² is selected from the group consisting of:

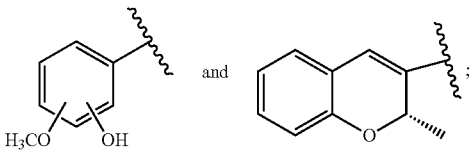

or a pharmaceutically acceptable salt, solvate, poly-morph, tautomer or prodrug thereof, wherein the second agent is an antibacterial agent or compound comprising a polymyxin class antibiotic.

15. The composition of claim 14, wherein the polymyxin is Polymyxin B or Polymyxin E.

16. The composition of claim 14, wherein the first compound comprises:
   2-[(5E)-5-[(2-hydroxy-3-methoxyphenyl)methylidene]-4-oxo-2-sulfanylidene-1,3-thiazolidin-3-yl]acetate;
   3-[(5E)-5-[[(2S)-2-methyl-2H-chromen-3-yl]methylidene]-2,4-dioxo-1,3-thiazolidin-3-yl]propanoic acid;
   or any combination thereof.

* * * * *